United States Patent
Rude et al.

(10) Patent No.: US 10,208,294 B2
(45) Date of Patent: Feb. 19, 2019

(54) ACYL-ACP REDUCTASE WITH IMPROVED PROPERTIES

(71) Applicant: Reg Life Sciences, LLC, Ames, IA (US)

(72) Inventors: Mathew Rude, South San Francisco, CA (US); Na Trinh, South San Francisco, CA (US); Andreas Schirmer, South San Francisco, CA (US); Jacob Gano, South San Francisco, CA (US)

(73) Assignee: REG LIFE SCIENCES, LLC, South San Francisco, CA (US)

( * ) Notice: Subject to any disclaimer, the term of this patent is extended or adjusted under 35 U.S.C. 154(b) by 351 days.

(21) Appl. No.: 15/222,657

(22) Filed: Jul. 28, 2016

(65) Prior Publication Data

US 2016/0348080 A1 Dec. 1, 2016

Related U.S. Application Data

(63) Continuation of application No. 14/761,299, filed as application No. PCT/US2014/011859 on Jan. 16, 2014, now Pat. No. 9,683,219.

(60) Provisional application No. 61/753,273, filed on Jan. 16, 2013.

(51) Int. Cl.
| | |
|---|---|
| *C12N 9/02* | (2006.01) |
| *C12P 7/64* | (2006.01) |
| *C12P 7/24* | (2006.01) |
| *C12P 7/04* | (2006.01) |

(52) U.S. Cl.
CPC .............. *C12N 9/0008* (2013.01); *C12P 7/04* (2013.01); *C12P 7/24* (2013.01); *C12P 7/6409* (2013.01); *C12Y 102/0108* (2013.01)

(58) Field of Classification Search
None
See application file for complete search history.

(56) References Cited

U.S. PATENT DOCUMENTS

| | | | |
|---|---|---|---|
| 5,000,000 A | 3/1991 | Ingram et al. | |
| 5,028,539 A | 7/1991 | Ingram et al. | |
| 5,424,202 A | 6/1995 | Ingram et al. | |
| 5,482,846 A | 1/1996 | Ingram et al. | |
| 5,602,030 A | 2/1997 | Ingrahm et al. | |
| 5,939,250 A | 8/1999 | Short | |
| 5,965,408 A | 10/1999 | Short | |
| 7,169,588 B2 | 1/2007 | Burch et al. | |
| 7,794,969 B1 * | 9/2010 | Reppas ................. | C12N 9/0004 435/41 |
| 8,097,439 B2 | 1/2012 | Alibhai et al. | |
| 8,110,093 B2 | 2/2012 | Friedman et al. | |
| 8,110,670 B2 | 2/2012 | Hu et al. | |
| 8,183,028 B2 | 5/2012 | Alibhai et al. | |
| 8,268,599 B2 | 9/2012 | Schirmer et al. | |
| 8,283,143 B2 | 10/2012 | Hu et al. | |
| 8,323,924 B2 | 12/2012 | Schirmer et al. | |
| 8,372,610 B2 | 2/2013 | Lee et al. | |
| 8,530,221 B2 | 9/2013 | Hu et al. | |
| 2009/0140696 A1 | 6/2009 | Okuto | |
| 2010/0105963 A1 | 4/2010 | Hu | |
| 2011/0072714 A1 | 3/2011 | Gaertner | |
| 2011/0206630 A1 | 8/2011 | Rude | |
| 2012/0282663 A1 | 11/2012 | Schirmer et al. | |

FOREIGN PATENT DOCUMENTS

| | | |
|---|---|---|
| WO | WO-91/16427 | 10/1991 |
| WO | WO-2007/136762 A2 | 11/2007 |
| WO | WO-2008/119082 A2 | 10/2008 |
| WO | WO-2009/140695 A2 | 11/2009 |
| WO | WO-2009/140696 | 11/2009 |
| WO | WO-2010/062480 A2 | 6/2010 |
| WO | WO-2010/127318 | 11/2010 |
| WO | WO-2011/127409 | 10/2011 |

OTHER PUBLICATIONS

Altschul et al. "Basic Local Alignment Search Tool," (1990) J. Mol. Biol. 215(3):403-410.
Altschul et al. "Protein Database Searches Using Compositionally Adjusted Substitution Matrices," (2005) FEBS J. 272(20):5101-5109.
Amann et al, "Tightly regulated tac promoter vectors useful for the expression of unfused and fused proteins in *Escherichia coli*," Gene, 69: 301-315 (1988).
Arkin et al. "An algorithm for protein engineering: Simulations of recursive ensemble mutagenesis," (1992) Proc. Natl. Acad. Sci. U.S.A. vol. 89 pp. 7811-7815.
Arnold, "Protein engineering for unusual environments," Curr. Opin. Biotech., 4: 450-455 (1993).
Baldari et al. "A novel leader peptide which allows efficient secretion of a fragment of human interluken 1 beta in *Saccharomyces serevisiae*," (1987) EMBO J. 6:229-234.
Bowie et al. "Deciphering the Message in Protein Sequences: Tolerance to Amino Acid Substitutions," (1990) Science, 247:1306-1310.
Caldwell et al, "Randomization of Genes by PCR Mutagenesis," PCR Methods Applic., 2: 28-33 (1992).
Clark, "Regulation of Fatty Acid Degration in *Escherichia coli*: Analysis by Operon Fusion," J Bacteriol. (1981) 148(2):521-6.
Delagrave et al., "Searching Sequence Space to Engineer Proteins: Exponential Ensemble Mutagenesis," Biotech. Res, 11: 1548-1552 (1993).

(Continued)

*Primary Examiner* — Suzanne M Noakes
*Assistant Examiner* — Jae W Lee
(74) *Attorney, Agent, or Firm* — Foley & Lardner LLP

(57) ABSTRACT

The disclosure relates to acyl-ACP reductase (AAR) enzyme variants that result in improved fatty aldehyde and fatty alcohol production when expressed in recombinant host cells. The disclosure further relates to methods of making and using such AAR variants for the production of fatty alcohol compositions having particular characteristics.

16 Claims, 10 Drawing Sheets
Specification includes a Sequence Listing.

(56) References Cited

OTHER PUBLICATIONS

Genbank Accession No. AEX28225.1, published Jan. 11, 2012, 1 page.
Office Action issued on Chinese Application 201480004992.3, dated Nov. 28, 2016, English Translation.
Examination Report issued on Australian Appl. 2014207522, dated Aug. 9, 2016.
Notice of Reasons for Rejection issued on Japanese Application 2015-553830, dated Sep. 14, 2016 English Translation only.
Notification of Reasons for Refusal issued on Korean Application 10-2015-7021992, dated Sep. 20, 2016.
Search Report issued on European Application 16181205.2, dated Oct. 14, 2016.
Kurjan et al., Structure of a Yeast Pheromone Gene (MFx): A Putative x-Factor precursor Contains Four Tandem Copies of Mature x-Factor, Cell, vol. 30, pp. 933-943 (1982).
Leung et al. "A Journal of Methods in Cell and Molecular Biology," Technique vol. 1, No. 1, Aug. 1989 pp. 11-15.
Lucklow et al. "High Level Expression of Nonfused Foreign Genes with Autographa californica Nuclear Polyhedrosis Virus Expression Vectors," (1989) Virology 170, pp. 31-39.
Maniatis et al. "Regulation of Inducible and Tissue-Specific Gene Expression," (1987) Science 236:1237-1245.
Non-Final Office Action on U.S. Appl. No. 14/761,299, dated Sep. 16, 2016.
Needleman and Wunsch "A General Method Applicable to the Search for Similarities in the Amino Acid Sequence of Two Proteins," (1970) J. Mol. Biol. 48:444-453.
Reidhaar-Olson et al., "Combinatorial Cassette Mutagenesis as a Probe of the Informational Content of Protein Sequences," Science, 241: 53-57 (1988).
Rosenberg Multiple Sequence Alignment Accuracy and Evolutionary Distance Estimation, (2005) BMC Bioinformatics 6, 10 pages.
Salas et al. (2002) Archives of Biochemistry and Biophysics 403:25-34.
Sambrook et al., "Molecular Cloning: A Laboratory Manual," second edition, Cold Spring Harbor Laboratory (1989), 31 pages.
Schultz et al. "Expression and secretion in yeast of a 400-kDa envelope glycoprotein derived from Epstein-Barr virus," (1987) Gene 54 pp. 113-123.
Smith et al. "Production of Human Beta Interferon in Insect Cells Infected with a Vaculovirus Expression Vector," (1983) Mol. Cell. Biol. 3:2156-2165.
Smith et al., Single-step purification of polypeptides expressed in *Escherichia coli* as fusions with glutathione S-transferase, Gene, 67, pp. 31-40 (1988).
Stemmer "DNA shuffling by random fragmentation and reassembly: In vitro recombination for molecular evolution," (1994) Proc. Natl. Acad. Sci. U.S.A. 91:10747-10751.
Studier et al., Gene Expression Technology: Methods in Enzymology 185, Academic Press, San Diego, CA, pp. 60-89 (1990).
Stuiver et al. "Discussion: Reporting of 14C Data", (1977) Radiocarbon 19 pp. 355-363.
Suh et al. "Isoforms of acyl carrier protein involved in seed-specific fatty acids synthesis," (1999) The Plant Journal 17(6) pp. 679-688.
V. Braun "Minireviews—FhuA (TonA), the Career of a Protein," (2009) J Bacteriol. 191(11)pp. 3431-3436.
Examination Report issued on Australian Application 2017200596, dated Jan. 19, 2018.
Office Action issued on Chinese Application 20148004992.3, dated Jan. 16, 2018, English translation provided.
Office Action issued on Chinese Application 201480004992.3, dated Jul. 27, 2017.
Notice of Allowance on U.S. Appl. No. 15/621,430 dated Sep. 19, 2017.

\* cited by examiner

ACYL-ACP REDUCTASE WITH IMPROVED PROPERTIES

CROSS-REFERENCE TO RELATED APPLICATIONS

This application is a continuation of U.S. application Ser. No. 14/761,299, filed Jul. 15, 2015, which is a 371 National Stage Application of PCT/US2014/011859, filed Jan. 16, 2014, which claims the benefit of U.S. Provisional Application No. 61/753,273, filed Jan. 16, 2013, the contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Sep. 14, 2018, is named 109112-0652_SL.txt and is 161,452 bytes in size.

FIELD

The disclosure relates to acyl-ACP reductase (AAR) enzyme variants that result in improved fatty aldehyde and/or fatty alcohol production when expressed in recombinant host cells. The disclosure further relates to methods of making and using such AAR variants for the production of fatty alcohol compositions having particular characteristics.

BACKGROUND

Fatty alcohols denote an important category of industrial biochemical. For example, worldwide annual sales of fatty alcohols and their derivatives are in excess of US$1 billion. These molecules and their derivatives have numerous applications, including use as surfactants, lubricants, plasticizers, solvents, emulsifiers, emollients, thickeners, flavors, fragrances, and fuels. Due to their amphiphilic nature, fatty alcohols behave as nonionic surfactants, which are useful in personal care and household products, for example, detergents. The shorter chain fatty alcohols are used in the cosmetic and food industries as emulsifiers, emollients, and thickeners.

In nature, fatty alcohols are made by enzymes that are able to reduce various acyl-ACP or acyl-CoA molecules to the corresponding primary alcohols (e.g., U.S. Pat. Nos. 8,323,924; 8,268,599 and 8,097,439; and U.S. Patent Publication Nos. 20120282663 and 20100105963, incorporated by reference herein). However, current technologies involve mostly inorganic catalyst-mediated reduction of fatty acids to the corresponding primary alcohols. These fatty alcohols are produced via catalytic hydrogenation of fatty acids produced from natural sources, such as coconut oil, palm oil, palm kernel oil, tallow and lard, or by chemical hydration of alpha-olefins produced from petrochemical feedstocks. Fatty alcohols derived from natural sources have varying chain lengths, which are relevant and specific to particular applications. Dehydration of fatty alcohols to alpha-olefins can be accomplished by chemical catalysis.

Fatty aldehydes can be used to produce industrial specialty chemicals. For example, aldehydes are commonly used to produce polymers, resins, dyes, flavorings, plasticizers, perfumes, and pharmaceuticals. Aldehydes can also be used as solvents, preservatives, and disinfectants. Certain natural and synthetic compounds, such as vitamins and hormones, are aldehydes, and many sugars contain aldehyde groups. Fatty aldehydes can be converted to fatty alcohols by chemical or enzymatic reduction.

A greener and cleaner alternative to the production of fatty aldehydes and fatty alcohols is via fermentable sugars and/or biomass. However, in order for the production of fatty aldehydes and fatty alcohols from fermentable sugars or biomass to be commercially viable, industrial processes must be optimized for efficient conversion and recovery of the final product. The present disclosure addresses this need by providing compositions and methods for improved production of fatty aldehydes and fatty alcohols by using engineered host cells as biocatalysts.

SUMMARY

The present disclosure provides photosynthetic and heterotrophic host cells that directly produce fatty aldehydes and/or fatty alcohols of specific chain lengths such that catalytic conversion of purified fatty acids is not necessary. This biological route provides a higher quality product, a significant cost reduction and a lesser impact on the environment. More specifically, the present disclosure provides novel acyl-ACP reductase (AAR) enzyme variants that produce fatty aldehydes and/or fatty alcohols and compositions thereof. Also provided are specific AAR variant nucleic acid and protein sequences as well as novel recombinant host cells and cell cultures that encompass such engineered AAR enzyme variants. The disclosure also provides methods of using the recombinant AAR variant-expressing host cells in order to make fatty aldehyde and/or fatty alcohol compositions with particular characteristics.

One aspect of the disclosure provides variant acyl-ACP reductase (AAR) polypeptides that catalyze the conversion of an acyl-ACP to a fatty aldehyde, wherein the AAR polypeptide has at least 90% sequence identity to the corresponding wild type AAR polypeptide sequence presented as SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44, and methods for expressing the variant AAR polypeptides in a recombinant host cell resulting in a higher titer of fatty aldehyde and/or fatty alcohol composition as compared to the titer of a fatty aldehyde and/or fatty alcohol composition produced by expression of a wild type AAR polypeptide in a corresponding host cell. In one embodiment, the genetically engineered variant AAR polypeptide has at least 90% sequence identity to the corresponding wild type AAR polypeptide sequence presented as SEQ ID NO: 28 and expression of the variant AAR polypeptide in a recombinant host cell results in a higher titer of fatty aldehyde and/or fatty alcohol composition or a higher titer of C12, C14 or C16 fatty alcohols as compared to the titer produced by expression of a wild type AAR polypeptide in a corresponding host cell.

In one aspect, the variant AAR polypeptide has a mutation at one or more amino acid positions of amino acids 18, 24, 31, 34, 35, 43, 50, 63, 86, 112, 113, 116, 118, 120, 135, 148, 153, 155, 157, 159, 168, 172, 187, 188, 191, 209, 210, 211, 236, 277, 283, 285, 291, 324, 328, 335, 337 and 338 of SEQ ID NO: 28. In one preferred embodiment, the genetically engineered variant AAR polypeptide has an S18W mutation. In another preferred embodiment, the genetically engineered variant AAR polypeptide has an S18W mutation and further comprises a mutation such as M21L, D24E, D24Y, L31V, W34F, W35F, D43E, A50Q, C63A, C63G, C63Y, S86G, A112R, S113K, Q116G, R118Q, T120S, A135S, T148C, T148E, T148V, I153P, Q155C, Q155L, T157V, A159V, I168V, C172L, T187V, T188H, T188V, Q191A, L209R, E210Y, A211W, T236C, Q277V, E283G, E283S, A285V, M291V, A324T, A328S, Q335N, L337V and/or L338W.

In another aspect, the variant AAR polypeptide that has at least 90% sequence identity to the corresponding wild type AAR polypeptide sequence presented as SEQ ID NO: 34 and expression of the variant AAR polypeptide in a recombinant host cell results in a higher titer of fatty aldehyde and/or fatty alcohol or a higher titer of C12 fatty alcohol as compared to the titer produced by expression of a wild type AAR polypeptide in a corresponding host cell. The variant AAR polypeptide has a mutation at an amino acid position including amino acid 40, 52, 58, 61, 273, 303, 339, 340, 344, 345, 346 and 588 of SEQ ID NO: 34. In one preferred embodiment, the variant AAR polypeptide has a mutation at amino acid position Q40V, G52V, S58V, D61E, G273E, K303G, K339L, H340P, L344A, L344D, L344S, L344T, L345R, V346P, V346G, and/or S588V.

Another aspect of the disclosure provides a recombinant host cell that has one or more mutations as described above and wherein when the host cell is engineered to express a variant AAR polypeptide of SEQ ID NO: 28 or SEQ ID NO: 34. This recombinant host cell produces a fatty aldehyde and/or fatty alcohol composition with a titer that is at least 10% greater, at least 15% greater, at least 20% greater, at least 25% greater, or at least 30% greater than the titer of a fatty aldehyde and/or fatty alcohol composition produced by a host cell expressing the corresponding wild type AAR polypeptide, when cultured in medium containing a carbon source under conditions effective to express the variant AAR polypeptide. In one embodiment, the fatty aldehyde and or fatty alcohol composition is produced at a titer of 30 g/L to 250 g/L, e.g., a titer of at least 100 mg/L. In another embodiment, the fatty alcohol composition is produced extracellularly.

The disclosure further encompasses a cell culture that includes the recombinant host cell as described above, wherein the fatty alcohol composition includes one or more of a C6, C8, C10, C12, C13, C14, C15, C16, C17, and a C18 fatty alcohol, e.g., a C10:1, C12:1, C14:1, C16:1, or a C18:1 unsaturated fatty alcohol. In yet another embodiment, the fatty alcohol composition comprises a saturated fatty alcohol.

Another aspect of the disclosure provides a variant acyl-ACP reductase (AAR) polypeptide having at least 90% sequence identity to SEQ ID NO: 57, wherein the AAR polypeptide catalyzes the conversion of an acyl-ACP to a fatty aldehyde. In one embodiment, the expression of the variant AAR polypeptide in a recombinant host cell results in a higher titer of a fatty aldehyde or fatty alcohol composition as compared to a titer of a fatty aldehyde or fatty alcohol composition produced by expression of a wild type AAR polypeptide in a corresponding wild type host cell. In another embodiment, the expression of the variant AAR polypeptide in a recombinant host cell results in a higher titer of a fatty aldehyde or fatty alcohol composition that is a C12, C14 and/or C16 fatty alcohol composition as compared to a titer of a fatty aldehyde or fatty alcohol composition produced by expression of a wild type AAR polypeptide in a corresponding wild type host cell. In another embodiment, the variant AAR polypeptide has a mutation at amino acid position 18, wherein the mutation is S18W.

Another aspect of the disclosure provides a variant acyl-ACP reductase (AAR) polypeptide having at least 90% sequence identity to SEQ ID NO: 57, wherein the variant AAR polypeptide has another mutation at an amino acid position at amino acid 8, 16, 21, 24, 31, 34, 35, 43, 50, 63, 86, 112, 113, 116, 118, 120, 135, 148, 153, 154, 155, 157, 159, 168, 172, 187, 188, 191, 209, 210, 211, 236, 277, 281, 283, 285, 291, 324, 328, 335, 337 and/or 338. In one embodiment, the mutation is selected from L8A, D16L, M21L, D24E, D24Y, D24V, D24P, L31V, L31M, W34F, W35F, D43E, A50Q, C63A, C63G, C63Y, S86G, A112R, S113K, Q116G, R118Q, T120S, A135S, T148C, T148E, T148V, I153P, T154A, Q155C, Q155L, T157V, A159V, I168V, C172L, T187V, T188H, T188V, Q191A, L209R, E210Y, A211W, T236C, Q277V, A281L, E283G, E283S, A285V, M291V, A324T, A328S, Q335N, L337V and/or L338W. In one preferred embodiment, the variant AAR polypeptide has a M21L mutation, a C63G mutation, a S113K mutation, T154A, and an A281L mutation (SEQ ID NO: 58). In another preferred embodiment, the variant AAR polypeptide has an L8A mutation, an M21L mutation, a C63G mutation, a S113K mutation, a T154A mutation, and an A281L mutation (SEQ ID NO: 59). In another preferred embodiment, the variant AAR polypeptide has a D16L mutation, a M21L mutation, a C63G mutation, a S113K mutation, T154A, and an A281L mutation (SEQ ID NO: 60).). In another preferred embodiment, the variant AAR polypeptide has a L8A mutation, a D24V mutation, a C63G mutation, a S113K mutation, a Q155L mutation, and an A281L mutation (SEQ ID NO: 61). In another preferred embodiment, the variant AAR polypeptide has a D24P mutation, a L31M mutation, a C63G mutation, a S113K mutation, a T154A mutation, and an A281L mutation (SEQ ID NO: 62). In another preferred embodiment, the variant AAR polypeptide has a L8A mutation, a D16L mutation, a D24V mutation, a C63G mutation, a S113K mutation, a T154A mutation, and an A281L mutation (SEQ ID NO: 63). In another preferred embodiment, the variant AAR polypeptide has a D24E mutation, a C63G mutation, a S113K mutation, a T154A mutation, and an A281L mutation (SEQ ID NO: 64).

Another aspect of the present disclosure provides a recombinant host cell expressing the variant AAR polypeptides as described above (supra). In one embodiment, the recombinant host cell produces a fatty aldehyde or fatty alcohol composition with a titer that is at least 10% greater, at least 15% greater, at least 20% greater, at least 25% greater, or at least 30% greater than the titer of a fatty aldehyde or fatty alcohol composition produced by a host cell expressing a corresponding wild type AAR polypeptide, when cultured in medium containing a carbon source under conditions effective to express the variant AAR polypeptide. In one embodiment, the fatty aldehyde or fatty alcohol composition produced by the recombinant host cell is produced at a titer of about 30 g/L to about 250 g/L. In another embodiment, the fatty aldehyde or fatty alcohol composition is produced extracellularly.

The disclosure further contemplates a cell culture including the recombinant host cell expressing the variant AAR polypeptides as described above (supra). In one embodiment, the fatty alcohol composition includes a saturated and/or unsaturated fatty alcohol. In one embodiment, the cell culture includes a fatty alcohol composition that includes one or more of a C6, C8, C10, C12, C13, C14, C15, C16, C17, and a C18 fatty alcohol. In another embodiment, the fatty alcohol composition includes one or more of a C10:1, C12:1, C14:1, C16:1, and a C18:1 unsaturated fatty alcohol. In yet another embodiment, the fatty alcohol composition includes a fatty alcohol having a double bond at position 7 in the carbon chain between C7 and C8 from the reduced end of the fatty alcohol.

The disclosure further encompasses a method of producing a fatty alcohol composition having an increase in titer, including culturing the variant AAR-expressing host cell (as described above) with a carbon source; and harvesting a fatty alcohol composition. In one embodiment, the titer of the fatty alcohol is at least 20% to 30% greater than the titer of a fatty alcohol composition produced by a wild-type AAR-expressing host cell.

Another aspect of the disclosure provides a variant acyl-ACP reductase (AAR) polypeptide having at least 90% sequence identity to SEQ ID NO: 65, wherein the polypeptide catalyzes the conversion of an acyl-ACP to a fatty aldehyde. In one embodiment, the expression of the variant AAR polypeptide in a recombinant host cell results in a higher titer of a fatty aldehyde or fatty alcohol composition as compared to a titer of a fatty aldehyde or fatty alcohol composition produced by expression of a wild type AAR polypeptide in a corresponding wild type host cell. In another embodiment, the expression of the variant AAR polypeptide in a recombinant host cell results in a higher titer of a C12, C14 and/or C16 fatty alcohol composition as compared to a titer of a fatty aldehyde or fatty alcohol composition produced by expression of a wild type AAR polypeptide in a corresponding wild type host cell. In one particular aspect, the disclosure provides a variant acyl-ACP reductase (AAR) polypeptide having at least 90% sequence identity to SEQ ID NO: 65, wherein the polypeptide has a mutation at amino acid position 61. In one preferred embodiment the mutation is D61E.

The disclosure further encompasses a variant acyl-ACP reductase (AAR) polypeptide having at least 90% sequence identity to SEQ ID NO: 34, wherein expression of the variant AAR polypeptide in a recombinant host cell results in a higher titer of a fatty aldehyde or fatty alcohol composition or a higher titer of a C12, C14 and/or C16 fatty alcohol composition as compared to a titer of a fatty alcohol composition produced by expression of a wild type AAR polypeptide in a corresponding wild type host cell, and wherein the AAR polypeptide has a mutation at amino acid position 40, 52, 273, 303, 340, 344, 345, or 346. In one embodiment, the variant AAR polypeptide has a mutation selected Q40V, G52V, G273E, K303G, H340P, L344A, L344D, L344S, L344T, L345R, V346P, and V346G. In one preferred embodiment, the variant AAR polypeptide has a mutation at V346P (SEQ ID NO: 66). In another preferred embodiment, the variant AAR polypeptide has a mutation at Q40V (SEQ ID NO: 67). In another preferred embodiment, the variant AAR polypeptide has a mutation A345R (SEQ ID NO: 68). In another preferred embodiment, the variant AAR polypeptide has a mutation at L344S (SEQ ID NO: 69). In another preferred embodiment, the variant AAR polypeptide has a mutation at V346G (SEQ ID NO: 70). In another preferred embodiment, the variant AAR polypeptide has a mutation at L344D (SEQ ID NO: 71). In another preferred embodiment, the variant AAR polypeptide has a mutation at G52V (SEQ ID NO: 72). In another preferred embodiment, the variant AAR polypeptide has a mutation at L344T (SEQ ID NO: 73). In another preferred embodiment, the variant AAR polypeptide has a mutation at K303G (SEQ ID NO: 74). In another preferred embodiment, the variant AAR polypeptide has a mutation at L344A (SEQ ID NO: 75). In another preferred embodiment, the variant AAR polypeptide has a mutation at H340P (SEQ ID NO: 76). In another preferred embodiment, the variant AAR polypeptide has a mutation at G273E (SEQ ID NO: 77).

Yet another aspect of the disclosure provides a recombinant host cell expressing the variant AAR polypeptide as described above (supra). In one embodiment, the recombinant host cell produces a fatty aldehyde or fatty alcohol composition with a titer that is at least 10% greater, at least 15% greater, at least 20% greater, at least 25% greater, or at least 30% greater than the titer of a fatty aldehyde or alcohol composition produced by a host cell expressing a corresponding wild type AAR polypeptide, when cultured in medium containing a carbon source under conditions effective to express the variant AAR polypeptide. In another embodiment, the fatty alcohol composition is produced at a titer of about 30 g/L to about 250 g/L. In another embodiment, the fatty alcohol composition is produced extracellularly.

The disclosure further contemplates a cell culture with the recombinant host cell expressing the variant AAR polypeptide as described above (supra). In one embodiment, the fatty alcohol composition includes one or more of a C6, C8, C10, C12, C13, C14, C15, C16, C17, and a C18 fatty alcohol. In another embodiment, the fatty alcohol composition includes an unsaturated or saturated fatty alcohol. In another embodiment, the fatty alcohol composition includes one or more of a C10:1, C12:1, C14:1, C16:1, and a C18:1 unsaturated fatty alcohol. In another embodiment, the fatty alcohol composition includes a fatty alcohol having a double bond at position 7 in the carbon chain between C7 and C8 from the reduced end of the fatty alcohol.

Another aspect of the disclosure provides a method of producing a fatty alcohol composition having an increase in titer, including culturing the host cell expressing the AAR (as described above) with a carbon source; and harvesting a fatty alcohol composition. In one embodiment, the fatty alcohol is at least 20% to 30% greater than the titer of a fatty alcohol composition produced by a wild-type AAR-expressing host cell.

BRIEF DESCRIPTION OF THE DRAWINGS

The present disclosure is best understood when read in conjunction with the accompanying figures, which serve to illustrate the preferred embodiments. It is understood, however, that the disclosure is not limited to the specific embodiments disclosed in the figures.

DETAILED DESCRIPTION

General Overview

Figure 1:
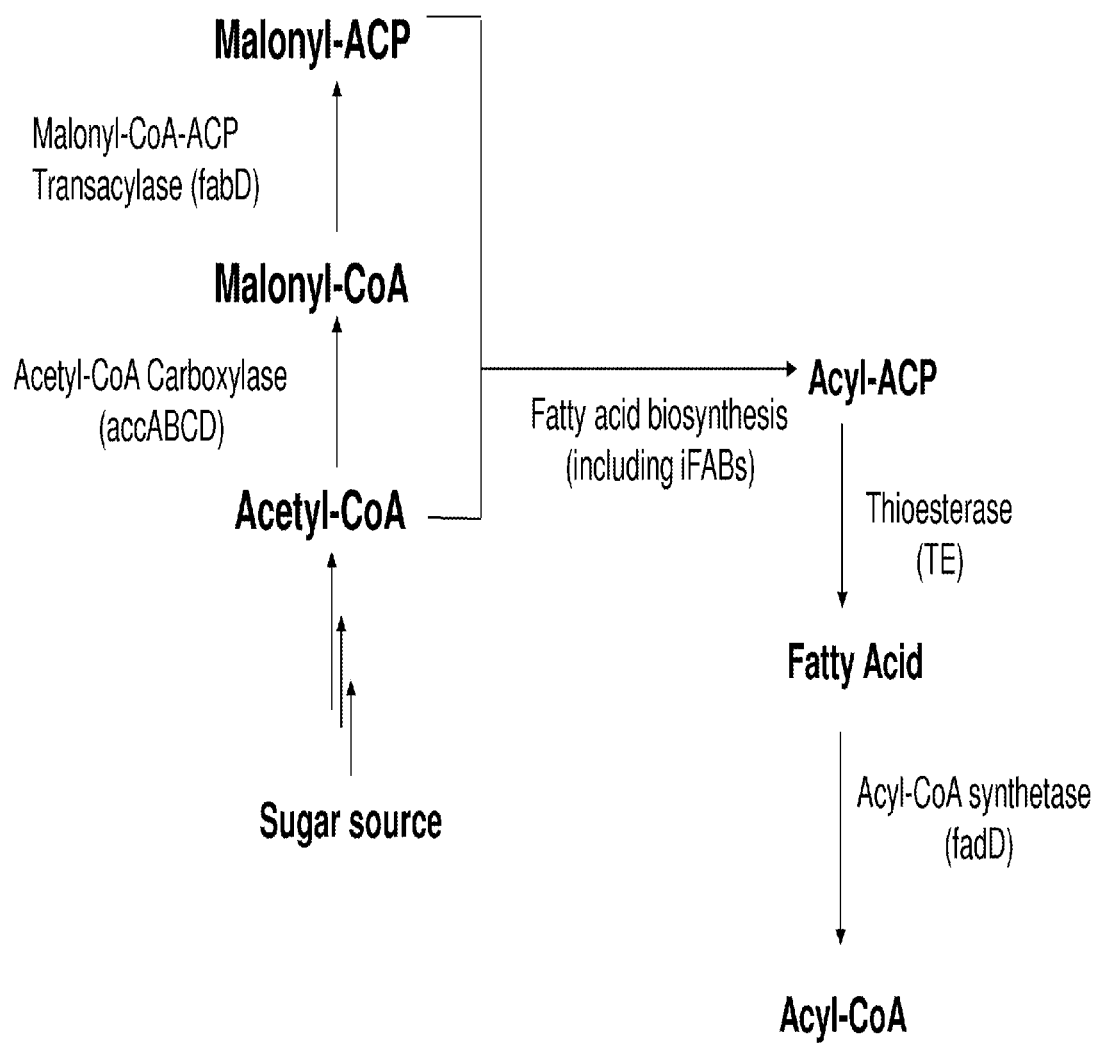
FIG. 1 is a schematic overview of an exemplary biosynthetic pathway for use in production of acyl-CoA as a precursor to fatty acid derivatives in a recombinant host cell. The cycle is initiated by condensation of malonyl-ACP and acetyl-CoA.

One way of eliminating our dependency on petrochemicals is to produce fatty acid derivatives such as fatty aldehydes and fatty alcohols through environmentally friendly microorganisms that serve as miniature production hosts. Such cellular hosts (i.e., recombinant host cells or production strains) have been engineered to produce fatty aldehydes and/or fatty alcohols from renewable sources such as renewable feedstock (e.g., fermentable sugars, carbohydrates, biomass, cellulose, glycerol, CO, $CO_2$, etc.). These fatty aldehydes and fatty alcohols are the raw materials for many industrial products including detergents and fuels.

The present disclosure relates to acyl-ACP reductase (AAR) enzyme variants that result in improved titer, yield and/or productivity of fatty aldehyde and/or fatty alcohol compositions when expressed in recombinant host cells. Herein, enhanced fatty aldehyde and/or fatty alcohol biosynthesis is accomplished by transforming host cells such that they express a variant acyl-ACP reductase (AAR) protein, which catalyzes the reaction of an acyl-ACP to a fatty aldehyde and/or a fatty alcohol. The disclosure further relates to the recombinant host cells or production strains that express the AAR enzyme variants.

Definitions

As used in this specification and the appended claims, the singular forms "a," "an" and "the" include plural referents unless the context clearly dictates otherwise. Thus, for example, reference to "a host cell" includes two or more such host cells, reference to "a fatty ester" includes one or more fatty esters, or mixtures of esters, reference to "a nucleic acid sequence" includes one or more nucleic acid sequences, reference to "an enzyme" includes one or more enzymes, and the like.

Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction they catalyze. For example, the acyl-ACP reductase (AAR) enzymatic activity is classified under E.C. 1.2.1.80 (also known as long-chain acyl-[acyl-carrier-protein] reductase) or EC 1.2.1.42. The functionality of AAR is conserved in most prokaryotes from one species to the next. Thus, different microbial species can carry out the same AAR enzymatic activity that is classified under E.C. 1.2.1.80 or EC 1.2.1.42.

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

The term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide. Similarly, the terms "recombinant polynucleotide" or "recombinant nucleic acid" or "recombinant DNA" are produced by recombinant techniques that are known to those of skill in the art.

As used herein, the terms "homolog," and "homologous" refer to a polynucleotide or a polypeptide comprising a sequence that is at least about 50 percent (%) identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably. One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In one preferred embodiment, the length of a first sequence that is aligned for comparison purposes is at least about 30%, preferably at least about 40%, more preferably at least about 50%, even more preferably at least about 60%, and even more preferably at least about 70%, at least about 80%, at least about 85%, at least about 90%, at least about 95%, at least about 98%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences. The comparison of sequences and determination of percent homology between two sequences can be accomplished using a mathematical algorithm, such as BLAST (Altschul et al. (1990) *J. Mol. Biol.* 215(3):403-410). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) *J. Mol. Biol.* 48:444-453). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) *BMC Bioinformatics* 6:278; Altschul et al. (2005) *FEBS J.* 272(20):5101-5109).

The term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and non-aqueous methods are described in that reference and either method can be used. Specific hybridization conditions referred to herein are as follows: (1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions—6×SSC at about 45° C., followed by one or more washes in 0.2×SSC, 0.1% SDS at 60° C.; (3) high stringency hybridization conditions—6× SSC at about 45° C., followed by one or more washes in 0.2.×SSC, 0.1% SDS at 65° C.; and (4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

An "endogenous" polypeptide refers to a polypeptide encoded by the genome of the parental cell (or host cell). An "exogenous" polypeptide refers to a polypeptide which is not encoded by the genome of the parental cell. A variant or mutant polypeptide is an example of an exogenous polypeptide. Thus, a non-naturally-occurring nucleic acid molecule is considered to be exogenous to a cell once introduced into the cell. A nucleic acid molecule that is naturally-occurring can also be exogenous to a particular cell. For example, an entire coding sequence isolated from cell X is an exogenous nucleic acid with respect to cell Y once that coding sequence is introduced into cell Y, even if X and Y are the same cell type.

The term "overexpressed" means that a gene is caused to be transcribed at an elevated rate compared to the endogenous transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

The term "heterologous" means derived from a different organism, different cell type, or different species. As used herein it refers to a nucleotide-, polynucleotide-, polypeptide- or protein sequence, not naturally present in a given organism. For example, a polynucleotide sequence that is native to cyanobacteria can be introduced into a host cell of *E. coli* by recombinant methods, and the polynucleotide from cyanobacteria is then heterologous to the *E. coli* cell (e.g., recombinant cell). The term "heterologous" may also be used with reference to a nucleotide-, polynucleotide-, polypeptide-, or protein sequence which is present in a recombinant host cell in a non-native state. For example, a "heterologous" nucleotide, polynucleotide, polypeptide or protein sequence may be modified relative to the wild type sequence naturally present in the corresponding wild type host cell, e.g., a modification in the level of expression or in the sequence of a nucleotide, polynucleotide, polypeptide or protein.

As used herein, the term "fragment" of a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

A "mutation", as used herein, refers to a permanent change in a nucleic acid position of a gene or in an amino acid position of a polypeptide or protein. Mutations include substitutions, additions, insertions, and deletions. For example, a mutation in an amino acid position can be a substitution of one type of amino acid with another type of amino acid (e.g., a serine (S) may be substituted with an alanine (A); a lysine (L) may be substituted with an T (Threonine); etc.). As such, a polypeptide or a protein can have one or more mutations wherein one amino acid is substituted with another amino acid.

The terms "acyl-ACP reductase (AAR) variant" and "variant acyl-ACP reductase (AAR)" are used interchangeably herein and mean an AAR related polypeptide or protein that has one or more mutations in its amino acid sequence. The AAR refers to an enzyme that catalyzes the reduction of an acyl-ACP to a fatty aldehyde and/or a fatty alcohol. The AAR variant may encompass a mutation in one or more amino acid of its polypeptide sequence. When a cell has been transformed with an AAR variant it is a cell that expresses the AAR variant (e.g., a recombinant cell). In one embodiment, the titer and/or yield of a fatty alcohol produced by a cell that expresses the AAR variant is at least twice that of a corresponding wild type cell (i.e., a corresponding cell that does not express the AAR variant). In a heterologous host such as *Escherichia coli*, fatty aldehydes may be converted to fatty alcohols by endogenous alcohol dehydrogenases. In another embodiment, the titer and/or yield of a fatty alcohol produced by a cell that expresses the AAR variant is at least about 1 times, at least about 2 times, at least about 3 times, at least about 4 times, at least about 5 times, at least about 6 times, at least about 7 times, at least about 8 times, at least about 9 times, or at least about 10 times greater than that of a corresponding wild type cell. In one embodiment, the titer and/or yield of a fatty alcohol produced by a cell expressing the AAR variant is at least about 1 percent, at least about 2 percent, at least about 3 percent, at least about 4 percent, at least about 5 percent, at least about 6 percent, at least about 7 percent, at least about 8 percent, at least about 9 percent, or about 10 percent greater than that of a corresponding wild type cell. In another embodiment, the titer and/or yield of fatty alcohols produced in a recombinant cell due to the expression of an AAR variant is at least about 20 percent to at least about 100 percent greater than that of a wild type cell. In a particular embodiments, the titer and/or yield of a fatty alcohol produced by a cell is at least about 20 percent, at least about 25 percent, at least about 30 percent, at least about 35 percent, at least about 40 percent, at least about 45 percent at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, at least about 97 percent, at least about 98 percent, or at least about 100 percent greater than that of the corresponding wild type cell.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al. (1987) *Science* 236:1237-1245). Exemplary expression control sequences are described in, for example, Goeddel, Gene Expression Technology: Methods in Enzymology, Vol. 185, Academic Press, San Diego, Calif. (1990). In the methods of the disclosure, an expression control sequence is operably linked to a polynucleotide sequence. By "operably linked" is meant that a polynucleotide sequence and an expression control sequence are connected in such a way as to permit gene expression when the appropriate molecules (e.g., transcriptional activator proteins) are bound to the expression control sequence. Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. Other useful expression vectors are provided in linear form. Also included are such other forms of expression vectors that serve equivalent functions and that have become known in the art subsequently hereto. In some embodiments, a recombinant vector further includes a promoter operably linked to the polynucleotide sequence. In some embodiments, the promoter is a developmentally-regulated promoter, an organelle-specific promoter, a tissue-specific promoter, an inducible promoter, a constitutive promoter, or a cell-specific promoter. The recombinant vector typically comprises at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors as used herein include a particular polynucleotide sequence as described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, E. coli, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes, including to increase expression of the recombinant polypeptide; to increase the solubility of the recombinant polypeptide; and to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. In certain embodiments, a polynucleotide sequence of the disclosure is operably linked to a promoter derived from bacteriophage T5.

In certain embodiments, the host cell is a yeast cell, and the expression vector is a yeast expression vector. Examples of vectors for expression in yeast *S. cerevisiae* include pYepSec1 (Baldari et al. (1987) *EMBO J.* 6:229-234); pMFa (Kurjan et al. (1982) *Cell* 30:933-943); pJRY88 (Schultz et al. (1987) *Gene* 54: 113-123); pYES2 (Invitrogen Corp., San Diego, Calif.), and picZ (Invitrogen Corp., San Diego, Calif.). In other embodiments, the host cell is an insect cell, and the expression vector is a baculovirus expression vector. Baculovirus vectors available for expression of proteins in cultured insect cells (e.g., Sf9 cells) include, for example, the pAc series (Smith et al. (1983) *Mol. Cell Biol.* 3:2156-2165) and the pVL series (Lucklow et al. (1989) *Virology* 170:31-39). In yet another embodiment, the polynucleotide sequences described herein can be expressed in mammalian cells using a mammalian expression vector. Other suitable expression systems for both prokaryotic and eukaryotic cells are well known in the art; see, e.g., Sambrook et al., "Molecular Cloning: A Laboratory Manual," second edition, Cold Spring Harbor Laboratory, (1989).

As used herein, the term "CoA" or "acyl-CoA" refers to an acyl thioester formed between the carbonyl carbon of alkyl chain and the sulfhydryl group of the 4'-phosphopantethionyl moiety of coenzyme A (CoA), which has the formula R—C(O)S-CoA, where R is any alkyl group having at least 4 carbon atoms.

The term "ACP" means acyl carrier protein. ACP is a highly conserved carrier of acyl intermediates during fatty acid biosynthesis, wherein the growing chain is bound during synthesis as a thiol ester at the distal thiol of a 4'-phosphopantetheine moiety. The protein exists in two forms, i.e., apo-ACP (inactive in fatty acid biosynthesis) and ACP or holo-ACP (active in fatty acid biosynthesis). The terms "ACP" and "holo-ACP" are used interchangeably herein and refer to the active form of the protein. An enzyme called a phosphopantetheinyltransferase is involved in the conversion of the inactive apo-ACP to the active holo-ACP. More specifically, ACP is expressed in the inactive apo-ACP form and a 4'-phosphopantetheine moiety must be post-translationally attached to a conserved serine residue on the ACP by the action of holo-acyl carrier protein synthase (ACPS), a phosphopantetheinyltransferase, in order to produce holo-ACP.

As used herein, the term "acyl-ACP" refers to an acyl thioester formed between the carbonyl carbon of an alkyl chain and the sulfhydryl group of the phosphopantetheinyl moiety of an acyl carrier protein (ACP). In some embodiments an ACP is an intermediate in the synthesis of fully saturated acyl-ACPs. In other embodiments an ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons.

As used herein, the term "fatty acid derivative" means a "fatty acid" or a "fatty acid derivative", which may be referred to as a "fatty acid or derivative thereof". The term "fatty acid" means a carboxylic acid having the formula RCOOH. R represents an aliphatic group, preferably an alkyl group. R can include between about 4 and about 22 carbon atoms. Fatty acids can be saturated, monounsaturated, or polyunsaturated. A "fatty acid derivative" is a product made in part from the fatty acid biosynthetic pathway of the production host organism. "Fatty acid derivatives" includes products made in part from ACP, acyl-ACP or acyl-ACP derivatives. Exemplary fatty acid derivatives include, for example, acyl-CoA, fatty acids, fatty aldehydes, short and long chain alcohols, fatty alcohols, hydrocarbons, esters (e.g., waxes, fatty acid esters, or fatty esters), terminal olefins, internal olefins, and ketones.

As used herein, the term "fatty acid biosynthetic pathway" means a biosynthetic pathway that produces fatty acids and derivatives thereof. The fatty acid biosynthetic pathway may include additional enzymes to produce fatty acids derivatives having desired characteristics.

As used herein, "fatty aldehyde" means an aldehyde having the formula RCHO characterized by a carbonyl group (C=O). In some embodiments, the fatty aldehyde is any aldehyde made from a fatty alcohol. In certain embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty aldehyde is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty aldehyde. In certain embodiments, the fatty aldehyde is a $C_6$, $C_8$, $C_{10}$, $C_{12}$, $C_{13}$, $C_{14}$, $C_{15}$, $C_{16}$, $C_{17}$, or $C_{18}$ fatty aldehyde.

As used herein, "fatty alcohol" means an alcohol having the formula ROH. In some embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty alcohol is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty alcohol. In certain embodiments, the fatty alcohol is a $C_6$, $C_8$, $C_{10}$, $C_{12}$, $C_{13}$, $C_{14}$, $C_{15}$, $C_{16}$, $C_{17}$, or $C_{18}$ fatty alcohol.

A "fatty alcohol composition" as referred to herein is produced by a recombinant host cell and typically comprises a mixture of fatty alcohols. In some cases, the mixture includes more than one type of product (e.g., fatty alcohols and fatty acids). In other cases, the fatty acid derivative compositions may comprise, for example, a mixture of fatty alcohols with various chain lengths and saturation or branching characteristics. In still other cases, the fatty alcohol composition comprises a mixture of both more than one type of product and products with various chain lengths and saturation or branching characteristics.

A host cell engineered to produce a fatty aldehyde will typically convert some of the fatty aldehyde to a fatty alcohol. In one exemplary embodiment, acyl-ACP is converted to a fatty aldehyde via the action of AAR. Conversion of fatty aldehydes to fatty alcohols can be further facilitated, for example, via a fatty alcohol biosynthetic polypeptide. In some embodiments, a gene encoding a fatty alcohol biosynthetic polypeptide is expressed or overexpressed in the host cell. In certain embodiments, the fatty alcohol biosynthetic polypeptide has aldehyde reductase or alcohol dehydrogenase activity.

Examples of alcohol dehydrogenase polypeptides useful in accordance with the disclosure include, but are not limited to AlrA of *Acinetobacter* sp. M-1 (SEQ ID NO: 52) or AlrA homologs, such as AlrAadp1 (SEQ ID NO:53) and endogenous *E. coli* alcohol dehydrogenases such as YjgB, (AAC77226), DkgA (NP_417485), DkgB (NP_414743), YdjL (AAC74846), YdjJ (NP_416288), AdhP (NP_415995), YhdH (NP_417719), YahK (NP_414859), YphC (AAC75598), YqhD (446856) and YbbO [AAC73595.1]. Additional examples are described in International Patent Application Publication Nos. WO 2007/136762, WO2008/119082 and WO 2010/062480. In certain embodiments, the fatty alcohol biosynthetic polypeptide has aldehyde reductase or alcohol dehydrogenase activity (EC 1.1.1.1).

The R group of a fatty acid, fatty aldehyde, or fatty alcohol can be a straight chain or a branched chain. Branched chains may have more than one point of branching and may include cyclic branches. In some embodiments, the branched fatty acid, branched fatty aldehyde, or branched fatty alcohol is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ branched fatty acid, branched fatty aldehyde, or branched fatty alcohol. In particular embodiments, the branched fatty acid, branched fatty aldehyde, or branched fatty alcohol is a $C_6$, $C_8$, $C_{10}$, $C_{12}$, $C_{13}$, $C_{14}$, $C_{15}$, $C_{16}$, $C_{17}$, or $C_{18}$ branched fatty acid, branched fatty aldehyde, or branched fatty alcohol. In certain embodiments, the hydroxyl group of the branched fatty acid, branched fatty aldehyde, or branched fatty alcohol is in the primary ($C_1$) position.

In certain embodiments, the branched fatty acid, branched fatty aldehyde, or branched fatty alcohol is an iso-fatty acid, iso-fatty aldehyde, or iso-fatty alcohol, or an anteiso-fatty acid, an anteiso-fatty aldehyde, or anteiso-fatty alcohol. In exemplary embodiments, the branched fatty acid, branched fatty aldehyde, or branched fatty alcohol is selected from iso-$C_{7:0}$, iso-$C_{8:0}$, iso-$C_{9:0}$, iso-$C_{10:0}$, iso-$C_{11:0}$, iso-$C_{12:0}$, iso-$C_{13:0}$, iso-$C_{14:0}$, iso-$C_{15:0}$, iso-$C_{16:0}$, iso-$C_{17:0}$, iso-$C_{18:0}$, iso-$C_{19:0}$, anteiso-$C_{7:0}$, anteiso-$C_{8:0}$, anteiso-$C_{9:0}$, anteiso-$C_{10:0}$, anteiso-$C_{11:0}$, anteiso-$C_{12:0}$, anteiso-$C_{13:0}$, anteiso-$C_{14:0}$, anteiso-$C_{15:0}$, anteiso-$C_{16:0}$, anteiso-$C_{17:0}$, anteiso-$C_{18:0}$, and anteiso-$C_{19:0}$ branched fatty acid, branched fatty aldehyde or branched fatty alcohol.

The R group of a branched or unbranched fatty acid, branched or unbranched fatty aldehyde, or branched or unbranched fatty alcohol can be saturated or unsaturated. If unsaturated, the R group can have one or more than one point of unsaturation. In some embodiments, the unsaturated fatty acid, unsaturated fatty aldehyde, or unsaturated fatty alcohol is a monounsaturated fatty acid, monounsaturated fatty aldehyde, or monounsaturated fatty alcohol. In certain embodiments, the unsaturated fatty acid, unsaturated fatty aldehyde, or unsaturated fatty alcohol is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated fatty acid, unsaturated fatty aldehyde, or unsaturated fatty alcohol. In certain preferred embodiments, the unsaturated fatty acid, unsaturated fatty aldehyde, or unsaturated fatty alcohol is C10:1, C12:1, C14:1, C16:1, or C18:1. In yet other embodiments, the unsaturated fatty acid, unsaturated fatty aldehyde, or unsaturated fatty alcohol is unsaturated at the omega-7 position. In certain embodiments, the unsaturated fatty acid, unsaturated fatty aldehyde, or unsaturated fatty alcohol comprises a cis double bond.

As used herein, a "recombinant host cell" or "engineered host cell" is a host cell, e.g., a microorganism that has been modified such that it produces fatty alcohols. In some embodiments, the recombinant host cell comprises one or more polynucleotides, each polynucleotide encoding a polypeptide having fatty aldehyde and/or fatty alcohol biosynthetic enzyme activity, wherein the recombinant host cell produces a fatty alcohol composition when cultured in the presence of a carbon source under conditions effective to express the polynucleotides.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typically refers to a liquid media comprising viable cells. In one embodiment, a culture comprises cells reproducing in a predetermined culture media under controlled conditions, for example, a culture of recombinant host cells grown in liquid media comprising a selected carbon source and/or nitrogen.

The terms "culturing" or "cultivation" refers to growing a population of cells (e.g., microbial cells) under suitable conditions in a liquid or solid medium. In particular embodiments, culturing refers to the fermentative bioconversion of a substrate to an end-product. Culturing media are well known and individual components of such culture media are available from commercial sources, e.g., under the DIFCO media and BBL media. In one non-limiting example, the aqueous nutrient medium is a "rich medium" comprising complex sources of nitrogen, salts, and carbon, such as YP medium, comprising 10 g/L of peptone and 10 g/L yeast extract of such a medium.

The host cell can be additionally engineered to assimilate carbon efficiently and use cellulosic materials as carbon sources according to methods described, for example, in U.S. Pat. Nos. 5,000,000; 5,028,539; 5,424,202; 5,482,846; 5,602,030 and WO2010127318. In addition, the host cell can be engineered to express an invertase so that sucrose can be used as a carbon source.

As used herein, the term "under conditions effective to express said heterologous nucleotide sequences" means any conditions that allow a host cell to produce a desired fatty aldehyde or fatty alcohol. Suitable conditions include, for example, fermentation conditions.

As used herein, "modified" or an "altered level of" activity of a protein, for example an enzyme, in a recombinant host cell refers to a difference in one or more characteristics in the activity determined relative to the parent or native host cell. Typically differences in activity are determined between a recombinant host cell, having modified activity, and the corresponding wild-type host cell (e.g., comparison of a culture of a recombinant host cell relative to wild-type host cell). Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein. In certain instances, the coding sequence for the polypeptides as described herein are codon optimized for expression in a particular host cell. For example, for expression in E. coli, one or more codons can be optimized (Grosjean et al. (1982) Gene 18:199-209).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

As used herein, the phrase "the expression of said nucleotide sequence is modified relative to the wild type nucleotide sequence," means an increase or decrease in the level of expression and/or activity of an endogenous nucleotide sequence or the expression and/or activity of a heterologous or non-native polypeptide-encoding nucleotide sequence.

As used herein, the term "express" with respect to a polynucleotide is to cause it to function. A polynucleotide which encodes a polypeptide (or protein) will, when expressed, be transcribed and translated to produce that polypeptide (or protein). As used herein, the term "overexpress" means to express (or cause to express) a polynucleotide or polypeptide in a cell at a greater concentration than is normally expressed in a corresponding wild-type cell under the same conditions.

The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions.

As used herein, the term "titer" refers to the quantity of fatty aldehyde or fatty alcohol produced per unit volume of host cell culture. In any aspect of the compositions and methods described herein, a fatty alcohol is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty aldehyde or fatty alcohol is produced at a titer of more than 100 g/L, more than 200 g/L, more than 300 g/L, or higher, such as 500 g/L, 700 g/L, 1000 g/L, 1200 g/L, 1500 g/L, or 2000 g/L. The preferred titer of fatty aldehyde or fatty alcohol produced by a recombinant host cell according to the methods of the disclosure is from 5 g/L to 200 g/L, 10 g/L to 150 g/L, 20 g/L to 120 g/L and 30 g/L to 100 g/L.

As used herein, the term "yield of the fatty aldehyde or fatty alcohol produced by a host cell" refers to the efficiency by which an input carbon source is converted to product (i.e., fatty alcohol or fatty aldehyde) in a host cell. Host cells engineered to produce fatty alcohols and/or fatty aldehydes according to the methods of the disclosure have a yield of at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% or a range bounded by any two of the foregoing values. In other embodiments, a fatty aldehyde or fatty alcohol is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of the fatty alcohol or fatty aldehyde produced by the recombinant host cell according to the methods of the disclosure can be 5% to 15%, 10% to 25%, 10% to 22%, 15% to 27%, 18% to 22%, 20% to 28%, or 20% to 30%. The preferred yield of fatty alcohol produced by the recombinant host cell according to the methods of the disclosure is from 10% to 30%.

As used herein, the term "productivity" refers to the quantity of fatty aldehyde or fatty alcohol produced per unit volume of host cell culture per unit time. In any aspect of the compositions and methods described herein, the productivity of fatty aldehyde or fatty alcohol produced by a recombinant host cell is at least 100 mg/L/hour, at least 200 mg/L/hour$_0$, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. Alternatively, or in addition, the productivity is 2500 mg/L/hour or less, 2000 mg/L/OD$_{600}$ or less, 1500 mg/L/OD$_{600}$ or less, 120 mg/L/hour, or less, 1000 mg/L/hour or less, 800 mg/L/hour, or less, or 600 mg/L/hour or less. Thus, the productivity can be bounded by any two of the above endpoints. For example, the productivity can be 3 to 30 mg/L/hour, 6 to 20 mg/L/hour, or 15 to 30 mg/L/hour. The preferred productivity of a fatty aldehyde or fatty alcohol produced by a recombinant host cell according to the methods of the disclosure is selected from 500 mg/L/hour to 2500 mg/L/hour, or from 700 mg/L/hour to 2000 mg/L/hour.

The terms "total fatty species" and "total fatty acid product" may be used interchangeably herein with reference to the total amount of fatty alcohols, fatty aldehydes, free fatty acids, and fatty esters present in a sample as evaluated by GC-FID as described in International Patent Application Publication WO 2008/119082. Samples may contain one, two, three, or four of these compounds depending on the context.

As used herein, the term "glucose utilization rate" means the amount of glucose used by the culture per unit time, reported as grams/liter/hour (g/L/hr).

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain embodiments, the carbon source is gas mixture containing CO coming from flu gas. In another embodiment, the carbon source is a gas mixture containing CO coming from the reformation of a carbon containing material, such as biomass, coal, or natural gas. In other embodiments the carbon source is syngas, methane, or natural gas. In certain preferred embodiments, the carbon source is biomass. In other preferred embodiments, the carbon source is glucose. In other preferred embodiments the carbon source is sucrose. In other embodiments the carbon source is glycerol. In other preferred embodiments the carbon source is sugar cane juice, sugar cane syrup, or corn syrup. In other preferred embodiments, the carbon source is derived from renewable feedstocks, such as $CO_2$, CO, glucose, sucrose, xylose, arabinose, glycerol, mannose, or mixtures thereof. In other embodiments, the carbon source is derived from renewable feedstocks including starches, cellulosic biomass, molasses, and other sources of carbohydrates including carbohydrate mixtures derived from hydrolysis of cellulosic biomass, or the waste materials derived from plant- or natural oil processing.

As used herein, the term "biomass" refers to any biological material from which a carbon source is derived. In some embodiments, a biomass is processed into a carbon source, which is suitable for bioconversion. In other embodiments, the biomass does not require further processing into a carbon source. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, glycerol, fermentation waste, ensilage, straw, lumber, sewage, garbage, cellulosic urban waste, and food leftovers (e.g., soaps, oils and fatty acids). The term "biomass" also can refer to sources of carbon, such as carbohydrates (e.g., monosaccharides, disaccharides, or polysaccharides).

As used herein, the term "isolated," with respect to products (such as fatty acids and derivatives thereof) refers to products that are separated from cellular components, cell culture media, or chemical or synthetic precursors. The fatty acids and derivatives thereof produced by the methods described herein can be relatively immiscible in the fermentation broth, as well as in the cytoplasm. Therefore, the fatty acids and derivatives thereof can collect in an organic phase either intracellularly or extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of fatty acid derivatives such as fatty alcohols in a sample. For example, when a fatty acid derivative is produced in a recombinant host cell, the fatty acid derivative can be purified by the removal of host cell proteins or other host cell materials. After purification, the percentage of fatty acid derivative in the sample is increased. The terms "purify", "purified," and "purification" are relative terms which do not require absolute purity. Thus, for example, when a fatty acid derivative is produced in recombinant host cells, a purified fatty acid derivative is a fatty acid derivative that is substantially separated from other cellular components (e.g., nucleic acids, polypeptides, lipids, carbohydrates, or other hydrocarbons).

Increased Fatty Alcohol Production

The disclosure provides for the production of a fatty alcohol composition that is enhanced as a result of the modified expression of an acyl-ACP reductase (AAR) gene in a host cell. AAR is involved in a biosynthetic pathway for the production of fatty aldehydes and fatty alcohols. Variant AAR is used alone or in combination with the modified expression of another gene involved in the biosynthetic pathway that converts a fatty aldehyde to a fatty alcohol. Herein, the disclosure provides recombinant host cells, which have been engineered to express a variant AAR to provide enhanced fatty alcohol biosynthesis relative to non-engineered or native or wild type host cells that express wild type AAR or other fatty alcohol biosynthetic polypeptides with the same function as AAR. The disclosure identifies AAR related polynucleotides and polypeptides useful in the recombinant host cells. However, it will be recognized that absolute sequence identity to AAR related polynucleotides is not necessary. For example, changes in a particular polynucleotide sequence can be made and the encoded polypeptide screened for activity. Such changes typically include conservative mutations and silent mutations such as, for example, through codon optimization. Modified or mutated (i.e., mutant) polynucleotides and encoded variant polypeptides can be screened for a desired function, such as, an improved function compared to the parent polypeptide, including but not limited to increased catalytic activity, increased stability, or decreased inhibition (e.g., decreased feedback inhibition), using methods known in the art. The disclosure identifies enzymatic activities involved in various steps (i.e., reactions) of the fatty acid biosynthetic pathways described herein according to Enzyme Classification (EC) number, and provides exemplary polypeptides (enzymes) categorized by such EC numbers, and exemplary polynucleotides encoding such polypeptides. Such exemplary polypeptides and polynucleotides, which are identified herein by Accession Numbers and/or Sequence Identifier Numbers (SEQ ID NOs), are useful for engineering fatty acid pathways in parental host cells to obtain the recombinant host cells described herein. It is to be understood, however, that polypeptides and polynucleotides described herein are exemplary and, thus, non-limiting. The sequences of homologues of exemplary polypeptides described herein are available to those of skill in the art using databases such as, for example, the Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the World Wide Web. A variety of different host cells can be modified to express variant AAR fatty alcohol biosynthetic enzymes such as those described herein, resulting in recombinant host cells suitable for the enhanced production of fatty alcohol compositions. It is understood that a variety of cells can provide sources of genetic material, including polynucleotide sequences that encode polypeptides suitable for use in a recombinant host cell as described herein.

Acyl-ACP Reductase (AAR) Polypeptides and Variants Thereof

In one aspect the disclosure relates to improved production of fatty acid derivatives such as fatty aldehydes and/or fatty alcohols by engineering a host cell to express a native or non-native acyl-ACP reductase (AAR) protein. The AAR protein catalyzes the reduction of an acyl-ACP to a fatty aldehyde and may also catalyze the conversion of a fatty aldehyde to a fatty alcohol (see U.S. Patent Publication No. 20120282663, incorporated herein by reference). The AAR polypeptide or the polynucleotide sequence that encodes the AAR polypeptide may be native (e.g., endogenous) or non-native (e.g., exogenous, heterologous, etc.), i.e., it may differ from the wild type sequence and expression thereof naturally present in the corresponding wild type host cell. Examples include a modification in the sequence of the AAR polynucleotide, polypeptide or protein resulting in a variant AAR (e.g., mutant) and/or in the level of expression thereof. The disclosure includes AAR polypeptides, homologs, and variants.

In one embodiment, an AAR polypeptide for use in practicing the disclosure has at least 90% sequence identity to the wild-type AAR polypeptide sequence of SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44. In some embodiments the AAR is derived from a *Synechococcus* species or a *Prochlorococcus* species. In other embodiments, an AAR polypeptide for use in practicing the disclosure has at least 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the wild-type AAR polypeptide sequence of SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44, and may also include one or more substitutions which results in useful characteristics and/or properties as described herein. In one embodiment, the AAR polypeptide for use in practicing the present disclosure has at least 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the wild-type AAR polypeptide sequence of SEQ ID NO: 28 or SEQ ID NO: 34. In other embodiments, an AAR polypeptide for use in practicing the disclosure has 100% sequence identity to SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44. In still other embodiments, the improved or variant AAR polypeptide sequence is derived from a species other than a *Synechococcus* species or a *Prochlorococcus* species.

In a related embodiment, the disclosure includes AAR polypeptides that have an amino acid sequence encoded by a nucleic acid sequence that has at least 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 43. In some embodiments the nucleic acid sequence encodes an AAR variant with one or more substitutions which results in improved characteristics and/or properties as described herein. In yet another related embodiment, an AAR polypeptide for use in practicing the disclosure is encoded by a nucleotide sequence having 100% sequence identity to SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 43. In another aspect, the disclosure relates to AAR polypeptides that comprise an amino acid sequence encoded by a nucleic acid that hybridizes under stringent conditions over substantially the entire length of a nucleic acid corresponding to SEQ ID NO: 27, SEQ ID NO: 29, SEQ ID NO:

31, SEQ ID NO: 33, SEQ ID NO: 35, SEQ ID NO: 37, SEQ ID NO: 39, SEQ ID NO: 41 or SEQ ID NO: 43.

In one preferred embodiment, the disclosure provides a AAR polypeptide for use in practicing the disclosure that has at least 90% sequence identity to the variant AAR polypeptide sequence of any one of SEQ ID NO: 57 through SEQ ID NO: 78. In some embodiments the variant AAR is derived from a *Synechococcus* species or a *Prochlorococcus* species. In other embodiments, an AAR polypeptide for use in practicing the disclosure has at least 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the variant AAR polypeptide sequence of any one of SEQ ID NO: 57 through SEQ ID NO: 78. The variant AAR polypeptide may include one or more substitution(s) which result in useful characteristics and/or properties as described herein. In another preferred embodiment, the AAR polypeptide for use in practicing the disclosure has at least 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the variant AAR polypeptide sequence of SEQ ID NO: 57, SEQ ID NO: 58, SEQ ID NO: 59 or SEQ ID NO: 65. In other embodiments, an AAR polypeptide for use in practicing the disclosure has 100% sequence identity to any one of SEQ ID NO: 57 through SEQ ID NO: 78. In still other embodiments, the improved or variant AAR polypeptide sequence is derived from a species other than a *Synechococcus* species or a *Prochlorococcus* species.

The inventors built an error prone library of the acyl-ACP reductase from *Synechococcus elongatus* PCC7942 (AAR_7942) in order to screen for variants that have improvements over the wild type AAR_7942 (see Example 3, infra). The improvements are classified as either improving fatty alcohol titer overall or increasing the fraction of C10, C12, C14 or C16 fatty alcohols without significantly affecting titer. The error prone library identified various amino acid positions including amino acid position 18. Saturation and combination libraries were prepared to further test these positions. SEQ ID NO: 57 codes for the amino acid sequence for an AAR variant (mutant) that has a mutation in amino acid 18. The mutation S18W where serine is replaced with tryptophan results in a significant increase of fatty alcohol production when expressed in cells (see Examples 3 and 4, infra). More specifically, the S18W mutation lead to a 227 percent increase in total fatty alcohol (FALC) production and a 324 percent increase in C14 fatty alcohols compared to wild type AAR used as control (see Tables 4A and 4B, infra).

The inventors built saturation libraries based on the S18W mutation in order to identify variants (mutants) that further increased overall FALC titer or the fraction of C12 fatty alcohols (see Example 4 and Table 5, infra). Combination libraries that used the S18W mutation (SEQ ID NO: 57) as a template produced 7 combination mutants that showed further significant increases in the total FALC titer and/or C12 fatty alcohol production (see Table 6B, infra). The 7 combination mutants include AAR with mutation S18W (SEQ ID NO: 57); AAR with mutations M21L, C63G, S113K, T154A, A281L (SEQ ID NO: 58); AAR with mutations L8A, M21L, C63G, A77A (GCC to GCA silent codon mutation), S113K, T154A, A281L (SEQ ID NO: 59); AAR with mutations D16L, M21L, C63G, S113K, T154A, A281L (SEQ ID NO: 60); AAR with mutations L8A, D24V, C63G, S113K, Q155L, A281L (SEQ ID NO: 61); AAR with mutations D24P, L31M, C63G, S113K, T154A, A281L (SEQ ID NO: 62); AAR with mutations L8A, D16L, D24V, C63G, S113K, T154A, A281L (SEQ ID NO: 63); and AAR with mutations D24E, C63G, S113K, T154A, A281L (SEQ ID NO: 64). Notably, SEQ ID NO: 58 showed the highest fraction of C12 fatty alcohols while SEQ ID NO: 59 showed the highest titer of the combination mutants (see Table 6B, infra).

Figure 10:
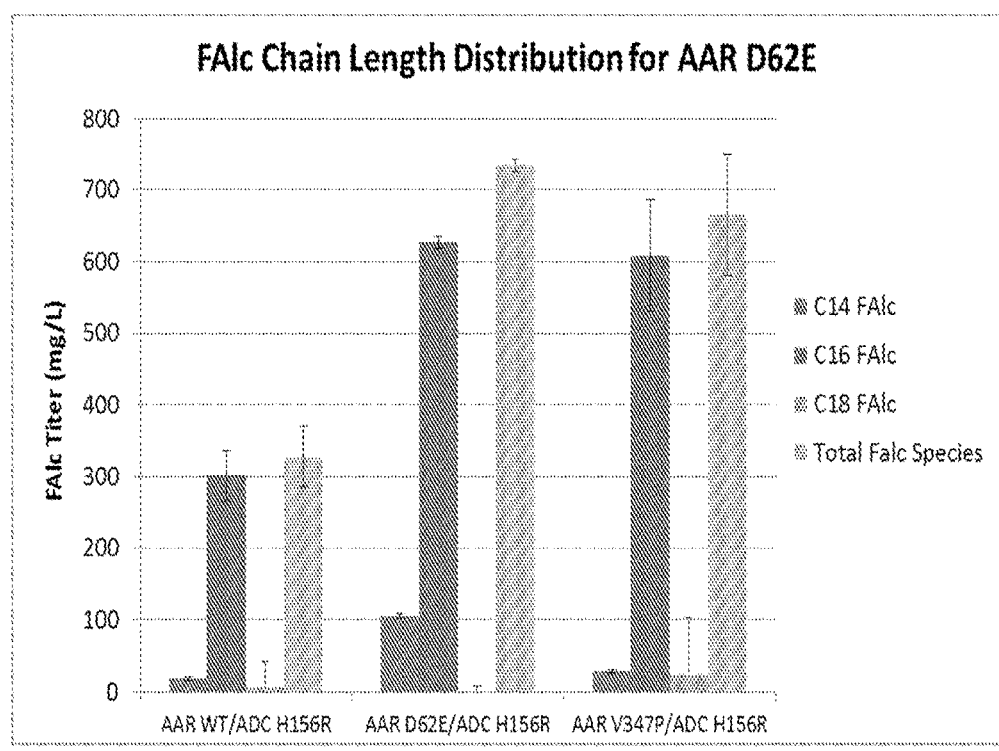
FIG. 10 presents results that illustrate a shift in chain length distribution for FALC from C16 to C14 when the D61E variant of MED4_AAR was expressed in recombinant host cells.

The inventors also built a full saturation library of the acyl-ACP reductase from *Prochlorococcus marinus* MED4_AAR in order to screen for variants that show improvements over the wild type MED4_AAR (see Example 7, infra). The AAR variants were selected based upon production of more fatty alcohols than the wild type AAR enzyme or the ability to produce fatty alcohols with an altered chain length profile, e.g., an increased fraction of C12, C14, or C16 fatty alcohols. Table 8 (see Example 7, infra) shows representative data from 16 AAR variants that produced the highest FALC titers ranging from 1.4-fold to 2.2 fold over wild type MED4_AAR. The inventors also screened for AAR variants that have an altered chain length profile, wherein an increased proportion of FALC species with a chain length shorter than C16 is of interest. Two variant clones that lead to a2-3-fold increase in the quantity of FALC are shown in FIG. 10. The expression of one of these AAR variants, i.e., the D61E mutant (SEQ ID NO: 65) in a recombinant host cell, skewed the chain length distribution of fatty alcohol species toward shorter carbon chains. All variants led to a higher quantity of FALC as they have increased titer, but only SEQ ID NO: 65 had an increased fraction of C14 (and higher titer). Table 9 (see Example 7, infra) illustrates the FALC chain length distribution produced by recombinant host cells expressing the D61E variant of MED4_AAR compared to wild type (WT) MED4_AAR and the V346P variant of MED4_AAR which did not produce products with altered chain lengths.

Acyl Carrier Protein (ACP)

Figure 2:
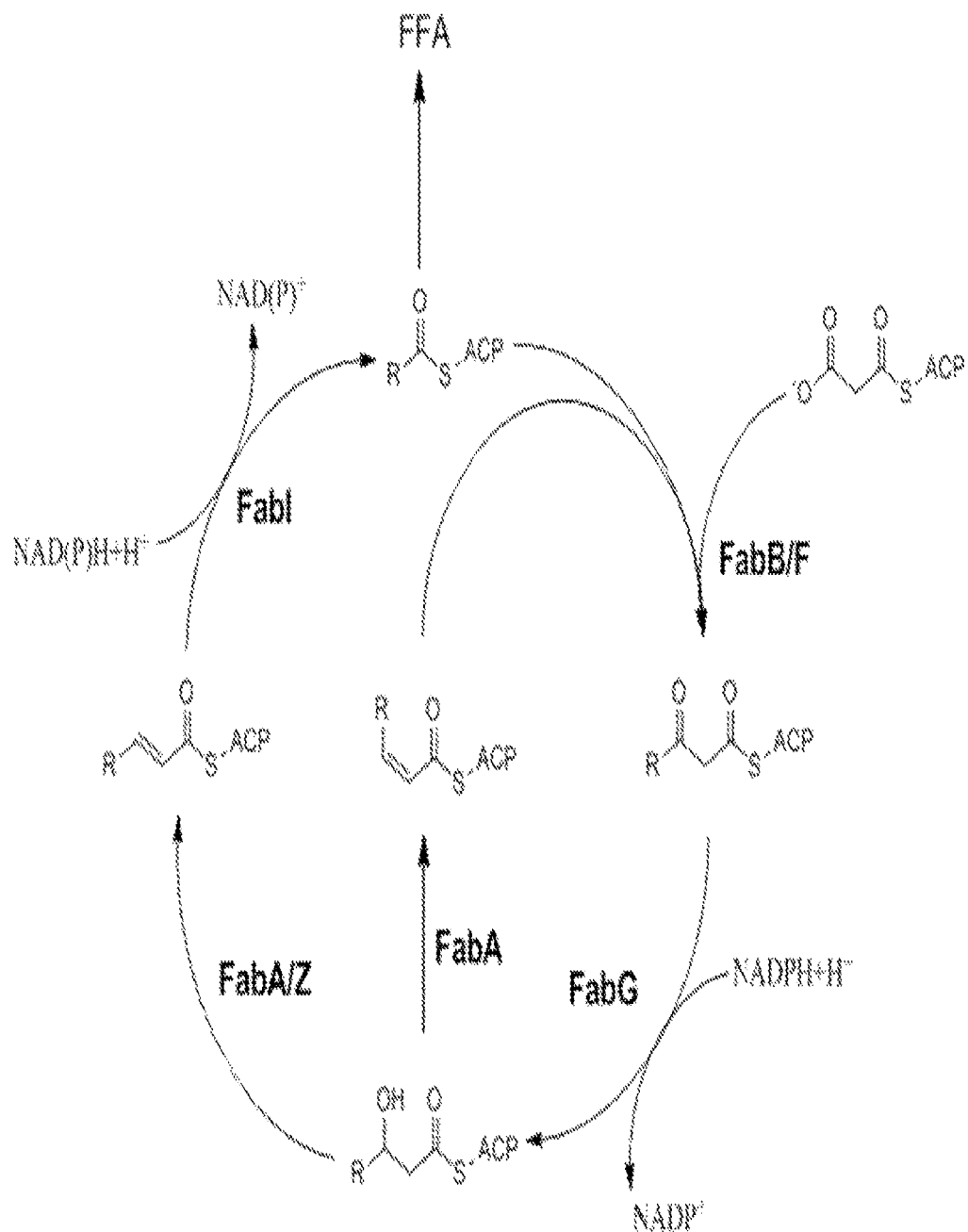
FIG. 2 is a schematic overview of an exemplary fatty acid biosynthetic cycle, wherein elongation cycles begin with the condensation of malonyl-ACP and an acyl-ACP catalyzed by β-ketoacyl-ACP synthase I (fabB) and β-ketoacyl-ACP synthase II (fabF) to produce a β-keto-acyl-ACP, then the β-keto-acyl-ACP is reduced by a NADPH-dependent β-ketoacyl-ACP reductase (fabG) to produce a β-hydroxy-acyl-ACP, which is dehydrated to a trans-2-enoyl-acyl-ACP by β-hydroxyacyl-ACP dehydratase (fabA or fabZ). FabA can also isomerize trans-2-enoyl-acyl-ACP to cis-3-enoyl-acyl-ACP, which can bypass fabI and can used by fabB (typically for up to an aliphatic chain length of C16) to produce β-keto-acyl-ACP. The final step in each cycle is catalyzed by a NADH or NADHPH-dependent enoyl-ACP reductase (fabI) that converts trans-2-enoyl-acyl-ACP to acyl-ACP. In the methods described herein, termination of fatty acid synthesis occurs by thioesterase removal of the acyl group from acyl-ACP to release free fatty acids (FFA). Thioesterases (e.g., tesA) hydrolyze thioester bonds, which occur between acyl chains and ACP through sulfhydryl bonds.
Figure 3:
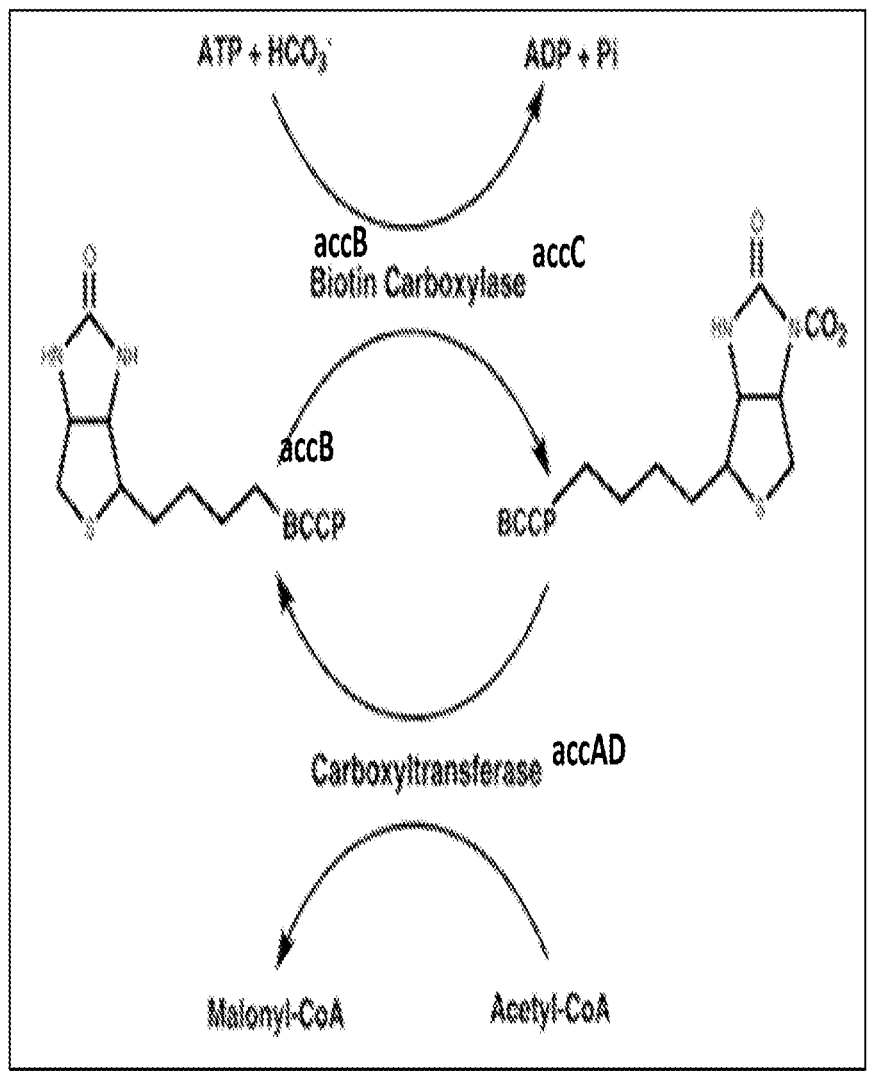
FIG. 3 illustrates the structure and function of the acetyl-CoA carboxylase (accABCD) enzyme complex. Biotin carboxylase is encoded by the accC gene, whereas biotin carboxyl carrier protein (BCCP) is encoded by the accB gene. The two subunits involved in carboxyl transferase activity are encoded by the accA and accD genes. The covalently bound biotin of BCCP carries the carboxylate moiety. The birA gene biotinylates holo-accB.

There are conflicting reports in the literature as to factors that can limit fatty acid biosynthesis in host cells, such as *Escherichia coli* (*E. coli*). Although acyl carrier proteins (ACP) are conserved to some extent in all organisms, their primary sequence can differ. It has been suggested that when terminal pathway enzymes from sources other than *E. coli* are expressed in *E. coli* in order to convert fatty acyl-ACPs to products, limitations may exist such as in the recognition, affinity and/or turnover of the recombinant pathway enzyme towards the fatty acyl-ACPs (see Suh et al. (1999) *The Plant Journal* 17(6):679-688; Salas et al. (2002) *Archives of Biochemistry and Biophysics* 403:25-34). One suggestion is that a limitation of the main precursors for fatty acid biosynthesis, for example, acetyl-CoA and malonyl-CoA can result in decreased synthesis of fatty acid derivatives. One approach to increasing the flux through fatty acid biosynthesis is to manipulate various enzymes in the pathway (see FIGS. 1-3). The supply of acyl-ACPs from acetyl-CoA via the acetyl-CoA carboxylase (acc) complex and the fatty acid biosynthetic (fab) pathway may impact the rate of fatty acid derivative production (see FIG. 2). As detailed in the Examples (infra), the effect of overexpression of ACP on production of fatty alcohols was evaluated for purpose of illustration.

A host cell that is engineered to express an ACP can exhibit an increase in the titer of a fatty aldehyde and/or fatty alcohol composition or a specific fatty aldehyde and/or fatty alcohol composition wherein the increase is at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% greater than the titer of the fatty aldehyde and/or fatty alcohol composition produced by a corresponding host cell that does not express ACP when cultured under the same conditions. In one aspect the disclosure relates to improved production of fatty aldehyde and/or fatty alcohol composition by engineering a host cell to express a native (e.g., endogenous) or non-native (e.g., exogenous, heterologous) ACP protein. The ACP polypeptide or the polynucleotide sequence that encodes the ACP polypeptide may be non-native, i.e., it may differ from the wild type sequence naturally present in the corresponding wild type host cell. Examples include, a modification in the level of expression or in the sequence of a nucleotide, polypeptide or protein. The disclosure includes ACP polypeptides and homologs thereof.

In one embodiment, an ACP polypeptide for use in practicing the disclosure has at least 70% sequence identity to SEQ ID NO: 2, SEQ ID NO: 4, SEQ ID NO: 6, SEQ ID NO: 8 or SEQ ID NO: 10. In some embodiments the ACP is derived from *Marinobacter hydrocarbonoclasticus* or *E. coli*. In other embodiments, an ACP polypeptide for use in practicing the disclosure has at least 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the wild-type ACP polypeptide sequence of SEQ ID NO: 2, SEQ ID NO: 4, SEQ ID NO: 6, SEQ ID NO: 8 or SEQ ID NO: 10, and may also include one or more substitutions which results in useful characteristics and/or properties as described herein. In one aspect, an ACP polypeptide for use in practicing the disclosure has 100% sequence identity to SEQ ID NO: 2, SEQ ID NO: 4, SEQ ID NO: 6, SEQ ID NO: 8 or SEQ ID NO: 10. In other embodiments, the improved or variant ACP polypeptide sequence is derived from a species other than *M. hydrocarbonoclasticus* or *E. coli*. In a related aspect, an ACP polypeptide for use in practicing the disclosure is encoded by a nucleotide sequence having 100% sequence identity to SEQ ID NO: 1, SEQ ID NO: 3, SEQ ID NO: 5, SEQ ID NO: 7, or SEQ ID NO: 9. In another related aspect, the disclosure relates to ACP polypeptides that comprise an amino acid sequence encoded by a nucleic acid sequence that has at least 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to SEQ ID NO: 1, SEQ ID NO: 3, SEQ ID NO: 5, SEQ ID NO: 7, or SEQ ID NO: 9. In some embodiments the nucleic acid sequence encodes an ACP variant with one or more substitutions which result in improved characteristics and/or properties as described herein. In other embodiments, the improved or variant ACP nucleic acid sequence is derived from a species other than a *Marinobacter* species or *E. coli*. In another aspect, the disclosure relates to ACP polypeptides that have an amino acid sequence encoded by a nucleic acid that hybridizes under stringent conditions over substantially the entire length of a nucleic acid corresponding to SEQ ID NO: 1, SEQ ID NO: 3, SEQ ID NO: 5, SEQ ID NO: 7, or SEQ ID NO: 9.

Variations and Mutations

In some embodiments, the AAR or ACP polypeptide is a mutant or a variant of any of the polypeptides described herein. A variant or mutant polypeptide as used herein refers to a polypeptide having an amino acid sequence that differs from a wild-type polypeptide by at least one amino acid. For example, the mutant can have one or more of the following conservative amino acid substitutions, including but not limited to, replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the variant or mutant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. Some preferred fragments of a polypeptide that function as a variant or mutant retain some or all of the biological function (e.g., enzymatic activity) of the corresponding wild-type polypeptide. In some embodiments, the fragment retains at least 75%, at least 80%, at least 90%, at least 95%, or at least 98% or more of the biological function of the corresponding wild-type polypeptide. In other embodiments, the fragment or mutant retains about 100% of the biological function of the corresponding wild-type polypeptide. Guidance in determining which amino acid residues may be substituted, inserted, or deleted without affecting biological activity may be found using computer programs well known in the art, for example, LASERGENE software (DNASTAR, Inc., Madison, Wis.). In yet other embodiments, a fragment exhibits increased biological function as compared to a corresponding wild-type polypeptide. For example, a fragment may display at least a 10%, at least a 25%, at least a 50%, at least a 75%, or at least a 90% improvement in enzymatic activity as compared to the corresponding wild-type polypeptide. In other embodiments, the fragment displays at least 100%, at least 200%, or at least 500% improvement in enzymatic activity as compared to the corresponding wild-type polypeptide.

It is understood that the polypeptides described herein may have additional conservative or non-essential amino acid substitutions which do not have a substantial effect on the polypeptide function. Whether or not a particular substitution will be tolerated (i.e., will not adversely affect the desired biological function, such as acyl-ACP reductase activity), can be determined as known in the art (see Bowie et al. (1990) Science, 247:1306-1310). A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Variants can be naturally occurring or created in vitro. In particular, such variants can be created using genetic engineering techniques, such as site directed mutagenesis, random chemical mutagenesis, Exonuclease III deletion procedures, or standard cloning techniques. Alternatively, such variants, mutants, fragments, analogs, or derivatives can be created using chemical synthesis or modification procedures. Methods of making variants are well known in the art. For example, variants can be prepared by using random and site-directed mutagenesis. Random and site-directed mutagenesis are generally known in the art (see, for example, Arnold (1993) *Curr. Opin. Biotech.* 4:450-455). Random mutagenesis can be achieved using error prone PCR (see, for example, Leung et al. (1989) *Technique* 1:11-15; and Caldwell et al. (1992) *PCR Methods Applic.* 2: 28-33). In error prone PCR, the actual PCR is performed under conditions where the copying fidelity of the DNA polymerase is low, such that a high rate of point mutations is obtained along the entire length of the PCR product. Briefly, in such procedures, nucleic acids to be mutagenized (e.g., a polynucleotide sequence encoding an AAR enzyme) are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mMKCl, 10 mM Tris HCl (pH 8.3), 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated by those in the art that these parameters can be varied as appropriate. The mutagenized nucleic acids are then cloned into an appropriate vector, and the activities of the polypeptides encoded by the mutagenized nucleic acids are evaluated. Site-directed mutagenesis can be achieved using oligonucleotide-directed mutagenesis to generate site-specific mutations in any cloned DNA of interest. Oligonucleotide mutagenesis is described in the art (see, for example, Reidhaar-Olson et al. (1988) *Science* 241:53-57). Briefly, in such procedures a plurality of double stranded oligonucleotides bearing one or more mutations to be introduced into the cloned DNA are synthesized and inserted into the cloned DNA to be mutagenized (e.g., a polynucleotide sequence encoding an AAR polypeptide). Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction (see U.S. Pat. No. 5,965,408). Still another method of generating variants is sexual PCR mutagenesis. In sexual PCR mutagenesis, forced homologous recombination occurs between DNA molecules of different, but highly related, DNA sequences in vitro as a result of random fragmentation of the DNA molecule based on sequence homology. This is followed by fixation of the crossover by primer extension in a PCR reaction. Sexual PCR mutagenesis is described publications known in the art (see, for example, Stemmer (1994) *Proc. Natl. Acad. Sci. U.S.A.* 91:10747-10751). Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such mutator strains have a higher random mutation rate than that of a wild-type strain. Propagating a DNA sequence (e.g., a polynucleotide sequence encoding an AAR polypeptide) in one of these strains will eventually generate random mutations within the DNA. Mutator strains suitable for use for in vivo mutagenesis are described in publication in the art (see, for example, International Patent Application Publication No. WO1991/016427). Variants can also be generated using cassette mutagenesis. In cassette mutagenesis, a small region of a double-stranded DNA molecule is replaced with a synthetic oligonucleotide cassette that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis (see, for example, Arkin et al. (1992) *Proc. Natl. Acad. Sci., U.S.A.* 89:7811-7815). In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins (see, for example, Delegrave et al. (1993) *Biotech. Res.* 11:1548-1552). In some embodiments, variants are created using shuffling procedures wherein portions of a plurality of nucleic acids that encode distinct polypeptides are fused together to create chimeric nucleic acid sequences that encode chimeric polypeptides (as described in, for example, U.S. Pat. Nos. 5,965,408 and 5,939,250).

Production of Fatty Aldehydes and Fatty Alcohols

Figure 4:
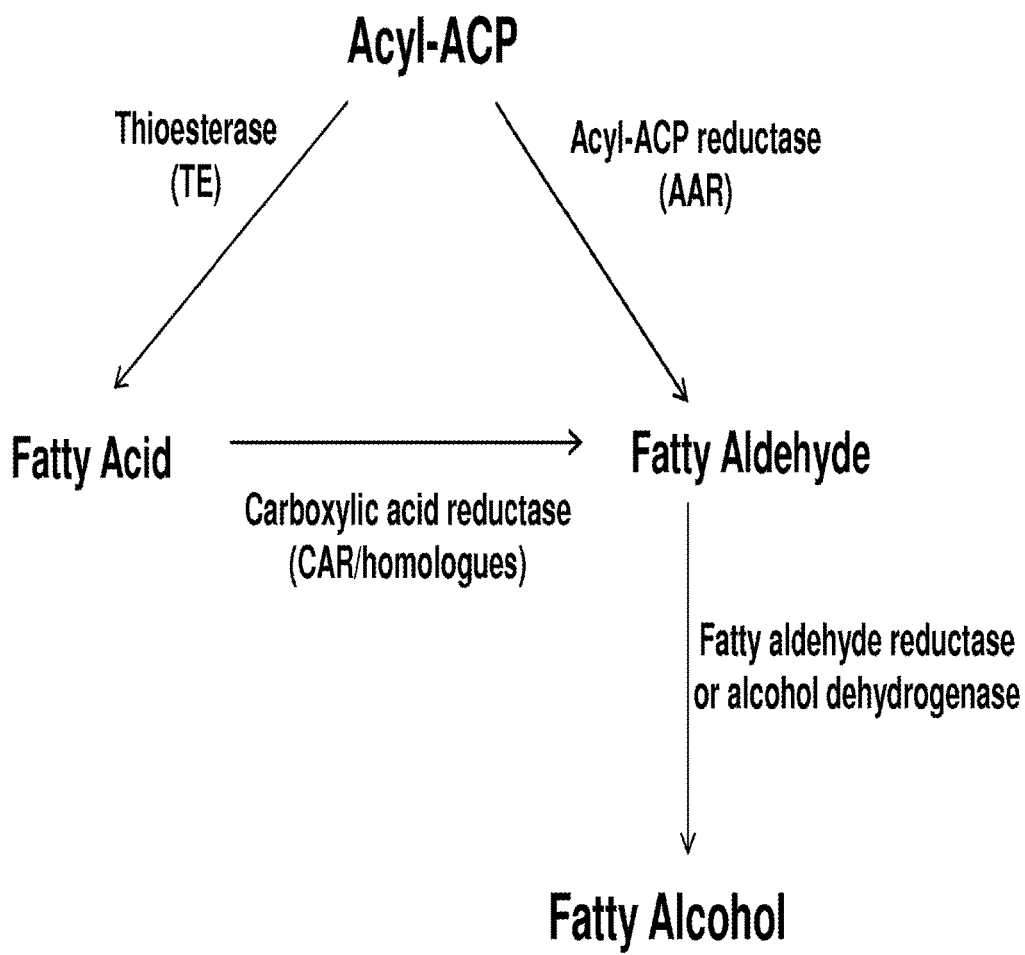
FIG. 4 presents a schematic overview of an exemplary biosynthetic pathway for production of fatty alcohol starting with acyl-ACP, where the production of fatty aldehyde is catalyzed by the enzymatic activity of acyl-ACP reductase (AAR) or thioesterase and carboxylic acid reductase (Car). The fatty aldehyde is converted to fatty alcohol by aldehyde reductase (also referred to as alcohol dehydrogenase). This pathway does not include fatty acyl-CoA synthetase (fadD).

A native or recombinant host cell may comprise a polynucleotide encoding an enzyme having fatty aldehyde biosynthesis activity (also referred to herein as a fatty aldehyde biosynthetic polypeptide or a fatty aldehyde biosynthetic polypeptide or enzyme). A fatty aldehyde is produced when the fatty aldehyde biosynthetic enzyme is expressed or overexpressed in the host cell. Expression or overexpression of an acyl-ACP reductase (AAR) polypeptide in a recombinant host cell may result in production of a fatty aldehyde by the recombinant host cell. In one embodiment, the recombinant host cell produces a fatty aldehyde. In some embodiments, the fatty aldehyde produced by the recombinant host cell is converted into a fatty alcohol. In some embodiments, native (endogenous) fatty aldehyde biosynthetic polypeptides, such as aldehyde reductases, are present in the host cell (e.g., *E. coli*) and are effective to convert fatty aldehydes to fatty alcohols. In other embodiments, a native (endogenous) fatty aldehyde biosynthetic polypeptide is overexpressed. In still other embodiments, an exogenous fatty aldehyde biosynthetic polypeptide is introduced into a recombinant host cell and expressed or overexpressed. A fatty aldehyde may be produced by expressing or overexpressing in the recombinant host cell a polynucleotide encoding a fatty aldehyde biosynthetic polypeptide, such as a polypeptide having acyl-ACP reductase (AAR) activity. Expression of AAR in a recombinant host cell results in the production of fatty aldehydes and fatty alcohols (FIG. 4). Exemplary AAR polypeptides are described herein and in PCT Publication Nos. WO2009/140695 and WO/2009/140696, both of which are expressly incorporated by reference herein.

A composition comprising fatty aldehydes (a fatty aldehyde composition) is produced by culturing a host cell in the presence of a carbon source under conditions effective to express the fatty aldehyde biosynthetic enzyme, e.g., AAR. A recombinant host cell engineered to produce a fatty aldehyde will typically convert some of the fatty aldehyde to a fatty alcohol. In some embodiments, the fatty aldehyde composition comprises fatty aldehydes and fatty alcohols. Typically, the fatty aldehyde composition is recovered from the extracellular environment of the recombinant host cell, i.e., the cell culture medium. In some embodiments, the recombinant host cell includes a polynucleotide encoding a polypeptide (an enzyme) having fatty alcohol biosynthetic activity (also referred to herein as a fatty alcohol biosynthetic polypeptide or a fatty alcohol biosynthetic enzyme), and a fatty alcohol is produced by the recombinant host cell. A composition including the fatty alcohols (i.e., a fatty alcohol composition) may be produced by culturing the recombinant host cell in the presence of a carbon source under conditions effective to express a fatty alcohol biosynthetic enzyme. Native (e.g., endogenous) aldehyde reductases present in a recombinant host cell (e.g., *E. coli*), will convert fatty aldehydes into fatty alcohols. In some embodiments, native (e.g., endogenous) fatty aldehyde biosynthetic polypeptides, such as aldehyde reductases present in the host cell are sufficient to convert fatty aldehydes to fatty alcohols. However, in other embodiments, a fatty alcohol is produced by expressing or overexpressing in the recombinant host cell a polynucleotide encoding a polypeptide having fatty alcohol biosynthetic activity which converts a fatty aldehyde to a fatty alcohol. For example, an alcohol dehydrogenase (also referred to herein as an aldehyde reductase, e.g., EC 1.1.1.1), may be useful in practicing the disclosure. As used herein, the term alcohol dehydrogenase refers to a polypeptide capable of catalyzing the conversion of a fatty aldehyde to a fatty alcohol. One of ordinary skill in the art will appreciate that certain alcohol dehydrogenases are capable of catalyzing other reactions as well, and these non-specific alcohol dehydrogenases also are encompassed by the term alcohol dehydrogenase. Examples of alcohol dehydrogenase polypeptides useful in accordance with the disclosure include, but are not limited to, AlrA of *Acinetobacter* sp. M-1 (SEQ ID NO: 52) or AlrA homologs such as AlrAadp1 (SEQ ID NO: 53) and endogenous *E. coli* alcohol dehydrogenases such as YjgB, (AAC77226) (SEQ ID NO: 5), DkgA (NP_417485), DkgB (NP_414743), YdjL (AAC74846), YdjJ (NP_416288), AdhP (NP_415995), YhdH (NP_417719), YahK (NP_414859), YphC (AAC75598), YqhD (446856) and YbbO [AAC73595.1]. Additional examples are described in International Patent Application Publication Nos. WO2007/136762, WO2008/119082 and WO2010/062480, each of which is expressly incorporated by reference herein. In certain embodiments, the fatty alcohol biosynthetic polypeptide has aldehyde reductase or alcohol dehydrogenase activity (EC 1.1.1.1). In some embodiments, a native (e.g., endogenous) fatty alcohol biosynthetic polypeptide is overexpressed and in other embodiments, an exogenous fatty alcohol biosynthetic polypeptide is introduced into a recombinant host cell and expressed or overexpressed.

Fatty alcohols may be produced via an acyl-CoA dependent pathway utilizing fatty acyl-ACP and fatty acyl-CoA intermediates and an acyl-CoA independent pathway utilizing fatty acyl-ACP intermediates but not a fatty acyl-CoA intermediate. In particular embodiments, the enzyme encoded by the over expressed gene is selected from a fatty acid synthase, an acyl-ACP thioesterase, a fatty acyl-CoA synthase and an acetyl-CoA carboxylase. Fatty alcohols are also made in nature by enzymes that are able to reduce various acyl-ACP or acyl-CoA molecules to the corresponding primary alcohols (see U.S. Patent Publication Nos. 20100105963 and 20110206630, and U.S. Pat. No. 8,097,439, expressly incorporated by reference herein). A fatty alcohol composition often includes fatty alcohols together with other fatty acid derivatives, e.g., fatty aldehydes and/or fatty acids. Typically, the fatty alcohol composition is recovered from the extracellular environment of the recombinant host cell, i.e., the cell culture medium. In certain embodiments, the expression of a polypeptide, for example, an enzyme directly or indirectly involved in fatty acid biosynthesis is modulated (e.g., expressed, overexpressed or attenuated), wherein such modulation results in a higher yield, higher titer or higher productivity of a fatty acid derivative of interest, such as a fatty alcohol. The enzyme may be encoded by a fatty acid biosynthetic polynucleotide that is exogenous or heterologous (e.g., a polypeptide originating from an organism other than the parental host cell, or, a variant of a polypeptide native to the parental microbial cell) or an endogenous polypeptide (e.g., a polypeptide native to the parental host cell) wherein the endogenous polypeptide is overexpressed in the recombinant host cell. Table 1 provides a listing of exemplary proteins which can be expressed in recombinant host cells to facilitate production of particular fatty alcohol compositions.

TABLE 1

| Gene Designations | | | | | |
|---|---|---|---|---|---|
| Gene Designation | Source Organism | Enzyme Name | Accession No. | EC Number | Exemplary Use |
| Fatty Acid Production Increase/Product Production Increase | | | | | |
| accA | *E. coli*, *Lactococci* | acetyl-CoA carboxylase, subunit A (carboxyltransferase alpha) | AAC73296, NP_414727 | 6.4.1.2 | increase Malonyl-CoA production |
| accB | *E. coli*, *Lactococci* | acetyl-CoA carboxylase, subunit B (BCCP: biotin carboxyl carrier protein) | NP_417721 | 6.4.1.2 | increase Malonyl-CoA production |
| accC | *E. coli*, *Lactococci* | acetyl-CoA carboxylase, subunit C (biotin carboxylase) | NP_417722 | 6.4.1.2, 6.3.4.14 | increase Malonyl-CoA production |
| accD | *E. coli*, *Lactococci* | acetyl-CoA carboxylase, subunit D (carboxyltransferase beta) | NP_416819 | 6.4.1.2 | increase Malonyl-CoA production |

TABLE 1-continued

Gene Designations

| Gene Designation | Source Organism | Enzyme Name | Accession No. | EC Number | Exemplary Use |
|---|---|---|---|---|---|
| fadD | E. coli W3110 | acyl-CoA synthase | AP_002424 | 2.3.1.86, 6.2.1.3 | increase Fatty acid production |
| fabA | E. coli K12 | β-hydroxydecanoylthio-esterdehydratase/isomerase | NP_415474 | 4.2.1.60 | increase fatty acyl-ACP/CoA production |
| fabB | E. coli | 3-oxoacyl-[acyl-carrier-protein] synthase I | BAA16180 | 2.3.1.41 | increase fatty acyl-ACP/CoA production |
| fabD | E. coli K12 | [acyl-carrier-protein] S-malonyltransferase | AAC74176 | 2.3.1.39 | increase fatty acyl-ACP/CoA production |
| fabF | E. coli K12 | 3-oxoacyl-[acyl-carrier-protein] synthase II | AAC74179 | 2.3.1.179 | increase fatty acyl-ACP/CoA production |
| fabG | E. coli K12 | 3-oxoacyl-[acyl-carrier protein] reductase | AAC74177 | 1.1.1.100 | increase fatty acyl-ACP/CoA production |
| fabH | E. coli K12 | 3-oxoacyl-[acyl-carrier-protein] synthase III | AAC74175 | 2.3.1.180 | increase fatty acyl-ACP/CoA production |
| fabI | E. coli K12 | enoyl-[acyl-carrier-protein] reductase | NP_415804 | 1.3.1.9 | increase fatty acyl-ACP/CoA production |
| fabR | E. coli K12 | transcriptional Repressor | NP_418398 | none | modulate unsaturated fatty acid production |
| fabV | Vibrio cholerae | enoyl-[acyl-carrier-protein] reductase | YP_001217283 | 1.3.1.9 | increase fatty acyl-ACP/CoA production |
| fabZ | E. coli K12 | (3R)-hydroxymyristol acyl carrier protein dehydratase | NP_414722 | 4.2.1.— | increase fatty acyl-ACP/CoA production |
| fadE | E. coli K13 | acyl-CoA dehydrogenase | AAC73325 | 1.3.99.3, 1.3.99.— | reduce fatty acid degradation |
| fadR | E. coli | transcriptional regulatory protein | NP_415705 | none | Block or reverse fatty acid degradation |

Chain Length Control

| | | | | | |
|---|---|---|---|---|---|
| tesA (with or without leader sequence) | E. coli | thioesterase - leader sequence is amino acids 1-26 | P0ADA1 | 3.1.2.—, 3.1.1.5 | C18 Chain Length |
| tesA (without leader sequence) | E. coli | thioesterase | AAC73596, NP_415027 | 3.1.2.—, 3.1.1.5 | C18:1 Chain Length |
| tesA (mutant of E. coli thioesterase I complexed with octanoic acid) | E. coli | thioesterase | L109P | 3.1.2.—, 3.1.1.5 | <C18 Chain Length |
| fatB1 | Umbellularia californica | thioesterase | Q41635 | 3.1.2.14 | C12:0 Chain Length |
| fatB2 | Cuphea hookeriana | thioesterase | AAC49269 | 3.1.2.14 | C8:0-C10:0 Chain Length |
| fatB3 | Cuphea hookeriana | thioesterase | AAC72881 | 3.1.2.14 | C14:0-C16:0 Chain Length |
| fatB | Cinnamomum camphora | thioesterase | Q39473 | 3.1.2.14 | C14:0 Chain Length |
| fatB | Arabidopsis thaliana | thioesterase | CAA85388 | 3.1.2.14 | C16:1 Chain Length |
| fatA1 | Helianthus annuus | thioesterase | AAL79361 | 3.1.2.14 | C18:1 Chain Length |
| atfata | Arabidopsis thaliana | thioesterase | NP_189147, NP_193041 | 3.1.2.14 | C18:1 Chain Length |
| fatA | Brassica juncea | thioesterase | CAC39106 | 3.1.2.14 | C18:1 Chain Length |
| fatA | Cuphea hookeriana | thioesterase | AAC72883 | 3.1.2.14 | C18:1 Chain Length |
| tesA | Photbcterium profundum | thioesterase | YP_130990 | 3.1.2.14 | Chain Length |

TABLE 1-continued

Gene Designations

| Gene Designation | Source Organism | Enzyme Name | Accession No. | EC Number | Exemplary Use |
|---|---|---|---|---|---|
| tesB | E. coli | thioesterase | NP_414986 | 3.1.2.14 | Chain Length |
| fadM | E. coli | thioesterase | NP_414977 | 3.1.2.14 | Chain Length |
| yciA | E. coli | thioesterase | NP_415769 | 3.1.2.14 | Chain Length |
| ybgC | E. coli | thioesterase | NP_415264 | 3.1.2.14 | Chain Length |
| Saturation Level Control* | | | | | |
| Sfa | E. coli | suppressor of fabA | AAN79592, AAC44390 | none | increase monounsaturated fatty acids |
| fabA | E. coli K12 | β-hydroxydecanoylthio-esterdehydratase/isomerase | NP_415474 | 4.2.1.60 | produce unsaturated fatty acids |
| GnsA | E. coli | suppressors of the secG null mutation | ABD18647.1 | none | increase unsaturated fatty acid esters |
| GnsB | E. coli | suppressors of the secG null mutation | AAC74076.1 | none | increase unsaturated fatty acid esters |
| fabB | E. coli | 3-oxoacyl-[acyl-carrier-protein] synthase I | BAA16180 | 2.3.1.41 | modulate unsaturated fatty acid production |
| des | Bacillus subtilis | D5 fatty acyl desaturase | O34653 | 1.14.19 | modulate unsaturated fatty acid production |
| Product Output: Ester Production | | | | | |
| AT3G51970 | Arabidopsis thaliana | long-chain-alcohol O-fatty-acyltransferase | NP_190765 | 2.3.1.26 | wax production |
| ELO1 | Pichia angusta | fatty acid elongase | BAD98251 | 2.3.1.— | produce very long chain length fatty acids |
| plsC | Saccharomyces cerevisiae | acyltransferase | AAA16514 | 2.3.1.51 | wax production |
| DAGAT/DGAT | Arabidopsis thaliana | diacylglycerolacyltransferase | AAF19262 | 2.3.1.20 | wax production |
| hWS | Homo sapiens | acyl-CoA wax alcohol acyltransferase | AAX48018 | 2.3.1.20 | wax production |
| aft1 | Acinetobacter sp. ADP1 | bifunctional wax ester synthase/acyl-CoA:diacylglycerolacyl-transferase | AAO17391 | 2.3.1.20 | wax production |
| ES9 | Marinobacter hydrocarbonoclasticus | wax ester synthase | ABO21021 | 2.3.1.20 | wax production |
| mWS | Simmondsia chinensis | wax ester synthase | AAD38041 | 2.3.1.— | wax production |
| acr1 | Acinetobacter sp. ADP1 | acyl-CoA reductase | YP_047869 | 1.2.1.42 | modify output |
| yqhD | E. Coli K12 | alcohol dehydrogenase | AP_003562 | 1.1.—.— | modify output |
| AAT | Fragaria × ananassa | alcohol O-acetyltransferase | AAG13130 | 2.3.1.84 | modify output |
| Product Output: Fatty Alcohol Output | | | | | |
|  |  | thioesterases (see above) |  |  | increase fatty acid/fatty alcohol production |
| BmFAR | Bombyx mori | FAR (fatty alcohol forming acyl-CoA reductase) | BAC79425 | 1.1.1.— | convert acyl-CoA to fatty alcohol |
| acr1 | Acinetobacter sp. ADP1 | acyl-CoA reductase | YP_047869 | 1.2.1.42 | reduce fatty acyl-CoA to fatty aldehydes |
| yqhD | E. coli W3110 | alcohol dehydrogenase | AP_003562 | 1.1.—.— | reduce fatty aldehydes to fatty alcohols; increase fatty alcohol production |
| alrA | Acinetobacter sp. ADP1 | alcohol dehydrogenase | CAG70252 | 1.1.—.— | reduce fatty aldehydes to fatty alcohols |
| BmFAR | Bombyx mori | FAR (fatty alcohol forming acyl-CoA reductase) | BAC79425 | 1.1.1.— | reduce fatty acyl-CoA to fatty alcohol |
| GTNG_1865 | Geobacillus thermodenitrificans NG80-2 | long-chain aldehyde dehydrogenase | YP_001125970 | 1.2.1.3 | reduce fatty aldehydes to fatty alcohols |

TABLE 1-continued

Gene Designations

| Gene Designation | Source Organism | Enzyme Name | Accession No. | EC Number | Exemplary Use |
|---|---|---|---|---|---|
| AAR | Synechococcus elongatus | acyl-ACP reductase | YP_400611 | 1.2.1.80 1.2.1.42 | reduce fatty acyl-ACP/CoA to fatty aldehydes |
| carB | Mycobacterium smegmatis | carboxylic acid reductase (CAR) protein | YP_889972 | 6.2.1.3, 1.2.1.42 | reduce fatty acids to fatty aldehyde |
| FadD | E. coli K12 | acyl-CoA synthetase | NP_416319 | 6.2.1.3 | activates fatty acids to fatty acyl-CoAs |
| atoB | Erwinia carotovora | acetyl-CoA acetyltransferase | YP_049388 | 2.3.1.9 | production of butanol |
| hbd | Butyrivibrio fibrisolvens | beta-hydroxybutyryl-CoA dehydrogenase | BAD51424 | 1.1.1.157 | production of butanol |
| CPE0095 | Clostridium perfringens | crotonasebutyryl-CoA dehydryogenase | BAB79801 | 4.2.1.55 | production of butanol |
| bcd | Clostridium beijerinckii | butyryl-CoA dehydryogenase | AAM14583 | 1.3.99.2 | production of butanol |
| ALDH | Clostridium beijerinckii | coenzyme A-acylating aldehyde dehydrogenase | AAT66436 | 1.2.1.3 | production of butanol |
| AdhE | E. coli CFT073 | aldehyde-alcohol dehydrogenase | AAN80172 | 1.1.1.1 1.2.1.10 | production of butanol |
| Product Export | | | | | |
| AtMRP5 | Arabidopsis thaliana | Arabidopsis thaliana multidrug resistance-associated | NP_171908 | none | modify product export amount |
| AmiS2 | Rhodococcus sp. | ABC transporter AmiS2 | JC5491 | none | modify product export amount |
| AtPGP1 | Arabidopsis thaliana | Arabidopsis thaliana p glycoprotein 1 | NP_181228 | none | modify product export amount |
| AcrA | Candidatus Protochlamydia amoebophila UWE25 | putative multidrug-efflux transport protein acrA | CAF23274 | none | modify product export amount |
| AcrB | Candidatus Protochlamydia amoebophila UWE25 | probable multidrug-efflux transport protein, acrB | CAF23275 | none | modify product export amount |
| TolC | Francisella tularensis subsp. novicida | outer membrane protein [Cell envelope biogenesis, | ABD59001 | none | modify product export amount |
| AcrE | Shigella sonnei Ss046 | transmembrane protein affects septum formation and cell membrane permeability | YP_312213 | none | modify product export amount |
| AcrF | E. coli | acriflavine resistance protein F | P24181 | none | modify product export amount |
| tll1619 | Thermosynechococcus elongatus [BP-1] | multidrug efflux transporter | NP_682409.1 | none | modify product export amount |
| tll0139 | Thermosynechococcus elongatus [BP-1] | multidrug efflux transporter | NP_680930.1 | none | modify product export amount |
| Fermentation | | | | | |
| replication checkpoint genes | | | | | increase output efficiency |
| umuD | Shigella sonnei Ss046 | DNA polymerase V, subunit | YP_310132 | 3.4.21.— | increase output efficiency |
| umuC | E. coli | DNA polymerase V, subunit | ABC42261 | 2.7.7.7 | increase output efficiency |
| pntA, pntB | Shigella flexneri | NADH:NADPH transhydrogenase (alpha and beta subunits) | P07001, P0AB70 | 1.6.1.2 | increase output efficiency |
| Other | | | | | |
| fabK | Streptococcus pneumoniae | trans-2-enoyl-ACP reductase II | AAF98273 | 1.3.1.9 | Contributes to fatty acid biosynthesis |
| fabL | Bacillus licheniformis DSM 13 | enoyl-(acyl carrier protein) reductase | AAU39821 | 1.3.1.9 | Contributes to fatty acid biosynthesis |

TABLE 1-continued

Gene Designations

| Gene Designation | Source Organism | Enzyme Name | Accession No. | EC Number | Exemplary Use |
|---|---|---|---|---|---|
| fabM | *Streptococcus mutans* | trans-2, cis-3-decenoyl-ACP isomerase | DAA05501 | 4.2.1.17 | Contributes to fatty acid biosynthesis |

Recombinant Host Cells and Cell Cultures

Strategies to increase production of fatty aldehyde or fatty alcohol compositions by recombinant host cells include increased flux through the fatty acid biosynthetic pathway by overexpression of native fatty aldehyde or fatty alcohol biosynthetic genes and expression of exogenous fatty aldehyde and fatty alcohol biosynthetic genes from different organisms in the production host. As used herein, the term recombinant host cell or engineered host cell refers to a host cell whose genetic makeup has been altered relative to the corresponding wild-type host cell, for example, by deliberate introduction of new genetic elements and/or deliberate modification of genetic elements naturally present in the host cell. The offspring of such recombinant host cells also contain these new and/or modified genetic elements. In any of the aspects of the disclosure described herein, the host cell can be selected from a plant cell, insect cell, fungus cell (e.g., a filamentous fungus, such as *Candida* sp., or a budding yeast, such as *Saccharomyces* sp.), an algal cell and a bacterial cell. In one preferred embodiment, recombinant host cells are recombinant microorganisms. Examples of host cells that are microorganisms include, but are not limited to, cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces*. In some embodiments, the host cell is a Gram-positive bacterial cell. In other embodiments, the host cell is a Gram-negative bacterial cell. In some embodiments, the host cell is an *E. coli* cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcusopacus* cell, a *Rhizomucormiehei* cell, or a *Mucormichei* cell. In yet other embodiments, the host cell is a *Streptomyces lividans* cell or a *Streptomyces murinus* cell. In yet other embodiments, the host cell is an Actinomycetes cell. In some embodiments, the host cell is a *Saccharomyces cerevisiae* cell.

In other embodiments, the host cell is a eukaryotic plant cell, an alga cell, a cyanobacterium cell, a green-sulfur bacterium cell, a green non-sulfur bacterium cell, a purple sulfur bacterium cell, a purple non-sulfur bacterium cell, an extremophile cell, a yeast cell, a fungus cell, an engineered cell of any of species described herein, or a synthetic organism. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus* elongates BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridium thermocellum, Penicillium chrysogenum, Pichiapastoris, Saccharomyces cerevisiae, Schizosaccharomyces pombe, Pseudomonas fluorescens,* or *Zymomonas mobilis*.

Engineering Host Cells

In some embodiments, a polynucleotide (or gene) sequence is provided to the host cell by way of a recombinant vector, which includes a promoter operably linked to the polynucleotide sequence. In certain embodiments, the promoter is a developmentally-regulated, an organelle-specific, a tissue-specific, an inducible, a constitutive, or a cell-specific promoter. In some embodiments, the recombinant vector includes at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. The expression vectors described herein include a polynucleotide sequence in a form suitable for expression of the polynucleotide sequence in a host cell. It will be appreciated by those skilled in the art that the design of the expression vector can depend on such factors as the choice of the host cell to be transformed, the level of expression of polypeptide desired, and the like. The expression vectors described herein can be introduced into host cells to produce polypeptides, including fusion polypeptides, encoded by the polynucleotide sequences as described above (supra). Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes including to increase expression of the recombinant polypeptide; to increase the solubility of the recombinant polypeptide; and to aid in the purification of the recombinant polypeptide by acting as a ligand in affinity purification. Often, in fusion expression vectors, a proteolytic cleavage site is introduced at the junction of the fusion moiety and the recombinant polypeptide. This allows separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX vector (Pharmacia Biotech, Inc., Piscataway, N.J.; Smith et al. (1988) *Gene* 67:31-40), pMAL vector (New England Biolabs, Beverly, Mass.), and pRITS vector (Pharmacia Biotech, Inc., Piscataway, N.J.), which fuse glutathione S-transferase (GST), maltose E binding protein, or protein A, respectively, to the target recombinant polypeptide.

Examples of inducible, non-fusion *E. coli* expression vectors include pTrc vector (Amann et al. (1988) *Gene* 69:301-315) and pET 11d vector (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gni). This viral polymerase is supplied by host strains such as BL21(DE3) or HMS174(DE3) from a resident k prophage harboring a T7 gni gene under the transcriptional control of the lacUV 5 promoter. Suitable expression systems for both prokaryotic and eukaryotic cells are well known in the art (see, e.g., Sambrook et al. (1989) Molecular Cloning: A Laboratory Manual, second edition, Cold Spring Harbor Laboratory). Examples of inducible, non-fusion *E. coli* expression vectors include pTrc vector (Amann et al. (1988) *Gene* 69:301-315) and PET 11d vector (Studier et al. (1990) Gene Expression Technology: Methods in Enzymology 185, Academic Press, San Diego, Calif., pp. 60-89). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra). For stable transformation of bacterial cells, it is known that (depending upon the expression vector and transformation technique used) a certain fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug. The engineered or recombinant host cell as described herein (supra) is a cell used to produce a fatty acid derivative composition such as a fatty aldehyde or a fatty alcohol. In any of the aspects of the disclosure described herein, the host cell can be selected from a eukaryotic plant, bacteria, algae, cyanobacterium, green-sulfur bacterium, green non-sulfur bacterium, purple sulfur bacterium, purple non-sulfur bacterium, extremophile, yeast, fungus, engineered organisms thereof, or a synthetic organism. In some embodiments, the host cell is light dependent or fixes carbon. In some embodiments, the host cell has autotrophic activity. Various host cells can be used to produce fatty acid derivatives, as described herein.

The host cells or microorganisms of the disclosure include host strains or host cells that are genetically engineered or modified to contain alterations in order to test the efficiency of specific mutations on enzymatic activities (i.e., recombinant cells or microorganisms). Various optional genetic manipulations and alterations can be used interchangeably from one host cell to another, depending on what native enzymatic pathways are present in the original host cell. In one embodiment, a host strain can be used for testing the expression of an AAR polypeptide in combination with other biosynthetic polypeptides (e.g., enzymes). A host strain may encompasses a number of genetic alterations in order to test specific variables, including but not limited to, culture conditions including fermentation components, carbon source (e.g., feedstock), temperature, pressure, reduced culture contamination conditions, and oxygen levels.

In one embodiment, a host strain encompasses an optional fadE and fhuA deletion. Acyl-CoA dehydrogenase (FadE) is an enzyme that is important for metabolizing fatty acids. It catalyzes the second step in fatty acid utilization (beta-oxidation), which is the process of breaking long chains of fatty acids (acyl-CoAs) into acetyl-CoA molecules. More specifically, the second step of the β-oxidation cycle of fatty acid degradation in bacteria is the oxidation of acyl-CoA to 2-enoyl-CoA, which is catalyzed by FadE. When *E. coli* lacks FadE, it cannot grow on fatty acids as a carbon source but it can grow on acetate. The inability to utilize fatty acids of any chain length is consistent with the reported phenotype of fadE strains, i.e., fadE mutant strains where FadE function is disrupted. The fadE gene can be optionally knocked out or attenuated to assure that acyl-CoAs, which may be intermediates in a fatty acid derivative pathway, can accumulate in the cell such that all acyl-CoAs can be efficiently converted to fatty acid derivatives. However, fadE attenuation is optional when sugar is used as a carbon source since under such condition expression of FadE is likely repressed and FadE therefore may only be present in small amounts and not able to efficiently compete with ester synthase or other enzymes for acyl-CoA substrates. FadE is repressed due to catabolite repression. *E. coli* and many other microbes prefer to consume sugar over fatty acids, so when both sources are available sugar is consumed first by repressing the fad regulon (see D. Clark, *J Bacteriol*. (1981) 148(2):521-6)). Moreover, the absence of sugars and the presence of fatty acids induces FadE expression. Acyl-CoA intermediates could be lost to the beta oxidation pathway since the proteins expressed by the fad regulon (including FadE) are up-regulated and will efficiently compete for acyl-CoAs. Thus, it can be beneficial to have the fadE gene knocked out or attenuated. Since most carbon sources are mainly sugar based, it is optional to attenuate FadE. The gene fhuA codes for the TonA protein, which is an energy-coupled transporter and receptor in the outer membrane of *E. coli* (V. Braun (2009) *J Bacteriol*. 191(11):3431-3436). Its deletion is optional. The fhuA deletion allows the cell to become more resistant to phage attack which can be beneficial in certain fermentation conditions. Thus, it may be desirable to delete fhuA in a host cell that is likely subject to potential contamination during fermentation runs.

In another embodiment, the host strain (supra) also encompasses optional overexpression of one or more of the following genes including fadR, fabA, fabD, fabG, fabH, fabV, and/or fabF. Examples of such genes are fadR from *Escherichia coli*, fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). The overexpression of one or more of these genes, which code for enzymes and regulators in fatty acid biosynthesis, can serve to increase the titer of fatty-acid derivative compounds including fatty aldehydes and fatty alcohols under various culture conditions.

In another embodiment, *E. coli* strains are used as host cells for the production of fatty acid derivatives such a fatty aldehydes and/or fatty alcohols. Similarly, these host cells provide optional overexpression of one or more biosynthesis genes (i.e., genes coding for enzymes and regulators of fatty acid biosynthesis) that can further increase or enhance the titer of fatty-acid derivative compounds such as fatty acid derivatives (e.g., fatty alcohols, fatty aldehydes, etc.) under various culture conditions including, but not limited to, fadR, fabA, fabD, fabG, fabH, fabV and/or fabF. Examples of genetic alterations include fadR from *Escherichia coli*, fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). In some embodiments, synthetic operons that carry these biosynthetic genes can be engineered and expressed in cells in order to test fatty aldehyde and/or fatty alcohol overexpression under various culture conditions and/or further enhance fatty aldehyde and/or fatty alcohol production. Such synthetic operons contain one or more biosynthetic gene. The ifab138 operon, for example, is an engineered operon that contains optional fatty acid biosynthetic genes, including fabV from *Vibrio cholera*, fabH from *Salmonella typhimurium*, fabD from *S. typhimurium*, fabG from *S. typhimurium*, fabA from *S. typhimurium* and/or fabF from *Clostridium acetobutylicum* that can be used to facilitate overexpression of fatty acid derivatives in order to test specific culture conditions. One advantage of such synthetic operons is that the rate of fatty acid derivative production can be further increased or enhanced.

In some embodiments, the host cells or microorganisms that are used to express ACP and biosynthetic enzymes (e.g., TE, ES, CAR, AAR, ADC, etc.) will further express genes that encompass certain enzymatic activities that can increase the production to one or more particular fatty acid derivative(s) such as fatty alcohols, fatty aldehydes, fatty esters, fatty amines, bifunctional fatty acid derivatives, diacids and the like. In one embodiment, the host cell has thioesterase activity (E.C. 3.1.2.* or E.C. 3.1. 2.14 or E.C. 3.1.1.5) for the production of fatty acids which can be increased by overexpressing the gene. In another embodiment, the host cell has ester synthase activity (E.C. 2.3.1.75) for the production of fatty esters. In another embodiment, the host cell has acyl-ACP reductase (AAR) (E.C. 1.2.1.80) activity and/or alcohol dehydrogenase activity (E.C. 1.1.1.1.) and/or fatty alcohol acyl-CoA reductase (FAR) (E.C. 1.1.1.*) activity and/or carboxylic acid reductase (CAR) (EC 1.2.99.6) activity for the production of fatty alcohols. In another embodiment, the host cell has acyl-ACP reductase (AAR) (E.C. 1.2.1.80) activity for the production of fatty aldehydes. In another embodiment, the host cell has acyl-ACP reductase (AAR) (E.C. 1.2.1.80) activity and decarbonylase (ADC) activity for the production of alkanes and alkenes. In another embodiment, the host cell has acyl-CoA reductase (E.C. 1.2.1.50) activity, acyl-CoA synthase (FadD) (E.C. 2.3.1.86) activity, and thioesterase (E.C. 3.1.2.* or E.C. 3.1. 2.14 or E.C. 3.1.1.5) activity for the production of fatty alcohols. In another embodiment, the host cell has ester synthase activity (E.C. 2.3.1.75), acyl-CoA synthase (FadD) (E.C. 2.3.1.86) activity, and thioesterase (E.C. 3.1.2.* or E.C. 3.1. 2.14 or E.C. 3.1.1.5) activity for the production of fatty esters. In another embodiment, the host cell has *OleA* activity for the production of ketones. In another embodiment, the host cell has OleBCD activity for the production of internal olefins. In another embodiment, the host cell has acyl-ACP reductase (AAR) (E.C. 1.2.1.80) activity and alcohol dehydrogenase activity (E.C. 1.1.1.1.) for the production of fatty alcohols. In another embodiment, the host cell has thioesterase (E.C. 3.1.2.* or E.C. 3.1. 2.14 or E.C. 3.1.1.5) activity and decarboxylase activity for making terminal olefins. The expression of enzymatic activities in microorganisms and microbial cells is taught by U.S. Pat. Nos. 8,097,439; 8,110,093; 8,110,670; 8,183,028; 8,268,599; 8,283,143; 8,232,924; 8,372,610; and 8,530,221, which are incorporated herein by reference. In other embodiments, the host cells or microorganisms that are used to express ACP and other biosynthetic enzymes will include certain native enzyme activities that are upregulated or overexpressed in order to produce one or more particular fatty acid derivative(s) such as fatty aldehydes and/or fatty alcohols. In one embodiment, the host cell has a native thioesterase (E.C. 3.1.2.* or E.C. 3.1. 2.14 or E.C. 3.1.1.5) activity for the production of fatty acids which can be increased by overexpressing the thioesterase gene.

The present disclosure includes host strains or microorganisms that express genes that code for AAR and other biosynthetic enzymes (supra). The recombinant host cells produce fatty acid derivatives such as fatty aldehydes and fatty alcohols and compositions and blends thereof. The fatty acid derivatives are typically recovered from the culture medium and/or are isolated from the host cells. In one embodiment, the fatty acid derivatives such as fatty aldehydes and fatty alcohols are recovered from the culture medium (extracellular). In another embodiment, the fatty acid derivatives such as fatty aldehydes and fatty alcohols are isolated from the host cells (intracellular). In another embodiment, the fatty acid derivatives such as fatty aldehydes and fatty alcohols are recovered from the culture medium and isolated from the host cells. The fatty acid derivatives composition produced by a host cell can be analyzed using methods known in the art, for example, GC-FID, in order to determine the distribution of particular fatty acid derivatives as well as chain lengths and degree of saturation of the components of the fatty acid derivative composition such as fatty aldehyde and fatty alcohol compositions.

Examples of host cells that function as microorganisms (e.g., microbial cells), include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces*. In some embodiments, the host cell is a Gram-positive bacterial cell. In other embodiments, the host cell is a Gram-negative bacterial cell. In some embodiments, the host cell is an *E. coli* cell. In some embodiment, the host cell is an *E. coli* B cell, an *E. coli* C cell, an *E. coli* K cell, or an *E. coli* W cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In still other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In yet other embodiments, the host cell is a *Streptomyces lividans* cell or a *Streptomyces murinus* cell. In yet other embodiments, the host cell is an Actinomycetes cell. In some embodiments, the host cell is a *Saccharomyces cerevisiae* cell. In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus* elongates BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridium thermocellum, Penicillium chrysogenum, Pichia pastoris, Saccharomyces cerevisiae, Schizosaccharomyces pombe, Pseudomonas fluorescens,* or *Zymomonas mobilis*. In one particular embodiment, the microbial cell is from a cyanobacteria including, but not limited to, *Prochlorococcus, Synechococcus, Synechocystis, Cyanothece,* and *Nostoc punctiforme*. In another embodiment, the microbial cell is from a specific cyanobacterial species including, but not limited to, *Synechococcus elongatus* PCC7942, *Synechocystis* sp. PCC6803, and *Synechococcus* sp. PCC7001.

Culture of Recombinant Host Cells and Fermentation

As used herein, the term fermentation broadly refers to the conversion of organic materials into target substances by host cells, for example, the conversion of a carbon source by recombinant host cells into fatty acids or derivatives thereof by propagating a culture of the recombinant host cells in a media comprising the carbon source. The conditions permissive for the production refer to any conditions that allow a host cell to produce a desired product, such as a fatty aldehyde or a fatty alcohol. Similarly, the condition or conditions in which the polynucleotide sequence of a vector is expressed means any conditions that allow a host cell to synthesize a polypeptide. Suitable conditions include, for example, fermentation conditions. Fermentation conditions can include many parameters including, but not limited to, temperature ranges, levels of aeration, feed rates and media composition. Each of these conditions, individually and in combination, allows the host cell to grow. Fermentation can be aerobic, anaerobic, or variations thereof (such as microaerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source.

For small scale production, the engineered host cells can be grown in batches of, for example, about 100 µL, 200 µL, 300 µL, 400 µL, 500 µL, 1 mL, 5 mL, 10 mL, 15 mL, 25 mL, 50 mL, 75 mL, 100 mL, 500 mL, 1 L, 2 L, 5 L, or 10 L; fermented; and induced to express a desired polynucleotide sequence, such as a polynucleotide sequence encoding an ACP and/or biosynthetic polypeptide. For large scale production, the engineered host cells can be grown in batches of about 10 L, 100 L, 1000 L, 10,000 L, 100,000 L, and 1,000,000 L or larger; fermented; and induced to express a desired polynucleotide sequence. Alternatively, large scale fed-batch fermentation may be carried out. The fatty acid derivative compositions described herein are found in the extracellular environment of the recombinant host cell culture and can be readily isolated from the culture medium. A fatty acid derivative such as a fatty aldehyde or fatty alcohol may be secreted by the recombinant host cell, transported into the extracellular environment or passively transferred into the extracellular environment of the recombinant host cell culture. The fatty acid derivative is isolated from a recombinant host cell culture using routine methods known in the art.

Products Derived From Recombinant Host Cells

As used herein, the fraction of modem carbon or fM has the same meaning as defined by National Institute of Standards and Technology (NIST) Standard Reference Materials (SRMs4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), fM is approximately 1.1. Bioproducts (e.g., the fatty acid derivatives including fatty aldehydes and/or fatty alcohols produced in accordance with the present disclosure) include biologically produced organic compounds. In particular, the fatty acid derivatives produced using the fatty acid biosynthetic pathway herein, have not been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588). The ability to distinguish bioproducts from petroleum based organic compounds is beneficial in tracking these materials in commerce. For example, organic compounds or chemicals including both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/^{12}C$ and the corresponding $\delta^{13}C$ values. Furthermore, lipid matter of C3 and C4 plants analyze differently than materials derived from the carbohydrate components of the same plants as a consequence of the metabolic pathway. Within the precision of measurement, $^{13}C$ shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the C3 (or Calvin-Benson) photosynthetic cycle and those that incorporate the C4 (or Hatch-Slack) photosynthetic cycle. In C3 plants, the primary $CO_2$ fixation or carboxylation reaction involves the enzyme ribulose-1,5-diphosphate carboxylase, and the first stable product is a 3-carbon compound. C3 plants, such as hardwoods and conifers, are dominant in the temperate climate zones. In C4 plants, an additional carboxylation reaction involving another enzyme, phosphoenol-pyruvate carboxylase, is the primary carboxylation reaction. The first stable carbon compound is a 4-carbon acid that is subsequently decarboxylated. The $CO_2$ thus released is refixed by the C3 cycle. Examples of C4 plants are tropical grasses, corn, and sugar cane. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al. (1977) *Radiocarbon* 19:355). Coal and petroleum fall generally in this latter range. The $^{13}C$ measurement scale was originally defined by a zero set by Pee Dee Belemnite (PDB) limestone, where values are given in parts per thousand deviations from this material. The δ13C values are expressed in parts per thousand (per mil), abbreviated, ‰, and are calculated as follows:

$$\delta^{13}C(‰)=[(^{13}C/^{12}C)sample-(^{13}C/^{12}C)standard]/(^{13}C/^{12}C)standard \times 1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include bioproducts produced by any of the methods described herein, including, for example, fatty acid derivative products. Specifically, the bioproduct can have a $\delta^{13}C$ of about −28 or greater, about −27 or greater, −20 or greater, −18 or greater, −15 or greater, −13 or greater, −10 or greater, or −8 or greater. For example, the bioproduct can have a $\delta^{13}C$ of about −30 to about −15, about −27 to about −19, about −25 to about −21, about −15 to about −5, about −13 to about −7, or about −13 to about −10. In other instances, the bioproduct can have a $\delta^{13}C$ of about −10, −11, −12, or −12.3. Bioproducts produced in accordance with the disclosure herein, can also be distinguished from petroleum based organic compounds by comparing the amount of $^{14}C$ in each compound. Because $^{14}C$ has a nuclear half-life of 5730 years, petroleum based fuels containing older carbon can be distinguished from bioproducts which contain newer carbon (see, e.g., Currie, Source Apportionment of Atmospheric Particles, Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)). The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about $1.2 \times 10^{-12}$, with an approximate relaxation "half-life" of 7-10 years. This latter half-life must not be taken literally; rather, one must use the detailed atmospheric nuclear input/decay function to trace the variation of atmospheric and biospheric $^{14}C$ since the onset of the nuclear age. It is this latter biospheric $^{14}C$ time characteristic that holds out the promise of annual dating of recent biospheric carbon. $^{14}C$ can be measured by accelerator mass spectrometry (AMS), with results given in units of fraction of modern carbon (fM). fM is defined by National Institute of Standards and Technology (NIST) Standard Reference Materials (SRMs) 4990B and 4990C. As used herein, fraction of modern carbon or fM has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), fM is approximately 1.1. The compositions described herein include bioproducts that can have an $fM^{14}C$ of at least about 1. For example, the bioproduct of the disclosure can have an $fM^{14}C$ of at least about 1.01, an $fM^{14}C$ of about 1 to about 1.5, an $fM^{14}C$ of about 1.04 to about 1.18, or an $fM^{14}C$ of about 1.111 to about 1.124.

Another measurement of $^{14}C$ is known as the percent of modern carbon (pMC). For an archaeologist or geologist using $^{14}C$ dates, AD 1950 equals zero years old. This also represents 100 pMC. Bomb carbon in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning 100% equal to 107.5 pMC and 0% equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty acid derivatives as described herein can have a pMC of at least about 50, 60, 70, 75, 80, 85, 90, 95, 96, 97, 98, 99, or 100. In other instances, a fatty acid derivative described herein can have a pMC of between about 50 and about 100; about 60 and about 100; about 70 and about 100; about 80 and about 100; about 85 and about 100; about 87 and about 98; or about 90 and about 95. In yet other instances, a fatty acid derivative described herein can have a pMC of about 90, 91, 92, 93, 94, or 94.2.

Fatty Aldehyde and Fatty Alcohol Compositions and their Use

Aldehydes are used to produce many specialty chemicals. For example, aldehydes are used to produce polymers, resins (e.g., BAKELITE resin), dyes, flavorings, plasticizers, perfumes, pharmaceuticals, and other chemicals, some of which may be used as solvents, preservatives, or disinfectants. In addition, certain natural and synthetic compounds, such as vitamins and hormones, are aldehydes, and many sugars contain aldehyde groups. Fatty aldehydes can be converted to fatty alcohols by chemical or enzymatic reduction. Fatty alcohols also have multiple commercial uses. Worldwide annual sales of fatty alcohols and their derivatives are in excess of U.S. $1 billion. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats.

The disclosure also provides a surfactant composition or a detergent composition including a fatty alcohol produced by any of the methods described herein. One of ordinary skill in the art will appreciate that, depending upon the intended purpose of the surfactant or detergent composition, different fatty alcohols can be produced and used. For example, when the fatty alcohols described herein are used as a feedstock for surfactant or detergent production, one of ordinary skill in the art will appreciate that the characteristics of the fatty alcohol feedstock will affect the characteristics of the surfactant or detergent composition produced. Hence, the characteristics of the surfactant or detergent composition can be selected for by producing particular fatty alcohols for use as a feedstock. A fatty alcohol-based surfactant and/or detergent composition described herein can be mixed with other surfactants and/or detergents well known in the art. In some embodiments, the mixture can include at least about 10%, at least about 15%, at least about 20%, at least about 30%, at least about 40%, at least about 50%, at least about 60%, or a range bounded by any two of the foregoing values, by weight of the fatty alcohol. In other examples, a surfactant or detergent composition can be made that includes at least about 5%, at least about 10%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of a fatty alcohol that includes a carbon chain that is 8, 9, 10, 11, 12, 13, 14, 15, 16, 17, 18, 19, 20, 21, or 22 carbons in length. Such surfactant or detergent compositions also can include at least one additive, such as a microemulsion or a surfactant or detergent from nonmicrobial sources such as plant oils or petroleum, which can be present in the amount of at least about 5%, at least about 10%, at least about 15%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of the fatty alcohol.

EXAMPLES

The following specific examples are intended to illustrate the disclosure and should not be construed as limiting the scope of the claims.

Protocols and Methods

Screening a Library

All protocols described herein rely on a 96 well plate-master block-2 mL system (Greiner Bio-One, Monroe, N.C. or Corning, Amsterdam, The Netherlands) for growing cultures, and plates (Costar, Inc.) for extracting fatty acid species from the culture broth. The protocols provided below are examples of fermentation conditions. Alternative protocols can be used to evaluate fatty acid species production.

32° C. Culture Protocol (4NBT)

20 µL LB culture (from an LB culture growing in a 96 well plate) was used to inoculate 400 µL 2NBT media (Table 2), which was then incubated for approximately 16 hours at 32° C. shaking. 20 µL of the overnight seed was used to inoculate 400 µL 4NBT with either 1 or 2 g/L nitrogen (NBT_1N or NBT_2N). After growing at 32° C. for 6 hours, the cultures were induced with IPTG (final concentration 1 mM) (Table 2). The cultures were then incubated at 32° C. with shaking for 18 hours, after which they were extracted following the standard extraction protocol detailed below.

TABLE 2

Media Names and Formulations

| Media Name | | Formulation |
|---|---|---|
| 2NBT | 1 X | 5x Salt Soln. with NH4Cl |
| | 1 g/L | 100 g/L NH4Cl |
| | 1 mg/L | 10 mg/mL Thiamine |
| | 1 mM | 1M MgSO4 |
| | 0.1 mM | 1M CaCl2 |
| | 20 g/L | 500 g/L glucose |
| | 1 X | 1000x TM2 |
| | 10 mg/L | 10 g/L Fe Citrate |
| | 100 µg/mL | 100 mg/ml spectinomycin |
| | 100 mM | 2M BisTris (pH 7.0) |
| 4NBT_1N | 1 X | 5x Salt Soln. with NH4Cl |
| | 1 mg/L | 10 mg/mL Thiamine |
| | 1 mM | 1M MgSO4 |
| | 0.1 mM | 1M CaCl2 |
| | 40 g/L | 500 g/L glucose |
| | 1 X | 1000x TM2 |
| | 10 mg/L | 10 g/L Fe Citrate |
| | 100 µg/mL | 100 mg/ml spectinomycin |
| | 100 mM | 2M BisTris (pH 7.0) |
| 4NBT_2N | 1 X | 5x Salt Soln. with NH4Cl |
| | 1 g/L | 100 g/L NH4Cl |
| | 1 mg/L | 10 mg/mL Thiamine |
| | 1 mM | 1M MgSO4 |
| | 0.1 mM | 1M CaCl2 |
| | 40 g/L | 500 g/L glucose |
| | 1 X | 1000x TM2 |
| | 10 mg/L | 10 g/L Fe Citrate |

TABLE 2-continued

Media Names and Formulations

| Media Name | Formulation | |
|---|---|---|
| | 100 µg/mL | 100 mg/ml spectinomycin |
| | 100 mM | 2M BisTris (pH 7.0) |

Fatty Acid Species Standard Extraction Protocol

To each well to be extracted 40 µL of 1M HCl, followed by 300 µL of butyl acetate (with 500 mg/L C11-FAME as internal standard) was added. The 96 well plates were then heat-sealed using a plate sealer (ALPS-300 heater; Abgene, ThermoScientific, Rockford, Ill.), and shaken for 15 minutes at 2000 rpm using MIXMATE mixer (Eppendorf, Hamburg, Germany). After shaking, the plates were centrifuged for 10 minutes at 4500 rpm at room temperature (Allegra X-15R, rotor SX4750A, Beckman Coulter, Brea, Calif.) to separate the aqueous and organic layers. 50 µL of the organic layer was transferred to a 96 well plate (polypropylene, Corning, Amsterdam, The Netherlands), which was subsequently heat sealed and stored at −20° C. until evaluated by GC-FID using the FALC_Broth.met method. The FALC_Broth.met method was carried out as follows: 1 µL of sample was injected onto an analytical column (DB-1, 10 m×180 µm×0.2 µM film thickness, available from JW 121-101A) in an Agilent 7890A GC Ultra device (Agilent, Santa Clara, Calif.) with a flame ionization detector (FID). The instrument was set up to detect and quantify C6 to C18 fatty alcohols. The protocol detailed above represents standard conditions, which may be modified as necessary to optimize the analytical results.

Fatty Acid Species—Standard Nile Red Assay Protocol

After 24 hours of fermentation, a Nile Red assay was performed by adding 70 µL of fermentation broth to 130 µL of 1.54 µg/mL Nile Red in 84.6% water and 15.4% acetonitrile solution for a final assay concentration of 1 µg/mL Nile Red in a Greiner MicrolonFluotrac 200 plate, and mixed by pipetting up and down. Relative fluorescence units were measured at excitation of 540 nm and emission of 630 nm using the SpectraMax M2 unit.

Building Error Prone Libraries

Standard techniques known to those of skill in the art were used to prepare error prone libraries. In one example, the vector backbone was prepared using restriction endonucleases in the vector, while the creation of diversity in the DNA insert was generated by PCR amplification from a DNA template under conditions favoring the incorporation of mismatched nucleotides. In one approach, the cloning of the vector backbone and a DNA insert with diversity was performed using the INFUSION Cloning System (Clontech Laboratories, Inc., Mountain View, Calif.), according to the manufacturer's protocol.

Building Saturation Libraries

Standard techniques known to those of skill in the art were used to prepare saturation libraries. In one example, the vector backbone was prepared using restriction endonucleases in the vector, while the creation of diversity in the DNA insert was generated using degenerate primers. In one approach, the cloning of the vector backbone and a DNA insert with diversity was performed using INFUSION Cloning System (Clontech Laboratories, Inc., Mountain View, Calif.) according to the manufacturer's protocol.

Building Combination Libraries

Mutations identified as beneficial were combined to provide AAR variants with further improvements in the production of fatty alcohol species. Standard techniques known to those of skill in the art were used to prepare the combination libraries. In one example, the vector backbone was prepared using restriction endonucleases in the vector, while the creation of diversity in the DNA insert was generated using primers to introduce the desired mutations. As described above, in one approach, the cloning of the vector backbone and a DNA insert with diversity was performed using INFUSION Cloning System (Clontech Laboratories, Inc., Mountain View, Calif.), according to manufacturer's protocol. Combination libraries can be generated using the transfer PCR (tPCR) protocol (Erijman et al. (2011) *J. Structural Bio.* 175:171-177).

Library Screening

Once the library diversity was generated in an error-prone, saturation library or combination library, it was screened using one of the methods described above. Two types of hits were identified: (1) increased amount of fatty alcohol (FALC titer); and/or (2) increased amount of medium-chain FALC such as dodecanol (C12) or tetradecanol (C14). Also identified were hexadecanol (C16) and octadecanol (C18). The mutations in the AAR variants within each hit were identified by sequencing using standard techniques routinely employed by those of skill in the art. Tables 4, 5 and 6 list the mutations (hits) identified as beneficial in saturation libraries and combination libraries.

Example 1: Improved Fatty Alcohol Production Using AAR_7942 by Acyl Carrier Protein (ACP) Mediated Increased Flux Through the Fatty Acid Synthesis Pathway When terminal pathway enzymes from sources other than *E. coli* are expressed in *E. coli* as the heterologous host to convert fatty acyl-ACPs to products, limitations may exist in the recognition, affinity and/or turnover of the recombinant pathway enzyme towards the *E. coli* fatty acyl-ACPs. Although ACP proteins are conserved to some extent in all organisms, their primary sequence can differ even within a given species. In order to test this hypothesis the acp genes from several cyanobacteria were cloned downstream from the *Synechococcus elongatus* PCC7942 acyl-ACP reductase (AAR_7942) present in plasmid pLS9-185, which is a pCL1920 derivative (3-5 copies/cell). In addition, the sfp gene (Accession no. X63158; SEQ ID NO: 11) from *Bacillus subtilis*, encoding a phosphopantetheinyl transferase with broad substrate specificity, was cloned downstream of the respective acp genes. This enzyme is involved in conversion of the inactive apo-ACP to the active holo-ACP. The plasmids constructed are described in Table 3.

TABLE 3

Plasmids Coexpressing Cyanobacterial ACP with and without
B. subtilis sfp Downstream from S. elongatus PCC7942 AAR

| Base Plasmid | ACP Source | ACP - SEQ ID NO. (NA/AA*) | Without sfp | With sfp |
|---|---|---|---|---|
| pLS9-185 | Synechococcus elongatus 7942 | 7/8 | pDS168 | pDS168S |
| pLS9-185 | Synechocystis sp. 6803 | 3/4 | pDS169 | not available |
| pLS9-185 | Prochlorococcus marinus MED4 | 5/6 | pDS170 | pDS170S |
| pLS9-185 | Nostoc punctiforme 73102 | 1/2 | pDS171 | pDS171S |
| pLS9-185 | Nostoc sp. 7120 | 9/10 | pDS172 | pDS172S |

*NA = nucleic acid sequence; AA = amino acid sequence/polypeptide sequence

All the acp genes were cloned with a synthetic RBS into the EcoRI site immediately downstream of the aar gene in pLS9-185 using INFUSION technology. The EcoRI site was reconstructed downstream of the acp gene. Similarly, the B. subtilis sfp gene was INFUSION cloned into this EcoRI site along with a synthetic RBS. All plasmids were transformed into E. coli MG1655 DV2. The control for these experiments was the expression of AAR alone (pLS9-185).

Figure 5:
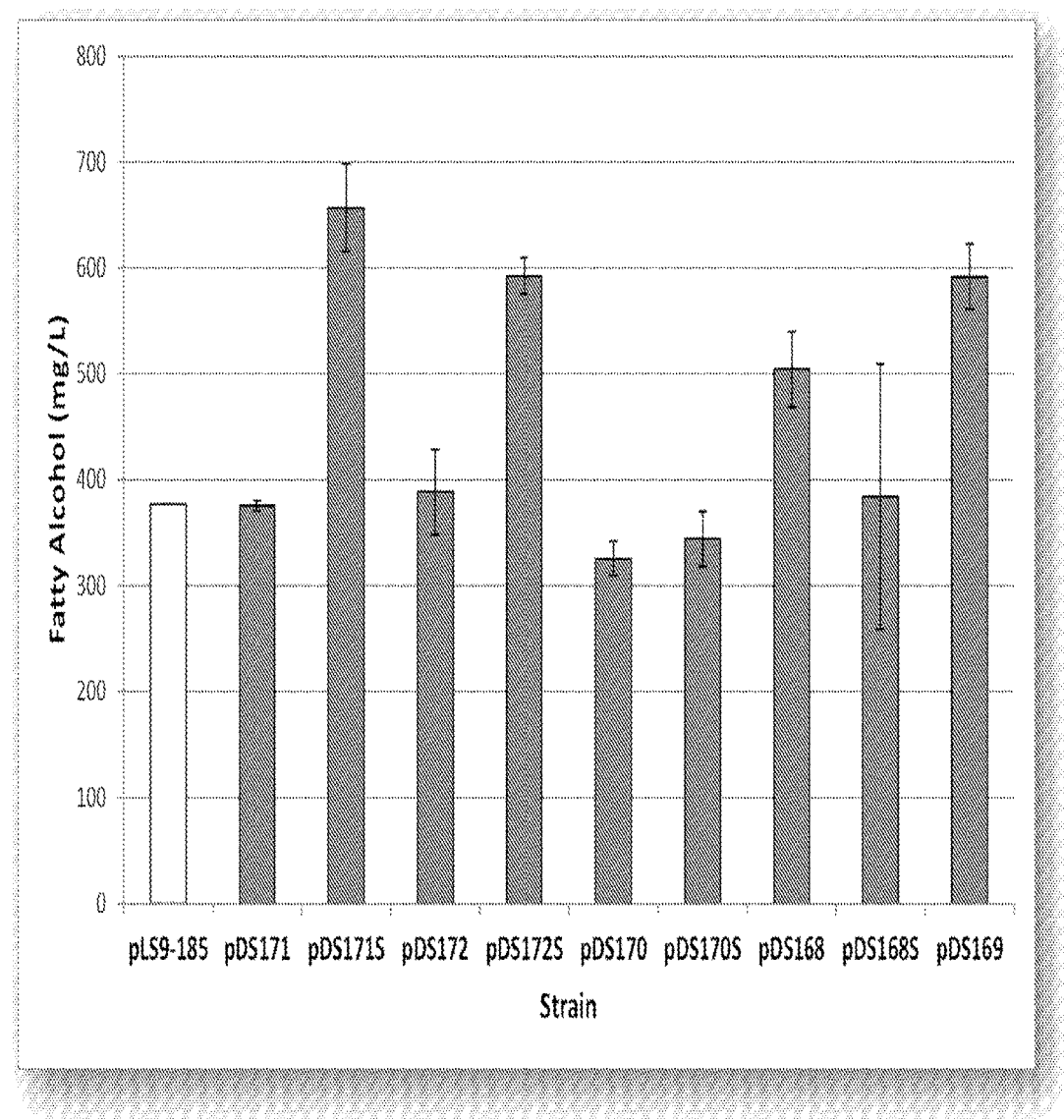
FIG. 5 shows fatty alcohol production in *E. coli* DV2 expressing *Synechococcus elongatus* acyl-ACP reductase (AAR_7942) and coexpressing various cyanobacterial acyl carrier proteins (ACPs).

The results from standard shake flask fermentation experiments are shown in FIG. 5. Significant improvement in fatty alcohol titers were observed in strains containing the plasmids pDS171S, pDS172S, pDS168 and pDS169, demonstrating that ACP overexpression can be beneficial for fatty alcohol production. While not wishing to be bound by theory, it is hypothesized that ACP overexpression can be beneficial for fatty alcohol production by aiding in the recognition, affinity and/or turnover of acyl-ACPs by the heterologous terminal pathway enzyme (see Table 3 (supra) for the source of the ACPs and presence or absence of sfp.)

Figure 6:
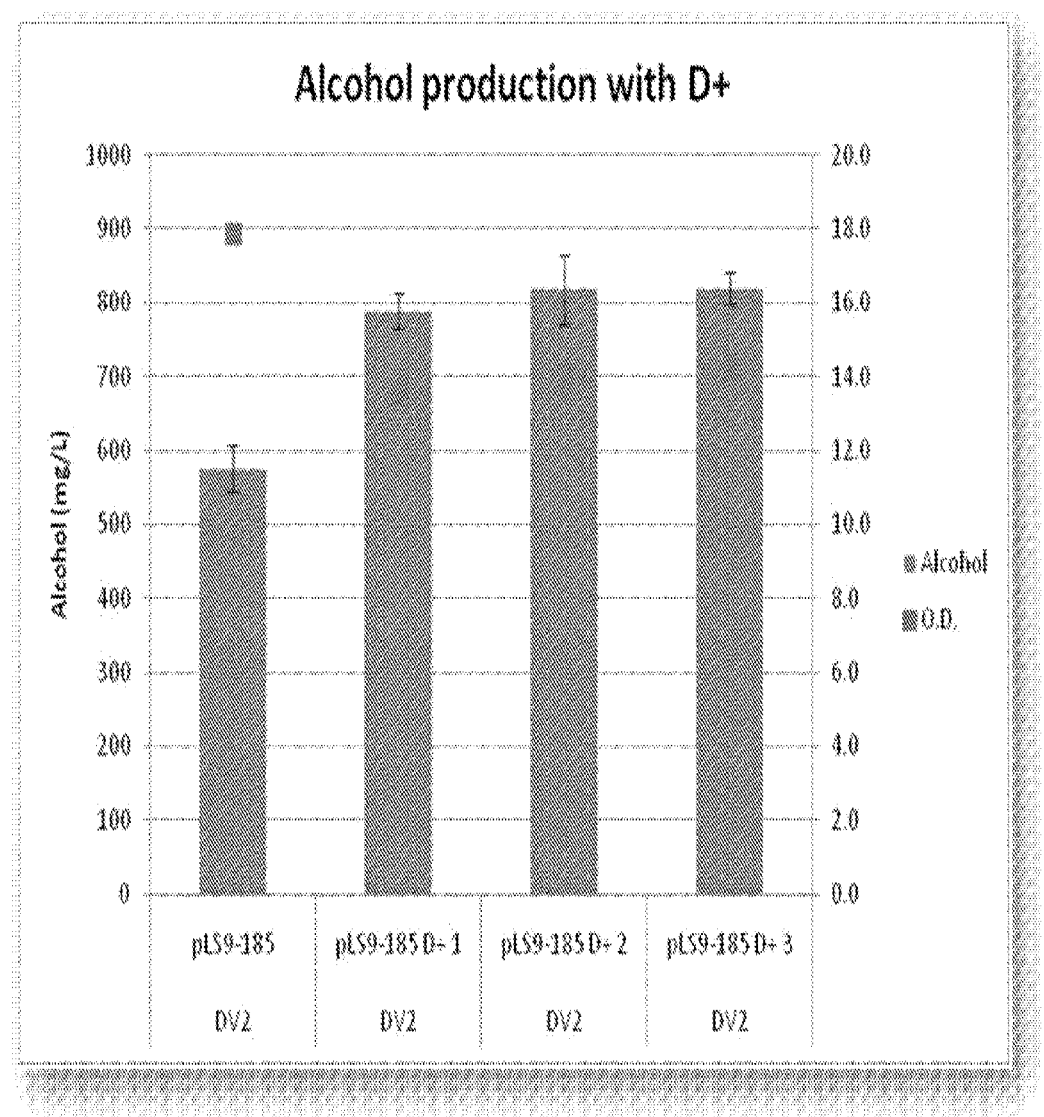
FIG. 6 shows fatty alcohol production in *E. coli* DV2 expressing *Synechococcus elongatus* acyl-ACP reductase (AAR_7942) (pLS9-185) and coexpressing the acetyl carboxylase complex from *Corynebacterium glutamicum* (pSL9-185-D+) (three individual strains are shown, see D+1, D+2 and D+3).

Example 2: Improved Fatty Alcohol Production Using AAR_7942 by Acetyl-CoA Carboxylase (ACC) Mediated Increased Flux Through the Fatty Acid Synthesis The main precursors for fatty acid biosynthesis are malonyl-CoA and acetyl-CoA. It has been suggested that these precursors limit the rate of fatty acid biosynthesis in E. coli. In this example, a synthetic acetyl-CoA carboxylase, acc, operon [Corynebacterium glutamicum accDCAB+birA; SEQ ID NOs: 45 or 46, 48, and 50 also referred to as D+] was expressed alongside acyl-ACP reductase (AAR) from Synechococcus elongatus PCC7942 (AAR_7942). The accD+ operon was cloned downstream of the AAR_7942 gene in plasmid pLS9-185. The resulting plasmid and the pLS9-185 control plasmid were transformed into E. coli DV2. The strains were evaluated for fatty alcohol production in a standard shake flask protocol. As shown in FIG. 6, the coexpression of the synthetic Corynebacterium glutamicum acc operon led to increased fatty alcohol production.

Example 3: Error Prone Library, Combination and Limited Saturation Libraries Prepared Using AAR_7942 as a Template A. Error Prone Library An error prone library of the acyl-ACP reductase from Synechococcus elongatus PCC7942 (AAR_7942) was built and screened for variants that showed improvements over the wild type AAR_7942. The plasmid used to make the error prone library was designated "pDS171S" (see Table 3). The error prone library was screened using one of the standard protocols described above. The improvements were classified as either improving titer or increasing the fraction of C10-C14 fatty alcohols produced without significantly affecting titer (results not shown).

B. Combination and Limited Saturation Libraries

Standard techniques known to those of skill in the art were used to prepare combination libraries and saturation libraries based on positions 17, 18 and 19. The mutations tested in the combination libraries and saturation libraries (Tables 4A and 4B) were originally identified in the error prone library of AAR_7942 described above. Plasmids, strains and screening protocols used were the same as described in Example 1. The results from screening the error prone library are shown in Tables 4A and 4B. Table 4A shows AAR_7942 mutations that led to increased fatty alcohol titers and Table 4B shows mutations that led to increased fraction of C14 fatty alcohol without significantly affecting overall fatty alcohol titer.

TABLE 4A

Mutations From an AAR 7942 Combination and Limited Saturation
Libraries Correlated with Improved Fatty Alcohol Titer

| Mutations | FALC Titer (total*) | C14-FALC (% fraction) | Normalized FALC (% over control) | Normalized C14 (% over control) |
|---|---|---|---|---|
| Combo α Library | | | | |
| S18T, C63Y, S96T, L177H, A281V | 2473 | 48% | 251% | 294% |
| S18T, C63Y, S96T, L177H, A281V E284K | 2202 | 50% | 200% | 229% |
| S18T, C63Y, S96T, L177H | 2088 | 43% | 189% | 197% |
| S18T, C63Y | 1798 | 39% | 182% | 241% |
| C63H, S967T, L177H, A281V | 2045 | 53% | 180% | 237% |
| S18T, C63Y, A281V, E283K | 1696 | 45% | 172% | 278% |
| S18T, C63Y | 1640 | 43% | 166% | 260% |

TABLE 4A-continued

Mutations From an AAR 7942 Combination and Limited Saturation Libraries Correlated with Improved Fatty Alcohol Titer

| Mutations | FALC Titer (total*) | C14-FALC (% fraction) | Normalized FALC (% over control) | Normalized C14 (% over control) |
|---|---|---|---|---|
| S18T, L177H, A281V, E283K | 1618 | 44% | 164% | 270% |
| S18T, L177H, A281V, E283K | 1617 | 43% | 164% | 264% |
| S18T, S96T, L177H, E283K | 1814 | 43% | 160% | 194% |
| S18T, C63H, L177H | 1811 | 39% | 160% | 173% |
| S18T, L177H, A281V, E283K | 1503 | 39% | 152% | 237% |
| L65F, S96T, A281V, E283K | 1638 | 43% | 144% | 191% |
| C63Y, A281V, A282T | 1622 | 38% | 143% | 168% |
| L11F, C63Y, S96T, L177H, A281V A282T, E283K | 1579 | 41% | 143% | 186% |
| L65F, S96T, L177H, A281V, E283K | 1585 | 42% | 140% | 189% |
| G22S, C63H, S96T, L177H, E283K | 1229 | 39% | 125% | 237% |
| C63H, L65F, S96T, A281V | 1178 | 41% | 119% | 252% |
| S18T, L65F, S96T, L177H, A281V | 1136 | 33% | 115% | 203% |
| C63R, L177H, A281V, E283K | 1275 | 44% | 112% | 196% |
| Saturation Libraries | | | | |
| S18M | 2809 | 40% | 243% | 212% |
| S18F | 2564 | 54% | 222% | 285% |
| S18Y | 2550 | 45% | 221% | 236% |
| S18W | 2530 | 55% | 227% | 314% |
| S18M | 2495 | 41% | 224% | 231% |
| S18Y | 2039 | 44% | 188% | 252% |
| S18Y | 1997 | 44% | 179% | 251% |
| S18T | 1729 | 31% | 155% | 177% |
| S18T | 1690 | 31% | 152% | 176% |
| S18T | 1683 | 31% | 151% | 176% |
| S18T | 1599 | 30% | 143% | 172% |
| S18L | 1568 | 48% | 141% | 271% |
| S18C | 1381 | 28% | 120% | 149% |
| S18C | 1372 | 26% | 123% | 147% |
| S18C | 1368 | 28% | 118% | 148% |
| S18L | 1359 | 47% | 122% | 266% |
| S18C | 1355 | 26% | 121% | 148% |
| S18V | 1344 | 30% | 121% | 170% |
| S18C | 1340 | 26% | 120% | 147% |
| S18L | 1326 | 47% | 119% | 268% |
| S18L | 1315 | 47% | 118% | 266% |
| S18C | 1313 | 26% | 118% | 149% |
| S18V | 1306 | 30% | 121% | 170% |
| S18C | 1305 | 26% | 117% | 148% |
| S18L | 1302 | 47% | 117% | 267% |
| V17L | 1188 | 23% | 110% | 130% |
| V17L | 1185 | 33% | 103% | 173% |
| V17L | 1175 | 32% | 102% | 171% |
| Combo β Library | | | | |
| S18W, S96T, E283K, R286Q, A324V | 3437 | 49% | 246% | 255% |
| S18W | 3286 | 53% | 235% | 275% |
| S18W, S96T, E283K | 3199 | 46% | 229% | 237% |
| S18W, C63Y, S96T | 3186 | 46% | 228% | 241% |
| S18W, C68Y, E2834K | 2949 | 50% | 211% | 260% |
| C63Y, E283K | 2680 | 36% | 192% | 189% |
| S18W, C63Y | 2675 | 54% | 191% | 280% |
| C63Y, S96T | 2583 | 38% | 185% | 196% |
| C63Y, E283K, Q316K | 2420 | 36% | 173% | 188% |
| S96T | 1605 | 23% | 115% | 121% |
| E283K | 1532 | 25% | 110% | 131% |

TABLE 4B

Mutations From AAR_7942 Combination and Limited Saturation Libraries Correlated with Increased C14 Fatty Alcohol Fraction

| | FALC Titer (total*) | C14-FALC (% fraction) | Normalized FALC (% over control) | Normalized C14 (% over control) |
|---|---|---|---|---|
| Combo α Library | | | | |
| C63H, S96T, L177H, A281V | 2045.36 | 53% | 180% | 237% |
| G22S, C63H, F64V, S96T, L177H A281V | 152.47 | 51% | 14% | 233% |

TABLE 4B-continued

Mutations From AAR_7942 Combination and Limited Saturation
Libraries Correlated with Increased C14 Fatty Alcohol Fraction

|  | FALC Titer (total*) | C14-FALC (% fraction) | Normalized FALC (% over control) | Normalized C14 (% over control) |
|---|---|---|---|---|
| S18T, C63H, S96T, L177H, A281V E283K | 2202.46 | 50% | 200% | 229% |
| S18T, C63Y, S96T, L177H, A281V | 2472.80 | 48% | 251% | 294% |
| S18T, C63Y, A281V, E283K | 1695.59 | 45% | 172% | 278% |
| S18T, L177H, A281V, E283K | 1618.20 | 44% | 164% | 270% |
| C63R, L177H, A281V, E283K | 1275.38 | 44% | 112% | 196% |
| S18T, C63H, L65F, S96T, L177H A281V, E283K | 912.50 | 44% | 83% | 199% |
| S18T, S96T, L177H, E283K | 1814.34 | 43% | 160% | 194% |
| S18T, L179H, A281V, E283K | 1616.51 | 43% | 164% | 264% |
| S18T, C63H, S96T, L177H | 2088.12 | 43% | 189% | 197% |
| L65F, S96T, A281V, E283K | 1638.28 | 43% | 144% | 191% |
| C63H, L65F, A281V, E283K | 632.66 | 43% | 56% | 190% |
| S18T, C63Y | 1640.33 | 43% | 166% | 260% |
| L65F, S96T, L177H, A281V, E283K | 1585.32 | 42% | 140% | 189% |
| C63Y, L65F, L177H | 639.46 | 41% | 56% | 184% |
| C63H, L65F, S96T, A281V | 1177.76 | 41% | 119% | 252% |
| L11F, C63Y, S96T, L177H, A281V A282T, E283K | 1578.54 | 41% | 143% | 186% |
| S18T, C63Y | 1797.99 | 39% | 182% | 241% |
| S18T, L178H, A282V, E284K | 1502.59 | 39% | 152% | 237% |
| G23S, C63H, S96T, L177H, E283K | 1229.34 | 39% | 125% | 237% |
| S18T, C63H, L177H | 1811.40 | 39% | 160% | 173% |
| C63Y, A281V, A282T | 1622.23 | 38% | 143% | 168% |
| S18T, C63Y, L65F, S96T, L177H A281V, E283K, M284I | 454.42 | 35% | 41% | 162% |
| S18T, L65F, S96T, L177H, A281V | 1135.95 | 33% | 115% | 203% |
| L65F, L178H, G180S, E283K | 151.40 | 33% | 13% | 146% |
| L66F, L177H, G180S, E283K | 143.83 | 31% | 13% | 138% |
| S18T, C63H, L65F, L177H | 103.21 | 30% | 9% | 133% |
| Saturation Libraries |  |  |  |  |
| S18W | 2530 | 55% | 227% | 314% |
| S18F | 2564 | 54% | 222% | 285% |
| V17N | 571 | 49% | 49% | 260% |
| S18L | 1568 | 48% | 141% | 271% |
| S18L | 1024 | 47% | 92% | 268% |
| S18L | 1326 | 47% | 119% | 268% |
| S18L | 1302 | 47% | 117% | 267% |
| S18L | 1106 | 47% | 99% | 267% |
| S18L | 1315 | 47% | 118% | 266% |
| S18L | 1359 | 47% | 122% | 266% |
| S18Y | 2550 | 45% | 221% | 236% |
| S18Y | 2039 | 44% | 188% | 252% |
| S18Y | 1997 | 44% | 179% | 251% |
| S18M | 2495 | 41% | 224% | 231% |
| S18M | 2809 | 40% | 243% | 212% |
| V17L | 1127 | 33% | 97% | 175% |
| V17L | 1185 | 33% | 103% | 173% |
| V17L | 1091 | 32% | 94% | 171% |
| V17L | 1175 | 32% | 102% | 171% |
| S18T | 1729 | 31% | 155% | 177% |
| S18T | 1690 | 31% | 152% | 176% |
| S18T | 1683 | 31% | 151% | 176% |
| S18T | 1599 | 30% | 143% | 172% |
| S18V | 1344 | 30% | 121% | 170% |
| S18V | 1306 | 30% | 121% | 170% |
| S18V | 1015 | 30% | 91% | 169% |
| S18C | 1381 | 28% | 120% | 149% |
| S18C | 1368 | 28% | 118% | 148% |
| R19H, R58S | 873 | 27% | 81% | 152% |
| V17C | 927 | 27% | 80% | 140% |
| V17C | 882 | 26% | 76% | 139% |
| S18C | 1313 | 26% | 118% | 149% |
| S18C | 1355 | 26% | 121% | 148% |
| S18C | 1305 | 26% | 117% | 148% |
| S18C | 1372 | 26% | 123% | 147% |
| S18C | 1340 | 26% | 120% | 147% |
| V17W | 849 | 25% | 73% | 134% |
| V17W | 815 | 25% | 71% | 133% |
| V17W | 831 | 25% | 72% | 132% |
| V17W | 840 | 25% | 73% | 131% |
| R19V | 844 | 24% | 78% | 139% |
| R19V | 813 | 24% | 75% | 136% |

TABLE 4B-continued

Mutations From AAR_7942 Combination and Limited Saturation Libraries Correlated with Increased C14 Fatty Alcohol Fraction

|  | FALC Titer (total*) | C14-FALC (% fraction) | Normalized FALC (% over control) | Normalized C14 (% over control) |
|---|---|---|---|---|
| R19V | 821 | 24% | 76% | 135% |
| R19V | 862 | 24% | 80% | 135% |
| R19V | 814 | 24% | 75% | 135% |
| R19K, V117L | 1188 | 23% | 110% | 130% |
| R19S | 803 | 22% | 74% | 128% |
| R19T | 735 | 22% | 68% | 127% |
| R19S | 783 | 22% | 72% | 127% |
| R19S | 764 | 22% | 75% | 129% |
| R19I | 862 | 22% | 80% | 123% |
| R19A | 901 | 21% | 83% | 122% |
| R19A | 705 | 21% | 65% | 119% |
| R19M | 937 | 20% | 86% | 114% |
| Combo β Library | | | | |
| S18W | 3184 | 57% | 228% | 296% |
| S18W, C63Y | 2675 | 54% | 191% | 280% |
| S18W, C63Y, S95T | 2832 | 54% | 203% | 279% |
| S18W, S96T, E283K | 2874 | 54% | 206% | 278% |
| S18W, C63Y, E283K | 2915 | 51% | 209% | 263% |
| S18W, S96T, E283K, R286Q, A324V | 3437 | 49% | 246% | 255% |
| C63Y, S96T | 2583 | 38% | 185% | 196% |
| C63Y, E283K | 2176 | 38% | 156% | 195% |
| C63Y, E283K, Q316K | 2420 | 36% | 173% | 188% |
| E283K | 1474 | 25% | 105% | 132% |
| S96T | 1605 | 23% | 115% | 121% |
| Combo 3 Library | | | | |
| S18W | 2853 | 217% | 51% | 274% |
| Y23N | 954 | 72% | 35% | 191% |
| Y23N, Q238H | 892 | 68% | 35% | 190% |
| G150D, I274N | 766 | 62% | 30% | 162% |
| I274N | 1359 | 107% | 29% | 161% |
| I274N, A285V | 1317 | 103% | 28% | 155% |
| P38T, I274N, A285V | 587 | 46% | 26% | 143% |
| Q238H, M291V | 1383 | 109% | 22% | 119% |
| M291V | 1618 | 123% | 22% | 118% |
| G151D, M291V | 1302 | 105% | 21% | 114% |
| T135M, M291V | 1265 | 100% | 18% | 101% |

Example 4: Saturation Library Prepared Using AAR (S18W) as a Template

A full saturation library of an acyl-ACP reductase variant from Synechococcus elongatus PCC7942 ("AAR(S18W)_7942"), was built and screened for variants that showed improvements over AAR (S18W), identified as a significantly improved AAR variant in the first round of screening (Examples 2 and 3). The selection criteria was an increase in FALC titer or an increase in the percent fraction of C12. Engineering efforts were focused on relieving the dependence of AAR on ACP overexpression in order to yield high titers. While not wishing to be bound by theory, the advantage observed in strains overexpressing ACP was hypothesized to result from a higher concentration of fatty acid biosynthesis intermediates available for cleavage by AAR. By screening saturation and combination libraries built on AAR in a strain lacking ACP overexpression (having a lower concentration of FAS intermediates), variants with higher affinities for FAS intermediates could be selected.

The plasmid that used to make the full saturation library was designated pAAR-1. It is a derivative of pLS9-185 harboring the AAR gene encoding the (S18W) variant followed by the aldehyde reductase gene, AlrA, from Acinetobacter baylyi (SEQ ID NO: 54). AlrA was added to fully reduce fatty aldehyde intermediates generated by AAR and not fully reduced by E. coli's endogenous fatty aldehyde reductases. The full saturation library was screened in strain Shu.002. Strain Shu.002 is DV2 PT5-ifab138 PT5_ifadR (Table 7, infra). For ifab138 see SEQ ID NO: 55 in Table 10. The libraries were screened using one of the standard protocols described above. The improvements were classified as either improving titer or increasing the fraction of C12 fatty alcohols produced by the acyl-ACP reductase without significantly affecting titer. The results from screening saturation libraries are shown in Table 5 below.

TABLE 5

Mutations From an AAR (S18W) 7942 Full Saturation Library Correlated with Increased Fatty Alcohol Titer and/or Increased C12 Fatty Alcohol Fraction

| AAR mutations | FALC Titer* | | C12 | |
|---|---|---|---|---|
| (in addition to S18W) | Total* | FIOC** | Fraction* | FIOC** |
| T148V | 747 | 1.21 | 7.9% | 0.99 |
| A159V | 702 | 1.14 | 7.0% | 0.87 |
| T157V | 674 | 1.10 | 7.2% | 0.90 |
| A135S | 803 | 1.31 | 7.8% | 0.98 |
| A328S | 712 | 1.16 | 8.1% | 1.02 |
| Q191A | 780 | 1.27 | 7.7% | 0.96 |
| A285V, M291V | 837 | 1.36 | 8.0% | 1.00 |
| Q277V | 854 | 1.39 | 7.9% | 0.99 |
| Q155C | 626 | 1.02 | 8.3% | 1.04 |
| E210Y | 676 | 1.10 | 8.5% | 1.06 |

TABLE 5-continued

Mutations From an AAR (S18W) 7942 Full Saturation Library Correlated with Increased Fatty Alcohol Titer and/or Increased C12 Fatty Alcohol Fraction

| AAR mutations (in addition to S18W) | FALC Titer* Total* | FIOC** | C12 Fraction* | FIOC** |
|---|---|---|---|---|
| T120S | 623 | 1.01 | 8.1% | 1.02 |
| T236C | 691 | 1.12 | 7.6% | 0.95 |
| Q335N | 763 | 1.24 | 6.8% | 0.86 |
| C172L | 700 | 1.14 | 7.7% | 0.97 |
| E283S | 858 | 1.39 | 8.0% | 1.00 |
| L209R | 837 | 1.36 | 7.6% | 0.96 |
| I153P | 606 | 0.99 | 8.0% | 1.00 |
| A211W | 797 | 1.30 | 6.9% | 0.86 |
| A324T | 909 | 1.48 | 4.0% | 0.50 |
| W34F | 817 | 1.22 | 7.5% | 0.98 |
| T187V | 825 | 1.23 | 6.9% | 0.91 |
| D24E | 737 | 1.10 | 7.1% | 0.93 |
| T188H | 862 | 1.29 | 8.6% | 1.13 |
| V18A | 798 | 1.19 | 6.4% | 0.84 |
| V18A, L338W | 732 | 1.27 | 7.6% | 0.97 |
| T188V | 775 | 1.34 | 7.4% | 0.95 |
| I168V | 731 | 1.27 | 8.1% | 1.03 |
| W35F | 666 | 1.15 | 7.5% | 0.96 |
| T148V | 836 | 1.45 | 6.2% | 0.80 |
| Q155L | 740 | 1.28 | 8.5% | 1.08 |
| T148C | 731 | 1.26 | 8.6% | 1.10 |
| T148E | 694 | 1.20 | 8.3% | 1.06 |
| A50Q, L337V | 800 | 1.38 | 7.2% | 0.92 |
| R118Q | 724 | 1.25 | 7.3% | 0.94 |
| L31V | 901 | 1.56 | 6.8% | 0.87 |
| A135S | 775 | 1.34 | 8.7% | 1.12 |
| D24Y | 890 | 0.93 | 19.1% | 2.05 |
| C63A | 895 | 0.94 | 16.1% | 1.73 |
| S113K | 812 | 0.85 | 13.3% | 1.43 |
| L31V | 645 | 0.68 | 15.7% | 1.69 |
| E283G | 917 | 0.96 | 14.3% | 1.54 |
| A112R | 918 | 0.96 | 10.7% | 1.15 |
| D43E | 1002 | 1.05 | 13.0% | 1.39 |
| Q116G | 894 | 0.94 | 14.0% | 1.50 |
| S86G | 849 | 0.89 | 13.4% | 1.44 |

*Average from 4 replicates
**FIOC = fold increase over AAR (S18W) control

Example 5: Combination Libraries Prepared Using AAR (S18W) as a Template

Standard techniques known to those of skill in the art were used to prepare combination libraries. The mutations tested in combination libraries (Tables 6A, 6B and 6C) were originally identified in the full saturation library (Example 4). The combination libraries were constructed in the same plasmid and screened in the same strain as described in Example 3. The libraries were screened using one of the standard protocols described above. The improvements were classified as either improving titer or increasing the fraction of C12 fatty alcohols produced by the acyl-ACP reductase without significantly affecting titer. The results from screening AAR combination libraries are shown in Tables 6A, 6B and 6C below.

TABLE 6A

Mutations from the 1$^{st}$ AAR(S18W)_7942 Combination Library Correlated with Increased Fatty Alcohol Titer

| AAR mutations (in addition to S18W) | FALC Titer* mg/L* | FIOC** | C12 Fraction* | FIOC** |
|---|---|---|---|---|
| A281L | 1478 | 1.29 | 14.1% | 1.11 |
| A281Y | 1527 | 1.28 | 12.1% | 0.96 |
| T154A, A281L | 1550 | 1.28 | 14.3% | 1.13 |
| T154A, A281Y | 1384 | 1.19 | 13.3% | 1.05 |
| C63G, A281F | 1472 | 1.24 | 12.9% | 1.02 |
| C63G, A281L | 1432 | 1.19 | 18.2% | 1.44 |
| N83G, A281Y | 1428 | 1.23 | 10.7% | 0.84 |
| C63G, A281Y | 1419 | 1.21 | 15.6% | 1.24 |
| S10G, A281L | 1419 | 1.20 | 12.6% | 1.00 |
| S113K, Q155G | 1305 | 1.15 | 12.3% | 0.97 |
| D43E, A50Q, A281L | 1517 | 1.32 | 9.1% | 0.72 |
| M21L, N83G, A281Y | 1513 | 1.29 | 10.2% | 0.81 |
| M21L, S113K, A281L | 1392 | 1.20 | 20.4% | 1.61 |
| C63G, T154A, A281F | 1369 | 1.24 | 12.4% | 0.98 |
| C63G, N83G, A281Y | 1330 | 1.32 | 14.6% | 1.16 |
| Q155G, A281L, E283G | 1327 | 1.16 | 22.2% | 1.76 |
| A50Q, C63G, A281F | 1286 | 1.15 | 17.9% | 1.41 |
| S18W, D43E, A50Q, A281L | 1635 | 1.32 | 9.4% | 0.77 |
| M21L, C63G, S113K, T154A A281L | 1518 | 1.24 | 28.3% | 2.23 |
| M21L, L31V, N83G, Q116G A281L | 1353 | 1.18 | 15.3% | 1.21 |

*Average of 4 replicates
**FIOC = fold increase over (S18W) control

TABLE 6B

Mutations from the 2$^{nd}$ AAR(S18W)_7942 Combination Library Correlated with Increased Fatty Alcohol Titer

| AAR mutations (in addition to S18W) | FALC Titer* mg/L* | FIOC** | C12 Fraction* | FIOC** |
|---|---|---|---|---|
| S18W (control) | 1034 | 1.00 | 10.0% | 1.00 |
| M21L, C63G, S113K, T154A, A281L | 1179 | 1.14 | 29.4% | 2.94 |
| D16L, M21L, C63G, S113K, T154A, A281L | 1221 | 1.18 | 19.4% | 1.94 |
| L8A, D24V, C63G, S113K, Q155L, A281L | 1414 | 1.37 | 10.4% | 1.04 |
| L8A, M21L, C63G, A77A***, S113K, T154A A281L | 1310 | 1.27 | 14.2% | 1.42 |
| D24P, L31M, C63G, S113K, T154A, A281L | 1437 | 1.39 | 13.0% | 1.30 |
| L8A, D16L, D24V, C63G, S113K, T154A A281L | 1342 | 1.30 | 12.0% | 1.20 |
| D24E, C63G, S113K, T154A, A281L | 1425 | 1.38 | 14.3% | 1.43 |

*Average from 4 replicates
**FIOC = fold increase over (S18W) control
***A77A mutation is a gcc to gca silent codon mutation

TABLE 6C

Mutations from the AAR (S18W)_7942 Combination Libraries
Correlated with Increased Fraction of C12 Fatty Alcohol

| AAR mutations (in addition to S18W) | C12 Fraction* | FIOC** | FALC Titer* FIOC** |
|---|---|---|---|
| S18W (control) | 11.0% | 1.00 | 1.00 |
| M21L, C63G, S113K, T154A, A281L | 28.3% | 2.57 | 1.24 |
| M21L, Q155G, A281L | 24.8% | 2.25 | 1.10 |
| Q155G, A281L, E283G | 22.2% | 2.02 | 1.16 |
| M21L, S113K, A281L | 20.4% | 1.85 | 1.20 |
| C63G, A281L | 18.1% | 1.65 | 1.18 |
| A50Q, C63G, A281F | 17.9% | 1.63 | 1.15 |
| C63G | 17.7% | 1.61 | 1.00 |
| S10G, C63G, Q155G, S253N, A281F | 16.1% | 1.46 | 1.03 |
| D43E, C63G, S113K, A281L | 16.0% | 1.46 | 0.98 |
| A281L | 15.6% | 1.42 | 1.20 |
| M21L, L31V, N83G, Q116G, A281L | 15.3% | 1.39 | 1.18 |
| C63G, N83G, A281Y | 14.6% | 1.33 | 1.32 |
| A281L | 14.1% | 1.28 | 1.29 |

*Average from 4 replicates
**FIOC = fold increase over (S18W) control

Example 6: Increased Flux Through the Fatty Acid Synthesis Pathway—iFab and iFadR Mediated Fatty Alcohol Production Using AAR In this example, improved fatty alcohol production using AAR was shown by increasing flux through the fatty acid biosynthesis pathway mediated by the overexpression of a synthetic operon comprising several FAB proteins (ifab138) and/or overexpression of FadR protein (ifad), a regulator of fatty acid metabolism. iFAB138 (SEQ ID NO:55) includes in the following order the genes fabV from *Vibrio cholerae*, FabH, fabD, fabG and fabA from *Salmonella typhimurium*, and FabF from *Clostridium acetobutylicum*, and it is integrated as a synthetic operon controlled either by the PlacUV5 or PT5 promoter. iFadR includes the fadR gene from *Escherichia coli* (SEQ ID NO:56) controlled by the T5 promoter. The components present in the *E. coli* strains evaluated in this example are shown in Table 7, below.

TABLE 7

*E. coli* Strains with iFAB138 or fadR

| Components | DV2 | BD061 | BD064 | Shu002 |
|---|---|---|---|---|
| i(PlacUV5-fab138) | − | + | + | − |
| i(PT5-fab138) | − | − | − | + |
| i(PT5-fadR) | − | − | + | + |

Figure 7:
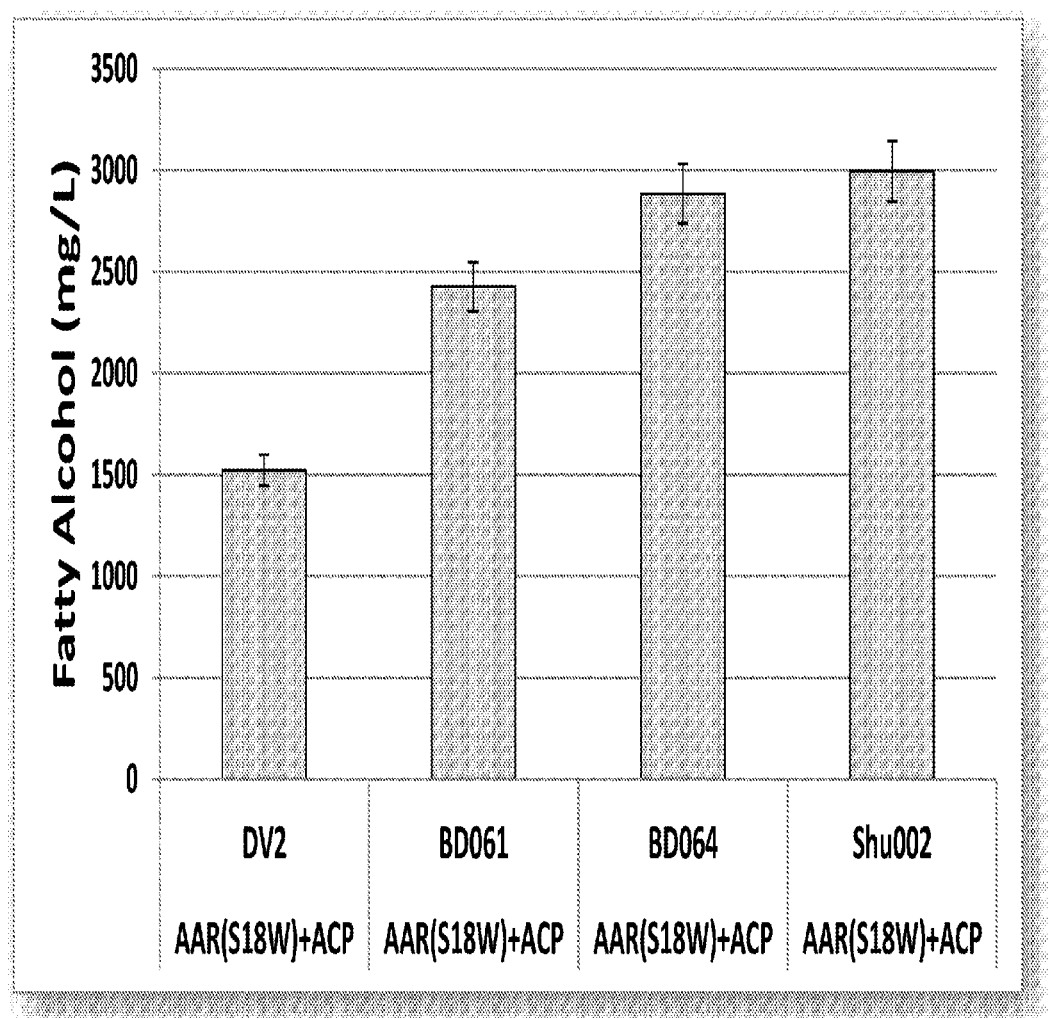
FIG. 7 presents results that illustrate improved fatty alcohol production of recombinant host cells that rely on AAR-mediated by ifab and ifadR overexpression.

AAR (S18W) was expressed from plasmid pDS311, a variant of plasmid pDS171S, in which AAR codon 18 specified a tryptophan instead of a serine (pCL-AAR (S18W)+ACP-sfp) and the aldehyde reductase gene, alrA, from *Acinetobacter baylyi* (SEQ ID NO: 54) was cloned downstream of the sfp gene from *B. subtilis*. pDS311 was transformed into strains DV2, BD061, BD064 and Shu002. The strains were evaluated in the 4NBT_2N protocol (see above). As shown in FIG. 7, fatty alcohol production significantly increased as a result of the presence of ifab138 and ifadR, with strain Shu002 showing the highest fatty alcohol titer.

Figure 8:
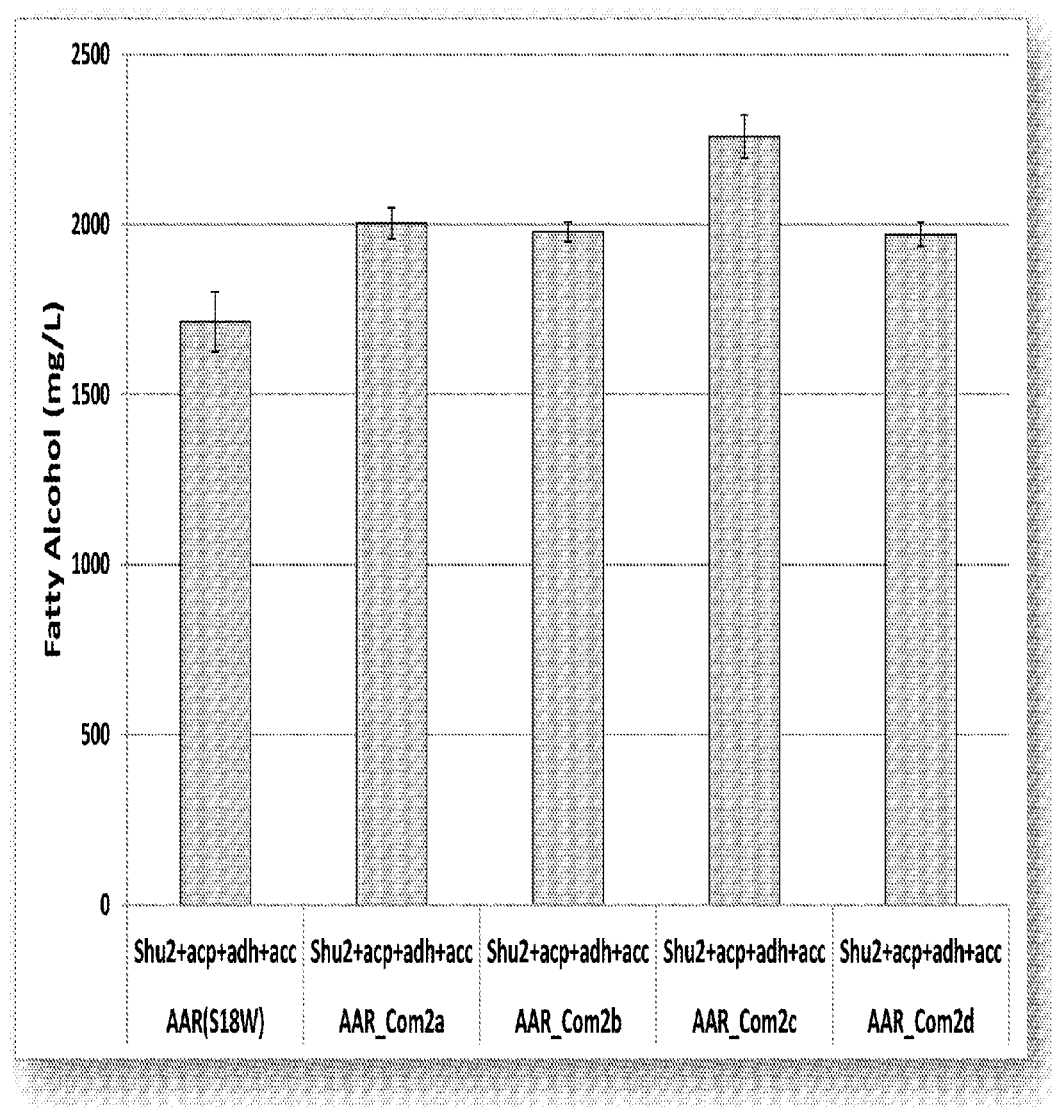
FIG. 8 presents results showing elevated fatty alcohol levels in recombinant host cells that express AAR_7942 variants derived from combination libraries (AAR_Com 2a-d) which are coexpressed with ACP, AlrA (alcohol dehydrogenase (ADH)) and a synthetic acc operon in strain Shu2. A number of alcohol dehydrogenase polypeptides are useful in accordance with the disclosure and include, but are not limited to AlrA of *Acinetobacter* sp. M-1 (SEQ ID NO: 52) and an AlrA homolog such as AlrAadp1 (SEQ ID NO: 53)
Figure 9A:
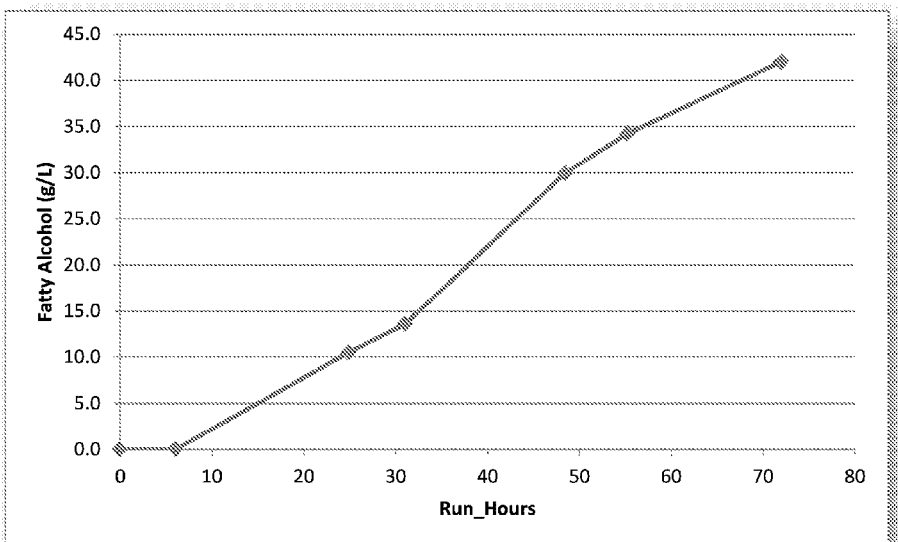
FIGS. 9A and 9B present results from a tank fermentation of AAR_7942 variant S18W that illustrate FALC titer (9A) and yield on glucose (9B) showing that expression of AAR_7942 variant S18W results in altered activity and chain length distribution.
Figure 9B:
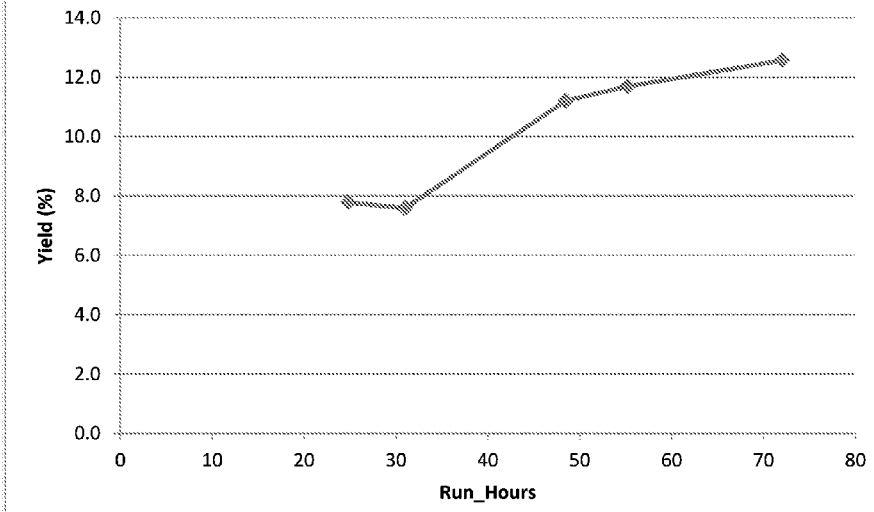

Example 7: Improved AAR Variants in a Strain with Increased Flux Through the Fatty Acid Synthesis Pathway In this example, improved fatty alcohol production in recombinant host cells transformed with AAR variants from combination libraries was demonstrated in Shu2, an *E. coli* strain with increased flux through the fatty acid biosynthesis pathway mediated by the overexpression of the ifab138 and overexpression of FadR protein (supra). Four AAR variants from the second combination library (Table 6B) were evaluated. These variants harbor the following mutations: Com2a: S18W, D24P, L31M, C63G, S113K, T154A, A281L; Comb2b: S18W, D16L, M21L, C63G, S113K, T154A, A281L; Com2c: S18W, L8A, M21L, C63G, A77A, S113K, T154A, A281L; Com2d: D24E, C63G, S113K, T154A, A281L (see also FIG. 8). These variants were cloned into the backbone of plasmid pJL104. pJL104 was created by cloning the synthetic accD+ operon from *C. glutamicum* (as described in Example 2, supra) downstream of the alrA gene in pDS311. The resulting plasmids were transformed into strain Shu002 and the strains were evaluated in the 4NBT_1N protocol (supra). As shown in FIG. 8, elevated fatty alcohol production was observed in all strains. Strain BD064 harboring plasmid pDS311, which expresses the S18W variant of AAR_7942, was also evaluated in tank fermentations. The strain produced fatty alcohols with a maximum titer of 42 g/L, a yield of 12.6% (on glucose) and a productivity of 0.62 g/L/h as shown in FIG. 9. The chain length distribution of the fatty alcohols was as follows: 1.2% C8, 7.7% C10, 26.9% C12, 44.7% C14, 16.0% C16 and 1.9% C18. The fraction of saturated and unsaturated fatty alcohols was 72.6% and 27.4%, respectively.

Example 8: Increased MED4 Acyl Aldehyde Reductase (AAR) Activity and Redistribution of Chain Length Selectivity for C14 Fatty Alcohol Production AAR is one of the components essential for cyanobacterial alkane biosynthesis, another essential component is an aldehyde decarbonylase (ADC). The inventors discovered that the *Prochlorococcus marinus* MED4_AAR is catalytically inactive without the presence of MED4_ADC, i.e., when only MED4_AAR is expressed in *E. coli* no products are detected, and when MED4_AAR and ADC are coexpressed in *E. coli* the only products detected are alkanes. The inventors also discovered that when MED4_AAR is coexpressed in *E. coli* with an apparently catalytically inactive variant of MED4_ADC in which histidine 156 is replaced by arginine (referred to subsequently as MED4_ADC (H165R)), fatty alcohols, and no alkanes are detected (see FIG. 10). It was concluded from this data that MED4_AAR requires physical interaction with MED4_ADC to be catalytically active. The inventors used this system to identify MED4_AAR variants with increased activity and/or altered substrate specificity for purposes of FALC production.

MED4_ADC(H156R) was expressed together with a full saturation library of MED4_AAR. The MED4_AAR saturation library was prepared in a plasmid pCL1920-derivative (pLS9-195) and introduced into a production strain carrying plasmid pGLAK-043 (which is plasmid pACYC-Ptrc-MED4_ADC harboring the H156R mutation in the ADC gene). The clones were induced and AAR variants were selected based upon production of more fatty alcohol than the wild type AAR enzyme or the ability to produce fatty alcohols with an altered chain length profile, e.g., an increased fraction of C14 fatty alcohol. Selected clones were then re-tested in a validation round. All variants that showed consistent FALC titers amongst the primary and secondary fermentations were re-grown, plasmid DNA was isolated, sequenced and re-introduced into the parental production strain for further testing. These new transformants were then subjected to another confirmatory fermentation and analysis. Table 8 below shows representative data from 16 AAR variants that produced the highest FALC titers (ordered from top to bottom in descending activity). The variants ranged from 1.4-fold to 2.2 fold over wild type. These variants showed the ability to increase MED4_AAR activity using directed evolution techniques and furthermore form the basis for further improvements.

TABLE 8

FALC Productivity of MED4 AAR Mutants Relative to the Wild Type (WT) MED4 AAR

| AAR Mutation | Fold FALC increase over Wild Type |
|---|---|
| V346P | 2.2 |
| Q40V | 2.2 |
| A345R | 2.1 |
| L344S | 2.1 |
| D61E | 2.1 |
| V346G | 2.0 |
| L344D | 1.9 |
| G52V | 1.9 |
| A345* | 1.9 |
| L344T | 1.8 |
| K303G | 1.8 |
| L344A | 1.8 |
| H340P | 1.6 |
| S588V | 1.5 |
| K339L | 1.4 |
| G273E | 1.4 |

*Truncated variant missing the last two amino acids.

The data set was also scanned for AAR variants which displayed altered chain length profiles. The most common species produced by the wild type AAR has a chain length of C16. An increased proportion of FALC species with chain lengths shorter than C16 is of interest. Two variant clones were identified that showed an approximately 3-fold increase in the quantity of C14 FALC (FIG. 10). The sequencing of these clones revealed that they were identical D61E mutants with the same nucleotide codon sequence. The plasmid DNA for the D61E variant was reintroduced into the parental strain containing the H156R ADC. The results show that expression of the D61E variant of AAR in a recombinant host cell skews the chain length distribution of FALC species toward shorter carbon chains. Table 9 below illustrates the FALC chain length distribution produced by recombinant host cells expressing the D61E variant of MED4_AAR compared to wild type (WT) MED4_AAR and the V346P variant of MED4_AAR which did not produce any products with altered chain lengths.

TABLE 9

Chain length distribution for AAR variants and wild type AAR

| | Fatty Alcohol | | |
|---|---|---|---|
| MED4 AAR/ADC | C14% | C16% | C18% |
| AAR WT/ADC(H156R) | 6 | 92 | 2 |
| AAR(D61E)/ADC(H156R) | 14* | 85 | 0 |
| AAR(V346P)/ADC(H156R) | 4 | 92 | 4 |
| AAR WT/ADC WT | ND | ND | ND |
| AAR(D61E)/ADC WT | ND | ND | ND |
| AAR(V346P)/ADC WT | ND | ND | ND |

ND = not detected
*1% variance attributable to deviations from averaging

These variants can be further recombined and screened for improvements in the MED4_ADC (H156R) background. The MED4_AAR (D61E) variant and further mutated progeny may be useful to decrease the average chain length of both fatty alcohols and alkanes. The MED4_AAR (D61E) variant demonstrates that MED4_AAR chain-length specificity is malleable and presents the possibility for further improvement of this activity through additional protein engineering efforts. All variants described were sequenced from progeny of pLS9-195 and contained codon mutations corresponding to the listed amino acid substitutions.

TABLE 10

Names Related to Sequence Listing

| SEQ ID NO | Type | Name |
|---|---|---|
| 1 | nucleic acid seq. | *Nostoc punctiforme* PCC 73102_acp Accession# YP_001867863 |
| 2 | amino acid seq. | *Nostoc punctiforme* PCC 73102_acp Accession# YP_001867863 |
| 3 | nucleic acid seq. | *Synechocystis* sp. PCC 6803_acp Accession # NP_440632.1 |
| 4 | amino acid seq. | *Synechocystis* sp. PCC 6803_acp Accession # NP_440632.1 |
| 5 | nucleic acid seq. | *Prochlorococcus marinus* subsp. *pastoris* str. CCMP1986_acp Accession# NP_893725.1 |
| 6 | amino acid seq. | *Prochlorococcus marinus* subsp. *pastoris* str. CCMP1986_acp Accession# NP_893725.1 |
| 7 | nucleic acid seq. | *Synechococcus elongatus* PCC 7942_acp Accession# YP_399555 |
| 8 | amino acid seq. | *Synechococcus elongatus* PCC 7942_acp Accession# YP_399555 |
| 9 | nucleic acid seq. | *Nostoc* sp. PCC 7120_acp Accession# NP_487382.1 |
| 10 | amino acid seq. | *Nostoc* sp. PCC 7120_acp Accession# NP_487382.1 |
| 11 | nucleic acid seq. | *B. subtilis* sfp (synthesized) as in accession# X63158.1 |
| 12 | amino acid seq. | *B. subtilis* sfp (synthesized) as in accession# X63158.1 |
| 13 | primer seq. | 168IFF |
| 14 | primer seq. | 168IFR |
| 15 | primer seq. | 169IFF |
| 16 | primer seq. | 169IFR |
| 17 | primer seq. | 170IFF |
| 18 | primer seq. | 170IFR |

TABLE 10-continued

Names Related to Sequence Listing

| SEQ ID NO | Type | Name |
|---|---|---|
| 19 | primer seq. | 171IFF |
| 20 | primer seq. | 171IFR |
| 21 | primer seq. | 172IFF |
| 22 | primer seq. | 172IFR |
| 23 | primer seq. | 168SIFF |
| 24 | primer seq. | 170S1FF |
| 25 | primer seq. | 171SIFF |
| 26 | primer seq. | 168SIFR |
| 27 | nucleic acid seq. | *Synechococcus elongatus* PCC7942 YP_400611 (Synpcc7942_1594) Acyl-CoA Reductase (AAR) |
| 28 | nucleic acid seq. | *Synechococcus elongatus* PCC7942 YP_400611 (Synpcc7942_1594) Acyl-CoA Reductase (AAR) |
| 29 | nucleic acid seq. | *Synechocystis* sp. PCC6803 sll0209 (NP_442146) AAR |
| 30 | amino acid seq. | *Synechocystis* sp. PCC6803 sll0209 (NP_442146) AAR |
| 31 | nucleic acid seq. | *Cyanothece* sp. ATCC51142 cce_1430 (YP_001802846) AAR |
| 32 | amino acid seq. | *Cyanothece* sp. ATCC51142 cce_1430 (YP_001802846) AAR |
| 33 | nucleic acid seq. | *Prochlorococcus marinus* CCMP1986 PMM0533 (NP_892651) AAR |
| 34 | amino acid seq. | *Prochlorococcus marinus* CCMP1986 PMM0533 (NP_892651) AAR |
| 35 | nucleic acid seq. | *Gloeobacter violaceus* PCC7421 NP_96091 (gll3145) AAR |
| 36 | amino acid seq. | *Gloeobacter violaceus* PCC7421 NP_96091 (gll3145) AAR |
| 37 | nucleic acid seq. | *Nostoc punctiforme* PCC73102 ZP_00108837 (Npun02004176) AAR |
| 38 | amino acid seq. | *Nostoc punctiforme* PCC73102 ZP_00108837 (Npun02004176) AAR |
| 39 | nucleic acid seq. | *Anabaena variabilis* ATCC29413 YP_323044 (Ava_2534) AAR |
| 40 | amino acid seq. | *Anabaena variabilis* ATCC29413 YP_323044 (Ava_2534) AAR |
| 41 | nucleic acid seq. | *Synechococcus elongatus* PCC6301 YP_170761 (syc0051_d) AAR |
| 42 | amino acid seq. | *Synechococcus elongatus* PCC6301 YP_170761 (syc0051_d) AAR |
| 43 | nucleic acid seq. | *Nostoc* sp. PCC7120 alr5284 (NP_489324) AAR |
| 44 | amino acid seq. | *Nostoc* sp. PCC7120 alr5284 (NP_489324) AAR |
| 45 | nucleic acid seq. | birA from *Corynebacterium glutamicum* (YP_224991) |
| 46 | synthetic DNA | birA from *Corynebacterium glutamicum* (YP_224991) |
| 47 | amino acid seq. | birA from *Corynebacterium glutamicum* (YP_224991) |
| 48 | nucleic acid seq. | accDA1 (dtsK) from *Corynebacterium glutamicum* (YP_224991) |
| 49 | amino acid seq. | accDA1 (dtsR) from *Corynebacterium glutamicum* (YP_224991) |
| 50 | nucleic acid seq. | accCB from *Corynebacterium glutamicum* (YP_224991) |
| 51 | amino acid seq. | accCB from *Corynebacterium glutamicum* (YP_224991) |
| 52 | amino acid seq. | AlrA *Acinetobacter* sp. M-1 |
| 53 | amino acid seq. | AlrAadp1 |
| 54 | amino acid seq. | alrAadp1 *Acinetobacter baylyi* ADP1-WT Protein |
| 55 | nucleic acid seq. | iFAB138 |
| 56 | nucleic acid seq. | FadR from *E. coli* MG1655 (NP_415705) |
| 57 | amino acid seq. | AAR Mutant with mutation S18W (made from *Synechococcus elongatus* PCC7942 YP_400611 (Synpcc7942_1594) Acyl-CoA Reductase (AAR)) |

As is apparent to one with skill in the art, various modifications and variations of the above aspects and embodiments can be made without departing from the spirit and scope of this disclosure. Such modifications and variations are within the scope of this disclosure.

What is claimed is:

1. A variant acyl-ACP reductase (AAR) polypeptide comprising at least 90% sequence identity to the amino acid sequence of SEQ ID NO: 80, wherein said variant AAR polypeptide comprises a mutation at amino acid position 61, wherein the mutation is D61E, and wherein said AAR polypeptide catalyzes the conversion of an acyl-ACP to a fatty aldehyde.

2. The variant AAR polypeptide of claim 1, wherein expression of the variant AAR polypeptide in a recombinant host cell results in a higher titer of a fatty aldehyde or fatty alcohol composition as compared to a titer of a fatty aldehyde or fatty alcohol composition produced by a wild type AAR polypeptide in a corresponding wild type host cell.

3. The variant AAR polypeptide of claim 1, wherein said fatty alcohol composition is a C12, C14 or C16 fatty alcohol composition, or a combination thereof.

4. A recombinant host cell expressing the variant AAR polypeptide of claim 1.

5. The recombinant host cell of claim 4, wherein the recombinant host cell produces a fatty aldehyde or fatty alcohol composition with a titer that is at least 10% greater, at least 15% greater, at least 20% greater, at least 25% greater, or at least 30% greater than the titer of a fatty aldehyde or alcohol composition produced by a host cell expressing a corresponding wild type AAR polypeptide, when cultured in medium containing a carbon source under conditions effective to express the variant AAR polypeptide.

6. The recombinant host cell of claim 5, wherein the fatty alcohol composition is produced at a titer of about 30 g/L to about 250 g/L.

7. The recombinant host cell of claim 6, wherein the fatty alcohol composition is released from the cell.

8. A cell culture comprising the recombinant host cell of claim 4.

9. The cell culture of claim 8, wherein the fatty alcohol composition comprises one or more of a C6, C8, C10, C12, C13, C14, C15, C16, C17, and a C18 fatty alcohol.

10. The cell culture of claim 9, wherein the fatty alcohol composition comprises one or more of a C10:1, C12:1, C14:1, C16:1, and a C18:1 unsaturated fatty alcohol.

11. The cell culture of claim 9, wherein the fatty alcohol composition comprises an unsaturated fatty alcohol.

12. The cell culture of claim 9, wherein the fatty alcohol composition comprises a fatty alcohol having a double bond at position 7 in the carbon chain between $C_7$ and $C_8$ from the reduced end of the fatty alcohol.

13. The cell culture of claim 9, wherein the fatty alcohol composition comprises a saturated fatty alcohol.

14. A method of producing a fatty alcohol composition having an increase in titer, comprising: culturing the host cell of claim 4 with a carbon source; and harvesting a fatty alcohol composition.

15. The method of claim 14, wherein the titer of the fatty alcohol is at least 20% to 30% greater than the titer of a fatty alcohol composition produced by a wild-type AAR-expressing host cell.

16. The method of claim 14, wherein said fatty alcohol composition has an increased fraction of C14 fatty alcohols.

* * * * *

```
                        SEQUENCE LISTING

<160> NUMBER OF SEQ ID NOS: 80

<210> SEQ ID NO 1
<211> LENGTH: 255
<212> TYPE: DNA
<213> ORGANISM: Nostoc punctiforme

<400> SEQUENCE: 1
atgagccaaa cggaactttt tgaaaaggtc aagaaaatcg tcatcgaaca actgagtgtt      60
gaagatgctt ccaaaatcac tccacaagct aagtttatgg aagatttagg agctgattcc     120
ctggatactg ttgaactcgt gatggctttg gaagaagaat tgatatcga aattcccgac      180 gaagctgccg agcagattgt atcggttcaa gacgcagtag attacatcaa taacaaagtt     240
gctgcatcag cttaa                                                      255
```

```
<210> SEQ ID NO 2
<211> LENGTH: 84
<212> TYPE: PRT
<213> ORGANISM: Nostoc punctiforme

<400> SEQUENCE: 2

Met Ser Gln Thr Glu Leu Phe Glu Lys Val Lys Lys Ile Val Ile Glu
1               5                   10                  15

Gln Leu Ser Val Glu Asp Ala Ser Lys Ile Thr Pro Gln Ala Lys Phe
            20                  25                  30

Met Glu Asp Leu Gly Ala Asp Ser Leu Asp Thr Val Glu Leu Val Met
        35                  40                  45

Ala Leu Glu Glu Glu Phe Asp Ile Glu Ile Pro Asp Glu Ala Ala Glu
    50                  55                  60

Gln Ile Val Ser Val Gln Asp Ala Val Asp Tyr Ile Asn Asn Lys Val
65                  70                  75                  80

Ala Ala Ser Ala

<210> SEQ ID NO 3
<211> LENGTH: 234
<212> TYPE: DNA
<213> ORGANISM: Synechocystis sp.

<400> SEQUENCE: 3
atgaatcagg aaattttga  aaaagtaaaa aaaatcgtcg tggaacagtt ggaagtggat    60
cctgacaaag tgacccccga tgccaccttt gccgaagatt taggggctga ttccctcgat   120
acagtggaat tggtcatggc cctggaagaa gagtttgata ttgaaattcc cgatgaagtg   180
gcggaaacca ttgataccgt gggcaaagcc gttgagcata tcgaaagtaa ataa          234

<210> SEQ ID NO 4
<211> LENGTH: 77
<212> TYPE: PRT
<213> ORGANISM: Synechocystis sp.

<400> SEQUENCE: 4

Met Asn Gln Glu Ile Phe Glu Lys Val Lys Lys Ile Val Val Glu Gln
1               5                   10                  15

Leu Glu Val Asp Pro Asp Lys Val Thr Pro Asp Ala Thr Phe Ala Glu
            20                  25                  30

Asp Leu Gly Ala Asp Ser Leu Asp Thr Val Glu Leu Val Met Ala Leu
        35                  40                  45

Glu Glu Glu Phe Asp Ile Glu Ile Pro Asp Glu Val Ala Glu Thr Ile
    50                  55                  60

Asp Thr Val Gly Lys Ala Val Glu His Ile Glu Ser Lys
65                  70                  75

<210> SEQ ID NO 5
<211> LENGTH: 243
<212> TYPE: DNA
<213> ORGANISM: Prochlorococcus marinus

<400> SEQUENCE: 5
atgtcacaag aagaaatcct tcaaaaagta tgctctattg tttctgagca actaagtgtt    60
gaatcagccg aagtaaaatc tgattcaaac tttcaaaatg atttaggtgc agactcccta   120
gacaccgtag agctagttat ggctcttgaa gaagcatttg atatcgagat acctgatgaa   180
gcagctgaag gtatcgcaac agtaggagat gctgttaaat tcatcgaaga aaaaaaggt    240
```

```
taa                                                                  243

<210> SEQ ID NO 6
<211> LENGTH: 80
<212> TYPE: PRT
<213> ORGANISM: Prochlorococcus marinus

<400> SEQUENCE: 6

Met Ser Gln Glu Glu Ile Leu Gln Lys Val Cys Ser Ile Val Ser Glu
1               5                   10                  15

Gln Leu Ser Val Glu Ser Ala Glu Val Lys Ser Asp Ser Asn Phe Gln
            20                  25                  30

Asn Asp Leu Gly Ala Asp Ser Leu Asp Thr Val Glu Leu Val Met Ala
        35                  40                  45

Leu Glu Glu Ala Phe Asp Ile Glu Ile Pro Asp Glu Ala Ala Glu Gly
    50                  55                  60

Ile Ala Thr Val Gly Asp Ala Val Lys Phe Ile Glu Glu Lys Lys Gly
65                  70                  75                  80

<210> SEQ ID NO 7
<211> LENGTH: 243
<212> TYPE: DNA
<213> ORGANISM: Synechococcus elongatus

<400> SEQUENCE: 7
atgagccaag aagacatctt cagcaaagtc aaagacattg tggctgagca gctgagtgtg    60
gatgtggctg aagtcaagcc agaatccagc ttccaaaacg atctgggagc ggactcgctg   120
gacaccgtgg aactggtgat ggctctggaa gaggctttcg atatcgaaat ccccgatgaa   180
gccgctgaag gcattgcgac cgttcaagac gccgtcgatt tcatcgctag caaagctgcc   240
tag                                                                  243

<210> SEQ ID NO 8
<211> LENGTH: 80
<212> TYPE: PRT
<213> ORGANISM: Synechococcus elongatus

<400> SEQUENCE: 8

Met Ser Gln Glu Asp Ile Phe Ser Lys Val Lys Asp Ile Val Ala Glu
1               5                   10                  15

Gln Leu Ser Val Asp Val Ala Glu Val Lys Pro Glu Ser Ser Phe Gln
            20                  25                  30

Asn Asp Leu Gly Ala Asp Ser Leu Asp Thr Val Glu Leu Val Met Ala
        35                  40                  45

Leu Glu Glu Ala Phe Asp Ile Glu Ile Pro Asp Glu Ala Ala Glu Gly
    50                  55                  60

Ile Ala Thr Val Gln Asp Ala Val Asp Phe Ile Ala Ser Lys Ala Ala
65                  70                  75                  80

<210> SEQ ID NO 9
<211> LENGTH: 255
<212> TYPE: DNA
<213> ORGANISM: Nostoc sp.

<400> SEQUENCE: 9
atgagccaat cagaaacttt tgaaaaagtc aaaaaaattg ttatcgaaca actaagtgtg    60
gagaaccctg acacagtaac tccagaagct agttttgcca acgatttaca ggctgattcc   120
ctcgatacag tagaactagt aatggctttg gaagaagaat ttgatatcga aattcccgat   180
```

```
gaagccgcag agaaaattac cactgttcaa gaagcggtgg attacatcaa taaccaagtt    240
gccgcatcag cttaa                                                    255
```

<210> SEQ ID NO 10
<211> LENGTH: 84
<212> TYPE: PRT
<213> ORGANISM: Nostoc sp.

<400> SEQUENCE: 10

```
Met Ser Gln Ser Glu Thr Phe Glu Lys Val Lys Ile Val Ile Glu
1               5                   10                  15

Gln Leu Ser Val Glu Asn Pro Asp Thr Val Thr Pro Glu Ala Ser Phe
            20                  25                  30

Ala Asn Asp Leu Gln Ala Asp Ser Leu Asp Thr Val Glu Leu Val Met
        35                  40                  45

Ala Leu Glu Glu Glu Phe Asp Ile Glu Ile Pro Asp Glu Ala Ala Glu
    50                  55                  60

Lys Ile Thr Thr Val Gln Glu Ala Val Asp Tyr Ile Asn Asn Gln Val
65                  70                  75                  80

Ala Ala Ser Ala
```

<210> SEQ ID NO 11
<211> LENGTH: 674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgaagattt acggaattta tatggaccgc ccgctttcac aggaagaaaa tgaacggttc    60
atgactttca tatccctga aaaacgggag aaatgccgga gatttatca taaagaagat    120 gctcaccgca ccctgctggg agatgtgctc gttcgctcag tcataagcag gcagtatcag    180
ttggacaaat ccgatatccg ctttagcacg caggaatacg ggaagccgtg catccctgat    240
cttcccgacg ctcatttcaa catttctcac tccggccgct gggtcattgg tgcgtttgat    300
tcacagccga tcggcataga tatcgaaaaa acgaaaccga tcagccttga gatcgccaag    360
cgcttctttt caaaaacaga gtacagcgac cttttagcaa agacaaggca cgagcagaca    420 gactatttt atcatctatg gtcaatgaaa gaaagcttta tcaaacagga aggcaaaggc    480
ttatcgcttc cgcttgattc cttttcagtg cgcctgcatc aggacggaca agtatccatt    540
gagcttccgg acagccattc cccatgctat atcaaaacgt atgaggtcga tcccggctac    600
aaaatggctg tatgcgccgc acaccctgtt tccccgagga tatcacaatg gtctcgtacg    660
aagagctttt ataa                                                    674
```

<210> SEQ ID NO 12
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Lys Ile Tyr Gly Ile Tyr Met Asp Arg Pro Leu Ser Gln Glu Glu
1               5                   10                  15
```

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
 50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
210                 215                 220

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcaatttga gaatttaagg aggaaaacaa aatgagccaa gaagacatct tc            52

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccaagcttc gaattcctag gcagctttgc tag                                 33

<210> SEQ ID NO 15
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcaatttga gaatttaagg aggaaaacaa aatgaatcag gaaattttg aaaaag         56

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
cccaagcttc gaattcttat ttactttcga tatgctcaac g                            41

<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ggcaatttga gaatttaagg aggaaaacaa aatgtcacaa gaagaaatcc ttc               53

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
cccaagcttc gaattcttaa ccttttttttt cttcgatgaa tttaac                      46

<210> SEQ ID NO 19
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
ggcaatttga gaatttaagg aggaaaacaa aatgagccaa acggaacttt ttg               53

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cccaagcttc gaattcttaa gctgatgcag caactttg                                38

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ggcaatttga gaatttaagg aggaaaacaa aatgagccaa tcagaaactt ttg               53

<210> SEQ ID NO 22

```
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cccaagcttc gaattcttaa gctgatgcgg caac                                34

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agctgcctag gaatttaagg aggaataaac catgaagatt tac                      43

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaaaggttaa gaatttaagg aggaataaac catgaagatt tac                      43

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atcagcttaa gaatttaagg aggaataaac catgaagatt tac                      43

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccaagcttc gaattcttat aaaagctctt cgtacgagac c                        41

<210> SEQ ID NO 27
<211> LENGTH: 1029
<212> TYPE: DNA
<213> ORGANISM: Synechococcus elongatus

<400> SEQUENCE: 27
atggcattcg gtcttatcgg tcatctcacc agtttggagc aggcccgcga cgtttctcgc    60
aggatgggct acgacgaata cgccgatcaa ggattggagt tttggagtag cgctcctcct   120
caaatcgttg atgaaatcac agtcaccagt gccacaggca aggtgattca cggtcgctac   180
atcgaatcgt gtttcttgcc ggaaatgctg gcggcgcgcc gcttcaaaac agccacgcgc   240
```

```
aaagttctca atgccatgtc ccatgcccaa aaacacggca tcgacatctc ggccttgggg    300
ggctttacct cgattatttt cgagaatttc gatttggcca gtttgcggca agtgcgcgac    360
actaccttgg agtttgaacg gttcaccacc ggcaatactc acacggccta cgtaatctgt    420
agacaggtgg aagccgctgc taaaacgctg gcatcgaca ttacccaagc gacagtagcg     480
gttgtcggcg cgactggcga tatcggtagc gctgtctgcc gctggctcga cctcaaactg    540
ggtgtcggtg atttgatcct gacggcgcgc aatcaggagc gtttggataa cctgcaggct    600
gaactcggcc ggggcaagat tctgcccttg gaagccgctc tgccggaagc tgactttatc    660
gtgtgggtcg ccagtatgcc tcagggcgta gtgatcgacc cagcaaccct gaagcaaccc    720
tgcgtcctaa tcgacggggg ctaccccaaa aacttgggca gcaaagtcca aggtgagggc    780
atctatgtcc tcaatggcgg ggtagttgaa cattgcttcg acatcgactg gcagatcatg    840
tccgctgcag agatggcgcg gcccgagcgc agatgtttg cctgctttgc cgaggcgatg     900
ctcttggaat ttgaaggctg gcatactaac ttctcctggg gccgcaacca aatcacgatc    960
gagaagatgg aagcgatcgg tgaggcatcg gtgcgccacg gcttccaacc cttggcattg    1020
gcaatttga                                                            1029
```

<210> SEQ ID NO 28
<211> LENGTH: 342
<212> TYPE: PRT
<213> ORGANISM: Synechococcus elongatus

<400> SEQUENCE: 28

```
Met Ala Phe Gly Leu Ile Gly His Leu Thr Ser Leu Glu Gln Ala Arg
1               5                   10                  15

Asp Val Ser Arg Arg Met Gly Tyr Asp Glu Tyr Ala Asp Gln Gly Leu
            20                  25                  30

Glu Phe Trp Ser Ser Ala Pro Pro Gln Ile Val Asp Glu Ile Thr Val
        35                  40                  45

Thr Ser Ala Thr Gly Lys Val Ile His Gly Arg Tyr Ile Glu Ser Cys
    50                  55                  60

Phe Leu Pro Glu Met Leu Ala Ala Arg Arg Phe Lys Thr Ala Thr Arg
65                  70                  75                  80

Lys Val Leu Asn Ala Met Ser His Ala Gln Lys His Gly Ile Asp Ile
                85                  90                  95

Ser Ala Leu Gly Gly Phe Thr Ser Ile Ile Phe Glu Asn Phe Asp Leu
            100                 105                 110

Ala Ser Leu Arg Gln Val Arg Asp Thr Thr Leu Glu Phe Glu Arg Phe
        115                 120                 125

Thr Thr Gly Asn Thr His Thr Ala Tyr Val Ile Cys Arg Gln Val Glu
    130                 135                 140

Ala Ala Ala Lys Thr Leu Gly Ile Asp Ile Thr Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
    210                 215                 220

Ser Met Pro Gln Gly Val Val Ile Asp Pro Ala Thr Leu Lys Gln Pro
```

```
                 225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Val Val Glu His Cys
                260                 265                 270

Phe Asp Ile Asp Trp Gln Ile Met Ser Ala Ala Glu Met Ala Arg Pro
                275                 280                 285

Glu Arg Gln Met Phe Ala Cys Phe Ala Glu Ala Met Leu Leu Glu Phe
                290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
                340

<210> SEQ ID NO 29
<211> LENGTH: 1023
<212> TYPE: DNA
<213> ORGANISM: Synechocystis sp.

<400> SEQUENCE: 29
atgtttggtc ttattggtca tctcacgagt ttagaacacg cccaagcggt tgctgaagat      60
ttaggctatc ctgagtacgc caaccaaggc ctggattttt ggtgttcggc tcctccccaa     120
gtggttgata ttttcaggt gaaaagtgtg acggggcagg tgattgaagg caaatatgtg      180
gagtcttgct ttttgccgga atgttaacc aacggcgga tcaaagcggc cattcgtaaa      240
atcctcaatg ctatggccct ggcccaaaag gtgggcttgg atattacggc cctgggaggc     300
ttttcttcaa tcgtatttga agaatttaac ctcaagcaaa ataatcaagt ccgcaatgtg     360
gaactagatt ttcagcggtt caccactggt aatacccaca ccgcttatgt gatctgccgt     420
caggtcgagt ctggagctaa acagttgggt attgatctaa gtcaggcaac ggtagcggtt     480
tgtggcgcca cgggagatat tggtagcgcc gtatgtcgtt ggttagatag caaacatcaa     540
gttaaggaat tattgctaat tgcccgtaac cgccaaagat tggaaaatct ccaagaggaa     600
ttgggtcggg gcaaaattat ggatttggaa acagccctgc cccaggcaga tattattgtt     660
tgggtggcta gtatgcccaa gggggtagaa attgcggggg aaatgctgaa aaagccctgt     720
ttgattgtgg atggggcta tcccaagaat ttagacacca gggtgaaagc ggatggggtg     780
catattctca aggggggat gtagaacat tcccttgata ttacctggga aattatgaag     840
attgtggaga tggatattcc ctcccggcaa atgttcgcct gttttgcgga ggccattttg     900
ctagagtttg agggctggcg cactaatttt tcctgggggcc gcaaccaaat ttccgttaat     960
aaaatggagg cgattggtga agcttctgtc aagcatggct tttgcccttt agtagctctt    1020
tag                                                                   1023

<210> SEQ ID NO 30
<211> LENGTH: 340
<212> TYPE: PRT
<213> ORGANISM: Synechocystis sp.

<400> SEQUENCE: 30

Met Phe Gly Leu Ile Gly His Leu Thr Ser Leu Glu His Ala Gln Ala
1               5                   10                  15

Val Ala Glu Asp Leu Gly Tyr Pro Glu Tyr Ala Asn Gln Gly Leu Asp
```

|  | 20 |  |  |  | 25 |  |  |  | 30 |  |  |
| --- | --- | --- | --- | --- | --- | --- | --- | --- | --- | --- | --- |

Phe Trp Cys Ser Ala Pro Pro Gln Val Val Asp Asn Phe Gln Val Lys
    35                          40                          45

Ser Val Thr Gly Gln Val Ile Glu Gly Lys Tyr Val Glu Ser Cys Phe
 50                          55                        60

Leu Pro Glu Met Leu Thr Gln Arg Arg Ile Lys Ala Ala Ile Arg Lys
65                         70                        75                    80

Ile Leu Asn Ala Met Ala Leu Ala Gln Lys Val Gly Leu Asp Ile Thr
                      85                        90                        95

Ala Leu Gly Gly Phe Ser Ser Ile Val Phe Glu Glu Phe Asn Leu Lys
                    100                       105                       110

Gln Asn Asn Gln Val Arg Asn Val Glu Leu Asp Phe Gln Arg Phe Thr
            115                       120                       125

Thr Gly Asn Thr His Thr Ala Tyr Val Ile Cys Arg Gln Val Glu Ser
     130                       135                       140

Gly Ala Lys Gln Leu Gly Ile Asp Leu Ser Gln Ala Thr Val Ala Val
145                        150                        155                    160

Cys Gly Ala Thr Gly Asp Ile Gly Ser Ala Val Cys Arg Trp Leu Asp
                    165                       170                       175

Ser Lys His Gln Val Lys Glu Leu Leu Leu Ile Ala Arg Asn Arg Gln
     180                       185                       190

Arg Leu Glu Asn Leu Gln Glu Glu Leu Gly Arg Gly Lys Ile Met Asp
         195                       200                       205

Leu Glu Thr Ala Leu Pro Gln Ala Asp Ile Ile Val Trp Val Ala Ser
   210                       215                       220

Met Pro Lys Gly Val Glu Ile Ala Gly Glu Met Leu Lys Lys Pro Cys
225                        230                        235                    240

Leu Ile Val Asp Gly Gly Tyr Pro Lys Asn Leu Asp Thr Arg Val Lys
                    245                       250                       255

Ala Asp Gly Val His Ile Leu Lys Gly Gly Ile Val Glu His Ser Leu
     260                       265                       270

Asp Ile Thr Trp Glu Ile Met Lys Ile Val Glu Met Asp Ile Pro Ser
       275                       280                       285

Arg Gln Met Phe Ala Cys Phe Ala Glu Ala Ile Leu Leu Glu Phe Glu
       290                       295                       300

Gly Trp Arg Thr Asn Phe Ser Trp Gly Arg Asn Gln Ile Ser Val Asn
305                        310                        315                    320

Lys Met Glu Ala Ile Gly Glu Ala Ser Val Lys His Gly Phe Cys Pro
                    325                       330                       335

Leu Val Ala Leu
     340

<210> SEQ ID NO 31
<211> LENGTH: 1023
<212> TYPE: DNA
<213> ORGANISM: Cyanothece sp.

<400> SEQUENCE: 31

| atgtttggtt | taattggtca | tcttacaagt | ttagaacacg | cccactccgt | tgctgatgcc | 60 |
| tttggctatg | gcccatacgc | cactcaggga | cttgatttgt | ggtgttctgc | tccaccccaa | 120 |
| ttcgtcgagc | attttcatgt | tactagcatc | acaggacaaa | ccatcgaagg | aaagtatata | 180 |
| gaatccgctt | tcttaccaga | aatgctgata | aagcgacgga | ttaaagcagc | aattcgcaaa | 240 |
| atactgaatg | cgatggcctt | tgctcagaaa | aataacctta | acatcacagc | attaggggc | 300 |

```
tttcttcga ttattttga agaatttaat ctcaaagaga atagacaagt tcgtaatgtc      360
tctttagagt ttgatcgctt caccaccgga aacacccata ctgcttatat catttgtcgt      420
caagttgaac aggcatccgc taaactaggg attgacttat cccaagcaac ggttgctatt      480
tgcggggcaa ccggagatat tggcagtgca gtgtgtcgtt ggttagatag aaaaaccgat      540
acccaggaac tattcttaat tgctcgcaat aaagaacgat tacaacgact gcaagatgag      600
ttgggacggg gtaaaattat gggattggag gaggctttac ccgaagcaga tattatcgtt      660
tgggtggcga gtatgcccaa aggagtggaa attaatgccg aaactctcaa aaaccctgt       720
ttaattatcg atggtggtta tcctaagaat ttagacacaa aaattaaaca tcctgatgtc      780
catatcctga aaggggaat tgtagaacat tctctagata ttgactggaa gattatggaa       840
actgtcaata tggatgttcc ttctcgtcaa atgtttgctt gttttgccga agccatttta      900
ttagagtttg aacaatggca cactaatttt tcttgggac gcaatcaaat tacagtgact        960
aaaatggaac aaataggaga agcttctgtc aaacatgggt tacaaccgtt gttgagttgg      1020
taa                                                                    1023
```

<210> SEQ ID NO 32
<211> LENGTH: 340
<212> TYPE: PRT
<213> ORGANISM: Cyanothece sp.

<400> SEQUENCE: 32

```
Met Phe Gly Leu Ile Gly His Leu Thr Ser Leu Glu His Ala His Ser
1               5                   10                  15

Val Ala Asp Ala Phe Gly Tyr Gly Pro Tyr Ala Thr Gln Gly Leu Asp
                20                  25                  30

Leu Trp Cys Ser Ala Pro Pro Gln Phe Val Glu His Phe His Val Thr
            35                  40                  45

Ser Ile Thr Gly Gln Thr Ile Glu Gly Lys Tyr Ile Glu Ser Ala Phe
        50                  55                  60

Leu Pro Glu Met Leu Ile Lys Arg Arg Ile Lys Ala Ala Ile Arg Lys
65                  70                  75                  80

Ile Leu Asn Ala Met Ala Phe Ala Gln Lys Asn Asn Leu Asn Ile Thr
                85                  90                  95

Ala Leu Gly Gly Phe Ser Ser Ile Ile Phe Glu Glu Phe Asn Leu Lys
            100                 105                 110

Glu Asn Arg Gln Val Arg Asn Val Ser Leu Glu Phe Asp Arg Phe Thr
        115                 120                 125

Thr Gly Asn Thr His Thr Ala Tyr Ile Ile Cys Arg Gln Val Glu Gln
    130                 135                 140

Ala Ser Ala Lys Leu Gly Ile Asp Leu Ser Gln Ala Thr Val Ala Ile
145                 150                 155                 160

Cys Gly Ala Thr Gly Asp Ile Gly Ser Ala Val Cys Arg Trp Leu Asp
                165                 170                 175

Arg Lys Thr Asp Thr Gln Glu Leu Phe Leu Ile Ala Arg Asn Lys Glu
            180                 185                 190

Arg Leu Gln Arg Leu Gln Asp Glu Leu Gly Arg Gly Lys Ile Met Gly
        195                 200                 205

Leu Glu Glu Ala Leu Pro Glu Ala Asp Ile Ile Val Trp Val Ala Ser
    210                 215                 220

Met Pro Lys Gly Val Glu Ile Asn Ala Glu Thr Leu Lys Lys Pro Cys
225                 230                 235                 240
```

Leu Ile Ile Asp Gly Gly Tyr Pro Lys Asn Leu Asp Thr Lys Ile Lys
            245                       250                       255

His Pro Asp Val His Ile Leu Lys Gly Gly Ile Val Glu His Ser Leu
            260                       265                       270

Asp Ile Asp Trp Lys Ile Met Glu Thr Val Asn Met Asp Val Pro Ser
            275                       280                     285

Arg Gln Met Phe Ala Cys Phe Ala Glu Ala Ile Leu Leu Glu Phe Glu
            290                       295                     300

Gln Trp His Thr Asn Phe Ser Trp Gly Arg Asn Gln Ile Thr Val Thr
305                     310                     315                 320

Lys Met Glu Gln Ile Gly Glu Ala Ser Val Lys His Gly Leu Gln Pro
            325                       330                     335

Leu Leu Ser Trp
            340

<210> SEQ ID NO 33
<211> LENGTH: 1044
<212> TYPE: DNA
<213> ORGANISM: Prochlorococcus marinus

<400> SEQUENCE: 33

```
atggcatttg gcttataggg tcattcaact agttttgaag atgcaaaaag aaaggcttca      60
ttattgggct tgatcatat tgcggatggt gatttagatg tttggtgcac agctccacct     120
caactagttg aaaatgtaga ggttaaaagt gctataggta tatcaattga aggttcttat     180
attgattcat gtttcgttcc tgaaatgctt tcaagattta aaacggcaag aagaaaagta     240
ttaaatgcaa tggaattagc tcaaaaaaaa ggtattaata ttaccgcttt gggggggttc     300
acttctatca tctttgaaaa ttttaatctc cttcaacata gcagattag aaacacttca     360
ctagagtggg aaaggtttac aactggtaat actcatactg cgtgggttat ttgcaggcaa     420
ttagagatga atgctcctaa ataggtatt gatcttaaaa gcgcaacagt tgctgtagtt     480
ggtgctactg agatataggg cagtgctgtt tgtcgatggt taatcaataa acaggtatt     540
ggggaacttc ttttggtagc taggcaaaag gaacccttgg attctttgca aaaggaatta     600
gatggtggaa ctatcaaaaa tctagatgaa gcattgcctg aagcagatat tgttgtatgg     660
gtagcaagta tgccaaagac aatggaaatc gatgctaata atcttaaaca accatgttta     720
atgattgatg gaggttatcc aaagaatcta gatgaaaaat ttcaaggaaa taatatacat     780
gttgtaaaag gaggtatagt aagattcttc aatgatatag ttggaatat gatgaaacta     840
gctgaaatgc aaaatcccca gagagaaatg tttgcatgct ttgcagaagc aatgattta     900
gaatttgaaa atgtcatac aaactttagc tggggaagaa ataatatatc tctcgagaaa     960
atggagttta ttggagctgc ttctgtaaag catggcttct ctgcaattgg cctagataag    1020
catccaaaag tactagcagt ttga                                            1044
```

<210> SEQ ID NO 34
<211> LENGTH: 347
<212> TYPE: PRT
<213> ORGANISM: Prochlorococcus marinus

<400> SEQUENCE: 34

Met Ala Phe Gly Leu Ile Gly His Ser Thr Ser Phe Glu Asp Ala Lys
1                 5                    10                   15

Arg Lys Ala Ser Leu Leu Gly Phe Asp His Ile Ala Asp Gly Asp Leu
            20                       25                     30

```
Asp Val Trp Cys Thr Ala Pro Pro Gln Leu Val Glu Asn Val Glu Val
         35                  40                  45

Lys Ser Ala Ile Gly Ile Ser Ile Glu Gly Ser Tyr Ile Asp Ser Cys
 50                  55                  60

Phe Val Pro Glu Met Leu Ser Arg Phe Lys Thr Ala Arg Arg Lys Val
 65                  70                  75                  80

Leu Asn Ala Met Glu Leu Ala Gln Lys Lys Gly Ile Asn Ile Thr Ala
                 85                  90                  95

Leu Gly Gly Phe Thr Ser Ile Ile Phe Glu Asn Phe Asn Leu Leu Gln
                100                 105                 110

His Lys Gln Ile Arg Asn Thr Ser Leu Glu Trp Glu Arg Phe Thr Thr
            115                 120                 125

Gly Asn Thr His Thr Ala Trp Val Ile Cys Arg Gln Leu Glu Met Asn
130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
            195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
            275                 280                 285

Glu Met Phe Ala Cys Phe Ala Glu Ala Met Ile Leu Glu Phe Glu Lys
            290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Val
            340                 345

<210> SEQ ID NO 35
<211> LENGTH: 1053
<212> TYPE: DNA
<213> ORGANISM: Gloeobacter violaceus

<400> SEQUENCE: 35
atgtttggcc tgatcggaca cttgaccaat cttttcccatg cccagcgggt cgcccgcgac     60
ctgggctacg acgagtatgc aagccacgac ctcgaattct ggtgcatggc ccctccccag    120
gcggtcgatg aaatcacgat caccagcgtc accggtcagg tgatccacgg tcagtacgtc    180
gaatcgtgct ttctgccgga gatgctcgcc cagggccgct tcaagaccgc catgcgcaag    240
atcctcaatg ccatggccct ggtccagaag cgcggcatcg acattacggc cctgggaggc    300
```

```
ttctcgtcga tcatcttcga gaatttcagc ctcgataaat tgctcaacgt ccgcgacatc    360
accctcgaca tccagcgctt caccaccggc aacacccaca cggcctacat cctttgtcag    420
caggtcgagc agggtgcggt acgctacggc atcgatccgg ccaaagcgac cgtggcggta    480
gtcggggcca ccggcgacat cggtagcgcc gtctgccgat ggctcaccga ccgcgccggc    540
atccacgaac tcttgctggt ggcccgcgac gccgaaaggc tcgaccggct gcagcaggaa    600
ctcggcaccg tcggatcctg gccggtcgaa gaagcacttc ccaaagccga catcgtcgtc    660
tgggtcgcct cgatgaacca gggcatggcc atcgaccccg ccggcctgcg caccccctgc    720
ctgctcatcg acggcggcta ccccaagaac atggccggca ccctgcagcg cccgggcatc    780
catatcctcg acggcggcat ggtcgagcac tcgctcgaca tcgactggca gatcatgtcg    840
tttctaaatg tgcccaaccc cgcccgccag ttcttcgcct gcttcgccga gtcgatgctg    900
ctggaattcg aagggcttca cttcaatttt tcctggggcc gcaaccacat caccgtcgag    960
aagatggccc agatcggctc gctgtctaaa aacatggct  ttcgtcccct gcttgaaccc   1020
agtcagcgca gcggcgaact cgtacacgga taa                                1053
```

<210> SEQ ID NO 36
<211> LENGTH: 350
<212> TYPE: PRT
<213> ORGANISM: Gloeobacter violaceus

<400> SEQUENCE: 36

```
Met Phe Gly Leu Ile Gly His Leu Thr Asn Leu Ser His Ala Gln Arg
1               5                   10                  15

Val Ala Arg Asp Leu Gly Tyr Asp Glu Tyr Ala Ser His Asp Leu Glu
            20                  25                  30

Phe Trp Cys Met Ala Pro Pro Gln Ala Val Asp Glu Ile Thr Ile Thr
        35                  40                  45

Ser Val Thr Gly Gln Val Ile His Gly Gln Tyr Val Glu Ser Cys Phe
    50                  55                  60

Leu Pro Glu Met Leu Ala Gln Gly Arg Phe Lys Thr Ala Met Arg Lys
65                  70                  75                  80

Ile Leu Asn Ala Met Ala Leu Val Gln Lys Arg Gly Ile Asp Ile Thr
                85                  90                  95

Ala Leu Gly Gly Phe Ser Ser Ile Ile Phe Glu Asn Phe Ser Leu Asp
            100                 105                 110

Lys Leu Leu Asn Val Arg Asp Ile Thr Leu Asp Ile Gln Arg Phe Thr
        115                 120                 125

Thr Gly Asn Thr His Thr Ala Tyr Ile Leu Cys Gln Gln Val Glu Gln
    130                 135                 140

Gly Ala Val Arg Tyr Gly Ile Asp Pro Ala Lys Ala Thr Val Ala Val
145                 150                 155                 160

Val Gly Ala Thr Gly Asp Ile Gly Ser Ala Val Cys Arg Trp Leu Thr
                165                 170                 175

Asp Arg Ala Gly Ile His Glu Leu Leu Val Ala Arg Asp Ala Glu
            180                 185                 190

Arg Leu Asp Arg Leu Gln Gln Glu Leu Gly Thr Gly Arg Ile Leu Pro
        195                 200                 205

Val Glu Glu Ala Leu Pro Lys Ala Asp Ile Val Val Trp Val Ala Ser
    210                 215                 220

Met Asn Gln Gly Met Ala Ile Asp Pro Ala Gly Leu Arg Thr Pro Cys
225                 230                 235                 240
```

Leu Leu Ile Asp Gly Gly Tyr Pro Lys Asn Met Ala Gly Thr Leu Gln
            245                 250                 255

Arg Pro Gly Ile His Ile Leu Asp Gly Gly Met Val Glu His Ser Leu
        260                 265                 270

Asp Ile Asp Trp Gln Ile Met Ser Phe Leu Asn Val Pro Asn Pro Ala
    275                 280                 285

Arg Gln Phe Phe Ala Cys Phe Ala Glu Ser Met Leu Leu Glu Phe Glu
290                 295                 300

Gly Leu His Phe Asn Phe Ser Trp Gly Arg Asn His Ile Thr Val Glu
305                 310                 315                 320

Lys Met Ala Gln Ile Gly Ser Leu Ser Lys Lys His Gly Phe Arg Pro
                325                 330                 335

Leu Leu Glu Pro Ser Gln Arg Ser Gly Glu Leu Val His Gly
            340                 345                 350

<210> SEQ ID NO 37
<211> LENGTH: 1020
<212> TYPE: DNA
<213> ORGANISM: Nostoc punctiforme

<400> SEQUENCE: 37
atgtttggtc taattggaca tctgactagt ttagaacacg ctcaagccgt agcccaagaa      60
ttgggatacc cagaatatgc cgatcaaggg ctagactttt ggtgcagcgc cccgccgcaa     120
attgtcgata gtattattgt caccagtgtt actgggcaac aaattgaagg acgatatgta     180
gaatcttgct ttttgccgga atgctagcag tcgccgca tcaaagccgc aacacggaaa      240
atcctcaacg ctatggccca tgcacagaag cacggcatta acatcacagc tttaggcgga     300
ttttcctcga ttattttga aaactttaag ttagagcagt ttagccaagt ccgaaatatc     360
aagctagagt ttgaacgctt caccacagga aacacgcata ctgcctacat tatttgtaag     420
caggtggaag aagcatccaa acaactggga attaatctat caaacgcgac tgttgcggta     480
tgtggagcaa ctggggatat tggtagtgcc gttacacgct ggctagatgc gagaacagat     540
gtccaagaac tcctgctaat cgcccgcgat caagaacgtc tcaaagagtt gcaaggcgaa     600
ctggggcggg ggaaaatcat gggtttgaca gaagcactac cccaagccga tgttgtagtt     660
tgggttgcta gtatgcccag aggcgtggaa attgacccca ccactttgaa caaccctgt      720
ttgttgattg atggtggcta tcctaaaaac ttagcaacaa aaattcaata tcctggcgta     780
cacgtgttaa atggtgggat tgtagagcat ccctggata ttgactggaa aattatgaaa      840
atagtcaata tggacgtgcc agcccgtcag ttgtttgcct gttttgccga atcaatgcta     900
ctggaatttg agaagttata cacgaacttt tcgtgggac ggaatcagat taccgtagat      960
aaaatggagc agattggccg ggtgtcagta aacatggat ttagaccgtt gttggtttag     1020

<210> SEQ ID NO 38
<211> LENGTH: 339
<212> TYPE: PRT
<213> ORGANISM: Nostoc punctiforme

<400> SEQUENCE: 38

Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp Ser Ile Ile Val Thr
        35                  40                  45

```
Ser Val Thr Gly Gln Gln Ile Glu Gly Arg Tyr Val Glu Ser Cys Phe
 50                  55                  60
Leu Pro Glu Met Leu Ala Ser Arg Arg Ile Lys Ala Ala Thr Arg Lys
 65                  70                  75                  80
Ile Leu Asn Ala Met Ala His Ala Gln Lys His Gly Ile Asn Ile Thr
                 85                  90                  95
Ala Leu Gly Gly Phe Ser Ser Ile Ile Phe Glu Asn Phe Lys Leu Glu
                100                 105                 110
Gln Phe Ser Gln Val Arg Asn Ile Lys Leu Glu Phe Glu Arg Phe Thr
                115                 120                 125
Thr Gly Asn Thr His Thr Ala Tyr Ile Ile Cys Lys Val Glu Glu
130                 135                 140
Ala Ser Lys Gln Leu Gly Ile Asn Leu Ser Asn Ala Thr Val Ala Val
145                 150                 155                 160
Cys Gly Ala Thr Gly Asp Ile Gly Ser Ala Val Thr Arg Trp Leu Asp
                165                 170                 175
Ala Arg Thr Asp Val Gln Glu Leu Leu Leu Ile Ala Arg Asp Gln Glu
                180                 185                 190
Arg Leu Lys Glu Leu Gln Gly Glu Leu Gly Arg Gly Lys Ile Met Gly
                195                 200                 205
Leu Thr Glu Ala Leu Pro Gln Ala Asp Val Val Trp Val Ala Ser
210                 215                 220
Met Pro Arg Gly Val Glu Ile Asp Pro Thr Thr Leu Lys Gln Pro Cys
225                 230                 235                 240
Leu Leu Ile Asp Gly Gly Tyr Pro Lys Asn Leu Ala Thr Lys Ile Gln
                245                 250                 255
Tyr Pro Gly Val His Val Leu Asn Gly Gly Ile Val Glu His Ser Leu
                260                 265                 270
Asp Ile Asp Trp Lys Ile Met Lys Ile Val Asn Met Asp Val Pro Ala
                275                 280                 285
Arg Gln Leu Phe Ala Cys Phe Ala Glu Ser Met Leu Leu Glu Phe Glu
                290                 295                 300
Lys Leu Tyr Thr Asn Phe Ser Trp Gly Arg Asn Gln Ile Thr Val Asp
305                 310                 315                 320
Lys Met Glu Gln Ile Gly Arg Val Ser Val Lys His Gly Phe Arg Pro
                325                 330                 335
Leu Leu Val
```

<210> SEQ ID NO 39
<211> LENGTH: 1020
<212> TYPE: DNA
<213> ORGANISM: Anabaena variabilis

<400> SEQUENCE: 39

```
atgtttggtc taattggaca tctgacaagt ttagaacacg ctcaagcggt agctcaagaa      60
ctgggatacc cagaatacgc cgaccaaggg ctagattttt ggtgcagcgc tccaccgcaa     120
atagttgacc acattaaagt tactagcatt actggtgaaa taattgaagg gaggtatgta     180
gaatcttgct ttttaccaga aatgctagcc agccgtagga ttaaagccgc aacccgcaaa     240
gtcctcaatg ctatggctca tgctcaaaaa catggcattg acatcaccgc tttgggtggt     300
ttctcctcca ttattttga aaacttcaaa ttggaacagt ttagccaagt tcgtaatgtc     360
acactagagt ttgaacgctt cactacaggc aacactcaca cagcttatat catttgtcgg     420
```

```
caggtagaac aagcatcaca acaactcggc attgaactct cccaagcaac agtagctata    480 tgtgggcta ctggtgacat tggtagtgca gttactcgct ggctggatgc caaaacagac    540
gtaaaagaat tactgttaat cgcccgtaat caagaacgtc tccaagagtt gcaaagcgag    600
ttgggacgcg gtaaaatcat gagcctagat gaagcattgc ctcaagctga tattgtagtt    660
tgggtagcta gtatgcctaa aggcgtggaa attaatcctc aagttttgaa acaaccctgt    720
ttattgattg atggtggtta tccgaaaaac ttgggtacaa agttcagta tcctggtgtt    780 tatgtactga acggaggtat cgtcgaacat tccctagata ttgactggaa aatcatgaaa    840
atagtcaata tggatgtacc tgcacgccaa ttatttgctt gttttgcgga atctatgctc    900
ttggaatttg agaagttgta cacgaacttt tcttgggggc gcaatcagat taccgtagac    960
aaaatggagc agattggtca agcatcagtg aaacatgggt ttagaccact gctggtttag    1020
```

<210> SEQ ID NO 40
<211> LENGTH: 339
<212> TYPE: PRT
<213> ORGANISM: Anabaena variabilis

<400> SEQUENCE: 40

```
Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Lys Val Thr
        35                  40                  45

Ser Ile Thr Gly Glu Ile Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Leu Ile Ala Arg Asn Gln Glu
            180                 185                 190

Arg Leu Gln Glu Leu Gln Ser Glu Leu Gly Arg Gly Lys Ile Met Ser
        195                 200                 205

Leu Asp Glu Ala Leu Pro Gln Ala Asp Ile Val Val Trp Val Ala Ser
    210                 215                 220

Met Pro Lys Gly Val Glu Ile Asn Pro Gln Val Leu Lys Gln Pro Cys
225                 230                 235                 240

Leu Leu Ile Asp Gly Gly Tyr Pro Lys Asn Leu Gly Thr Lys Val Gln
                245                 250                 255

Tyr Pro Gly Val Tyr Val Leu Asn Gly Gly Ile Val Glu His Ser Leu
            260                 265                 270
```

Asp Ile Asp Trp Lys Ile Met Lys Ile Val Asn Met Asp Val Pro Ala
            275                 280                 285

Arg Gln Leu Phe Ala Cys Phe Ala Glu Ser Met Leu Leu Glu Phe Glu
        290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val

<210> SEQ ID NO 41
<211> LENGTH: 1026
<212> TYPE: DNA
<213> ORGANISM: Synechococcus elongatus

<400> SEQUENCE: 41

| | | | | | | |
|---|---|---|---|---|---|---|
| atgttcggtc | ttatcggtca | tctcaccagt | ttggagcagg | cccgcgacgt | ttctcgcagg | 60 |
| atgggctacg | acgaatacgc | cgatcaagga | ttggagtttt | ggagtagcgc | tcctcctcaa | 120 |
| atcgttgatg | aaatcacagt | caccagtgcc | acaggcaagg | tgattcacgg | tcgctacatc | 180 |
| gaatcgtgtt | tcttgccgga | aatgctggcg | gcgcgccgct | tcaaaacagc | cacgcgcaaa | 240 |
| gttctcaatg | ccatgtccca | tgcccaaaaa | cacggcatcg | acatctcggc | cttgggggc | 300 |
| tttacctcga | ttattttcga | gaatttcgat | ttggccagtt | tgcggcaagt | gcgcgacact | 360 |
| accttggagt | ttgaacggtt | caccaccggc | aatactcaca | cggcctacgt | aatctgtaga | 420 |
| caggtggaag | ccgctgctaa | aacgctgggc | atcgacatta | cccaagcgac | agtagcggtt | 480 |
| gtcggcgcga | ctggcgatat | cggtagcgct | gtctgccgct | ggctcgacct | caaactgggt | 540 |
| gtcggtgatt | tgatcctgac | ggcgcgcaat | caggagcgtt | tggataacct | gcaggctgaa | 600 |
| ctcggccggg | gcaagattct | gcccttggaa | gccgctctgc | cggaagctga | ctttatcgtg | 660 |
| tgggtcgcca | gtatgcctca | gggcgtagtg | atcgacccag | caaccctgaa | gcaaccctgc | 720 |
| gtcctaatcg | acgggggcta | ccccaaaaac | ttgggcagca | agtccaagg | tgagggcatc | 780 |
| tatgtcctca | atggcgggt | agttgaacat | tgcttcgaca | tcgactggca | gatcatgtcc | 840 |
| gctgcagaga | tggcgcggcc | cgagcgccag | atgtttgcct | gctttgccga | ggcgatgctc | 900 |
| ttggaatttg | aaggctggca | tactaacttc | tcctggggcc | gcaaccaaat | cacgatcgag | 960 |
| aagatggaag | cgatcggtga | ggcatcggtg | cgccacggct | tccaaccctt | ggcattggca | 1020 |
| atttga | | | | | | 1026 |

<210> SEQ ID NO 42
<211> LENGTH: 340
<212> TYPE: PRT
<213> ORGANISM: Synechococcus elongatus

<400> SEQUENCE: 42

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys

```
                 65                  70                  75                  80
        Val Leu Asn Ala Met Ser His Ala Gln Lys His Gly Ile Asp Ile Ser
                         85                  90                  95
        Ala Leu Gly Gly Phe Thr Ser Ile Ile Phe Glu Asn Phe Asp Leu Ala
                        100                 105                 110
        Ser Leu Arg Gln Val Arg Asp Thr Thr Leu Glu Phe Glu Arg Phe Thr
                        115                 120                 125
        Thr Gly Asn Thr His Thr Ala Tyr Val Ile Cys Arg Gln Val Glu Ala
                130                 135                 140
        Ala Ala Lys Thr Leu Gly Ile Asp Ile Thr Gln Ala Thr Val Ala Val
        145                 150                 155                 160
        Val Gly Ala Thr Gly Asp Ile Gly Ser Ala Val Cys Arg Trp Leu Asp
                        165                 170                 175
        Leu Lys Leu Gly Val Gly Asp Leu Ile Leu Thr Ala Arg Asn Gln Glu
                        180                 185                 190
        Arg Leu Asp Asn Leu Gln Ala Glu Leu Gly Arg Gly Lys Ile Leu Pro
                        195                 200                 205
        Leu Glu Ala Ala Leu Pro Glu Ala Asp Phe Ile Val Trp Val Ala Ser
                        210                 215                 220
        Met Pro Gln Gly Val Val Ile Asp Pro Ala Thr Leu Lys Gln Pro Cys
        225                 230                 235                 240
        Val Leu Ile Asp Gly Gly Tyr Pro Lys Asn Leu Gly Ser Lys Val Gln
                        245                 250                 255
        Gly Glu Gly Ile Tyr Val Leu Asn Gly Gly Val Val Glu His Cys Phe
                        260                 265                 270
        Asp Ile Asp Trp Gln Ile Met Ser Ala Ala Glu Met Ala Arg Pro Glu
                        275                 280                 285
        Arg Gln Met Phe Ala Cys Phe Ala Glu Ala Met Leu Leu Glu Phe Glu
                        290                 295                 300
        Gly Trp His Thr Asn Phe Ser Trp Gly Arg Asn Gln Ile Thr Ile Glu
        305                 310                 315                 320
        Lys Met Glu Ala Ile Gly Glu Ala Ser Val Arg His Gly Phe Gln Pro
                        325                 330                 335
        Leu Ala Leu Ala
                        340

<210> SEQ ID NO 43
<211> LENGTH: 1020
<212> TYPE: DNA
<213> ORGANISM: Nostoc sp.

<400> SEQUENCE: 43
atgtttggtc taattggaca tctgacaagt ttagaacacg ctcaagcggt agctcaagaa      60
ctgggatacc agaatacgc cgaccaaggg ctagattttt ggtgtagcgc tccaccgcaa     120
atagttgacc acattaaagt tactagtatt actggtgaaa taattgaagg gaggtatgta     180
gaatcttgct ttttaccgga gatgctagcc agtcgtcgga ttaaagccgc aacccgcaaa     240
gtcctcaatg ctatggctca tgctcaaaag aatggcattg atatcacagc tttgggtggt     300
ttctcctcca ttattttga aaactttaaa ttggagcagt ttagccaagt tcgtaatgtg     360
acactagagt ttgaacgctt cactacaggc aacactcaca cagcatatat tatttgtcgg     420
caggtagaac aagcatcaca caactcggc attgaactct cccaagcaac agtagctata     480
tgtggggcta ctggtgatat tggtagtgca gttactcgct ggctggatgc taaaacagac     540
```

```
gtgaaagaat tgctgttaat cgcccgtaat caagaacgtc tccaagagtt gcaaagcgag    600
ctgggacgcg gtaaaatcat gagccttgat gaagcactgc cccaagctga tatcgtagtt    660
tgggtagcca gtatgcctaa aggtgtggaa attaatcctc aagttttgaa gcaaccctgt    720
ttgctgattg atgggggtta tccgaaaaac ttgggtacaa agttcagta tcctggtgtt     780 tatgtactga acggcggtat cgtcgaacat cgctggata ttgactggaa aatcatgaaa     840
atagtcaata tggatgtacc tgcacgccaa ttatttgctt gttttgcgga atctatgctc    900
ttggaatttg agaagttgta cacgaacttt tcttggggc gcaatcagat taccgtagac     960
aaaatggagc agattggtca agcatcagtg aaacatgggt ttagaccact gctggtttag    1020
```

<210> SEQ ID NO 44
<211> LENGTH: 339
<212> TYPE: PRT
<213> ORGANISM: Nostoc sp.

<400> SEQUENCE: 44

```
Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Lys Val Thr
        35                  40                  45

Ser Ile Thr Gly Glu Ile Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys Asn Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Leu Ile Ala Arg Asn Gln Glu
            180                 185                 190

Arg Leu Gln Glu Leu Gln Ser Glu Leu Gly Arg Gly Lys Ile Met Ser
        195                 200                 205

Leu Asp Glu Ala Leu Pro Gln Ala Asp Ile Val Val Trp Val Ala Ser
    210                 215                 220

Met Pro Lys Gly Val Glu Ile Asn Pro Gln Val Leu Lys Gln Pro Cys
225                 230                 235                 240

Leu Leu Ile Asp Gly Gly Tyr Pro Lys Asn Leu Gly Thr Lys Val Gln
                245                 250                 255

Tyr Pro Gly Val Tyr Val Leu Asn Gly Gly Ile Val Glu His Ser Leu
            260                 265                 270

Asp Ile Asp Trp Lys Ile Met Lys Ile Val Asn Met Asp Val Pro Ala
        275                 280                 285

Arg Gln Leu Phe Ala Cys Phe Ala Glu Ser Met Leu Leu Glu Phe Glu
```

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val

<210> SEQ ID NO 45
<211> LENGTH: 867
<212> TYPE: DNA
<213> ORGANISM: Corynebacterium glutamicum

<400> SEQUENCE: 45

```
ttgggcgtgt cgcccttaaa gcgcgctttt cgacgcgacc ccactacatt ggcttccatg    60
aacgttgaca tttcacgatc cagagagccg ctaaacgttg agctcctgaa ggaaaaattg   120
ctccaaaacg gtgactttgg ccaggtcatt tacgaaaaag tgacaggctc cactaatgct   180
gacttgctgg cacttgcagg ttctggcgct ccaaactgga cggtgaaaac tgtcgagttt   240
caagatcatg cgcgtgggcg actcggccgc ccgtggtctg cccctgaggg ttcccaaaca   300
atcgtgtctg tgctcgttca actatctatt gatcaagtgg accggattgg cactattcca   360
ctcgcggcgg gactcgctgt catggatgcg ttgaatgacc tcggtgtgga aggtgccgga   420
ctgaaatggc caacgatgt tcaaatccac ggcaagaaac tctgcggcat cctggtggaa   480
gccaccggct tgattccac cccaacagtt gtcatcggtt ggggcactaa tatcagcctg   540
actaaagagg agcttcctgt tcctcatgca acttccctcg cattggaagg tgttgaagtc   600
gacagaacca cattccttat taatatgctc acacatctgc atactcgact ggaccagtgg   660
cagggtccaa gtgtggattg gctcgatgat taccgtgcgg tatgttccag tattggccaa   720
gatgttcgag tgcttctacc tggggataaa gaactcttag gtgaagcgat cggtgtcgcg   780
actggcggag aaattcgtgt tcgcgatgct tcgggcaccg ttcacaccct caacgccggt   840
gaaattacgc accttcgcct gcagtaa                                       867
```

<210> SEQ ID NO 46
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
atgaatgttg acattagccg ctctcgtgaa ccgttgaacg tggaactgtt gaagaaaaaa    60
ctgctgcaga cggtgatttc ggtcaagtga tctacgaga aggtcaccgg ctctaccaat   120
gcggacctgc tggctctggc gggcagcggc gctccaaact ggaccgtcaa gactgttgaa   180
tttcaggacc acgcccgtgg ccgtctgggt cgtccgtgga gcgcaccgga gggttcccaa   240
accatcgtca gcgttctggt ccaactgagc attgatcagg tggaccgtat tggtacgatc   300
ccgctggccg caggcttggc tgttatggat gcgctgaatg atctgggcgt ggagggtgca   360
ggcctgaaat ggccgaacga tgttcagatc cacggtaaga agttgtgcgg tattctggtt   420
gaagcaaccg gcttcgactc cactccgacc gtggttatcg gttggggtac gaatatctcg   480
ttgacgaaag aagagctgcc ggtcccgcac gcgaccagcc tggccctgga gggtgttgaa   540
gttgaccgta cgacgttcct gattaacatg ctgacccatc tgcataccg tctggatcag   600
```

```
tggcagggtc cgtctgtgga ctggctggat gactatcgcg cggtttgtag cagcattggc    660
caagatgtgc gtgtcctgct gcctggtgac aaagagctgc tgggcgaggc gattggcgtg    720
gcgaccggtg gtgagatccg tgtgcgcgac gccagcggca cggtccacac gctgaatgcg    780
ggtgaaatca cgcatctgcg tttgcaataa                                     810
```

<210> SEQ ID NO 47
<211> LENGTH: 269
<212> TYPE: PRT
<213> ORGANISM: Corynebacterium glutamicum

<400> SEQUENCE: 47

```
Met Asn Val Asp Ile Ser Arg Ser Arg Glu Pro Leu Asn Val Glu Leu
1               5                   10                  15

Leu Lys Glu Lys Leu Leu Gln Asn Gly Asp Phe Gly Gln Val Ile Tyr
            20                  25                  30

Glu Lys Val Thr Gly Ser Thr Asn Ala Asp Leu Leu Ala Leu Ala Gly
        35                  40                  45

Ser Gly Ala Pro Asn Trp Thr Val Lys Thr Val Glu Phe Gln Asp His
    50                  55                  60

Ala Arg Gly Arg Leu Gly Arg Pro Trp Ser Ala Pro Glu Gly Ser Gln
65                  70                  75                  80

Thr Ile Val Ser Val Leu Val Gln Leu Ser Ile Asp Gln Val Asp Arg
                85                  90                  95

Ile Gly Thr Ile Pro Leu Ala Ala Gly Leu Ala Val Met Asp Ala Leu
            100                 105                 110

Asn Asp Leu Gly Val Glu Gly Ala Gly Leu Lys Trp Pro Asn Asp Val
        115                 120                 125

Gln Ile His Gly Lys Lys Leu Cys Gly Ile Leu Val Glu Ala Thr Gly
    130                 135                 140

Phe Asp Ser Thr Pro Thr Val Val Ile Gly Trp Gly Thr Asn Ile Ser
145                 150                 155                 160

Leu Thr Lys Glu Glu Leu Pro Val Pro His Ala Thr Ser Leu Ala Leu
                165                 170                 175

Glu Gly Val Glu Val Asp Arg Thr Thr Phe Leu Ile Asn Met Leu Thr
            180                 185                 190

His Leu His Thr Arg Leu Asp Gln Trp Gln Gly Pro Ser Val Asp Trp
        195                 200                 205

Leu Asp Asp Tyr Arg Ala Val Cys Ser Ser Ile Gly Gln Asp Val Arg
    210                 215                 220

Val Leu Leu Pro Gly Asp Lys Glu Leu Leu Gly Glu Ala Ile Gly Val
225                 230                 235                 240

Ala Thr Gly Gly Glu Ile Arg Val Arg Asp Ala Ser Gly Thr Val His
                245                 250                 255

Thr Leu Asn Ala Gly Glu Ile Thr His Leu Arg Leu Gln
            260                 265
```

<210> SEQ ID NO 48
<211> LENGTH: 1632
<212> TYPE: DNA
<213> ORGANISM: Corynebacterium glutamicum

<400> SEQUENCE: 48

```
atgaccattt cctcacccttt gattgacgtc gccaaccttc cagacatcaa caccactgcc     60
ggcaagatcg ccgaccttaa ggctcgccgc gcggaagccc atttccccat gggtgaaaag    120
```

```
gcagtagaga aggtccacgc tgctggacgc ctcactgccc gtgagcgctt ggattactta    180
ctcgatgagg gctccttcat cgagaccgat cagctggctc gccaccgcac caccgctttc    240
ggcctgggcg ctaagcgtcc tgcaaccgac ggcatcgtga ccggctgggg caccattgat    300
ggacgcgaag tctgcatctt ctcgcaggac ggcaccgtat tcggtggcgc gcttggtgag    360
gtgtacggcg aaaagatgat caagatcatg gagctggcaa tcgacaccgg ccgcccattg    420
atcggtcttt acgaaggcgc tggcgctcgt attcaggacg cgctgtctc cctggacttc    480 atttcccaga ccttctacca aaacattcag gcttctggcg ttatcccaca gatctccgtc    540
atcatgggcg catgtgcagg tggcaacgct tacggcccag ctctgaccga cttcgtggtc    600
atggtggaca agacctccaa gatgttcgtt accggcccag acgtgatcaa gaccgtcacc    660
ggcgaggaaa tcacccagga gagcttggc ggagcaacca cccacatggt gaccgctggt    720
aactcccact acaccgctgc gaccgatgag gaagcactgg attgggtaca ggacctggtg    780
tccttcctcc catccaacaa tgctcctac gcaccgatgg aagacttcga cgaggaagaa    840
ggcggcgttg aagaaaacat caccgctgac gatctgaagc tcgacgagat catcccagat    900
tccgcgaccg ttccttacga cgtccgcgat gtcatcgaat gcctcaccga cgatggcgaa    960
tacctggaaa tccaggcaga ccgcgcagaa acgttgtta ttgcattcgg ccgcatcgaa   1020
ggccagtccg ttggctttgt tgccaaccag ccaacccagt cgctggctg cctggacatc   1080 gactcctctg agaaggcagc tcgcttcgtc cgcacctgcg acgcgttcaa catcccaatc   1140
gtcatgcttg tcgacgtccc cggcttcctc ccaggcgcag gccaggagta cggtggcatt   1200
ctgcgtcgtg gcgcaaagct gctctacgca tacggcgaag caaccgttcc aaagatcacc   1260
gtcaccatgc gtaaggctta cggcggagcg tactgcgtga tgggttccaa gggcttgggc   1320
tctgacatca accttgcatg gccaaccgca cagatcgccg tcatgggcgc tgctggcgca   1380
gttggattca tctaccgcaa ggagctcatg gcagctgatg ccaagggcct cgataccgta   1440
gctctggcta gtccttcga gcgcgagtat gaagaccaca tgctcaaccc gtaccacgct   1500
gcagaacgtg gcctgatcga cgccgtgatc ctgccaagcg aaaacccgcg gacagatttcc   1560 cgcaaccttc gcctgctcaa gcacaagaac gtcactcgcc ctgctcgcaa gcacggcaac   1620
atgccactgt aa                                                       1632
```

<210> SEQ ID NO 49
<211> LENGTH: 543
<212> TYPE: PRT
<213> ORGANISM: Corynebacterium glutamicum

<400> SEQUENCE: 49

```
Met Thr Ile Ser Ser Pro Leu Ile Asp Val Ala Asn Leu Pro Asp Ile
1               5                   10                  15

Asn Thr Thr Ala Gly Lys Ile Ala Asp Leu Lys Ala Arg Arg Ala Glu
                20                  25                  30

Ala His Phe Pro Met Gly Glu Lys Ala Val Glu Lys Val His Ala Ala
            35                  40                  45

Gly Arg Leu Thr Ala Arg Glu Arg Leu Asp Tyr Leu Leu Asp Glu Gly
        50                  55                  60

Ser Phe Ile Glu Thr Asp Gln Leu Ala Arg His Arg Thr Thr Ala Phe
65                  70                  75                  80

Gly Leu Gly Ala Lys Arg Pro Ala Thr Asp Gly Ile Val Thr Gly Trp
                85                  90                  95

Gly Thr Ile Asp Gly Arg Glu Val Cys Ile Phe Ser Gln Asp Gly Thr
```

```
              100                 105                 110
Val Phe Gly Gly Ala Leu Gly Glu Val Tyr Gly Glu Lys Met Ile Lys
            115                 120                 125
Ile Met Glu Leu Ala Ile Asp Thr Gly Arg Pro Leu Ile Gly Leu Tyr
            130                 135                 140
Glu Gly Ala Gly Ala Arg Ile Gln Asp Gly Ala Val Ser Leu Asp Phe
145                 150                 155                 160
Ile Ser Gln Thr Phe Tyr Gln Asn Ile Gln Ala Ser Gly Val Ile Pro
            165                 170                 175
Gln Ile Ser Val Ile Met Gly Ala Cys Ala Gly Gly Asn Ala Tyr Gly
            180                 185                 190
Pro Ala Leu Thr Asp Phe Val Val Met Val Asp Lys Thr Ser Lys Met
            195                 200                 205
Phe Val Thr Gly Pro Asp Val Ile Lys Thr Val Thr Gly Glu Glu Ile
            210                 215                 220
Thr Gln Glu Glu Leu Gly Gly Ala Thr Thr His Met Val Thr Ala Gly
225                 230                 235                 240
Asn Ser His Tyr Thr Ala Ala Thr Asp Glu Glu Ala Leu Asp Trp Val
            245                 250                 255
Gln Asp Leu Val Ser Phe Leu Pro Ser Asn Asn Arg Ser Tyr Ala Pro
            260                 265                 270
Met Glu Asp Phe Asp Glu Glu Gly Gly Val Glu Glu Asn Ile Thr
            275                 280                 285
Ala Asp Asp Leu Lys Leu Asp Glu Ile Ile Pro Asp Ser Ala Thr Val
            290                 295                 300
Pro Tyr Asp Val Arg Asp Val Ile Glu Cys Leu Thr Asp Asp Gly Glu
305                 310                 315                 320
Tyr Leu Glu Ile Gln Ala Asp Arg Ala Glu Asn Val Val Ile Ala Phe
            325                 330                 335
Gly Arg Ile Glu Gly Gln Ser Val Gly Phe Val Ala Asn Gln Pro Thr
            340                 345                 350
Gln Phe Ala Gly Cys Leu Asp Ile Asp Ser Ser Glu Lys Ala Ala Arg
            355                 360                 365
Phe Val Arg Thr Cys Asp Ala Phe Asn Ile Pro Ile Val Met Leu Val
            370                 375                 380
Asp Val Pro Gly Phe Leu Pro Gly Ala Gly Gln Glu Tyr Gly Gly Ile
385                 390                 395                 400
Leu Arg Arg Gly Ala Lys Leu Leu Tyr Ala Tyr Gly Glu Ala Thr Val
            405                 410                 415
Pro Lys Ile Thr Val Thr Met Arg Lys Ala Tyr Gly Gly Ala Tyr Cys
            420                 425                 430
Val Met Gly Ser Lys Gly Leu Gly Ser Asp Ile Asn Leu Ala Trp Pro
            435                 440                 445
Thr Ala Gln Ile Ala Val Met Gly Ala Ala Gly Ala Val Gly Phe Ile
            450                 455                 460
Tyr Arg Lys Glu Leu Met Ala Ala Asp Ala Lys Gly Leu Asp Thr Val
465                 470                 475                 480
Ala Leu Ala Lys Ser Phe Glu Arg Glu Tyr Glu Asp His Met Leu Asn
            485                 490                 495
Pro Tyr His Ala Ala Glu Arg Gly Leu Ile Asp Ala Val Ile Leu Pro
            500                 505                 510
Ser Glu Thr Arg Gly Gln Ile Ser Arg Asn Leu Arg Leu Leu Lys His
            515                 520                 525
```

Lys Asn Val Thr Arg Pro Ala Arg Lys His Gly Asn Met Pro Leu
530                 535                 540

<210> SEQ ID NO 50
<211> LENGTH: 1776
<212> TYPE: DNA
<213> ORGANISM: Corynebacterium glutamicum

<400> SEQUENCE: 50

| | |
|---|---|
| atgtcagtcg agactcgcaa gatcaccaag gttcttgtcg ctaaccgtgg tgagattgca | 60 |
| atccgcgtgt tccgtgcagc tcgagatgaa ggcatcggat ctgtcgccgt ctacgcagag | 120 |
| ccagatgcag atgcaccatt cgtgtcatat gcagacgagg cttttgccct cggtggccaa | 180 |
| acatccgctg agtcctacct tgtcattgac aagatcatcg atgcggcccg caagtccggc | 240 |
| gccgacgcca tccaccccgg ctacggcttc ctcgcagaaa acgctgactt cgcagaagca | 300 |
| gtcatcaacg aaggcctgat ctggattgga ccttcacctg agtccatccg ctccctcggc | 360 |
| gacaaggtca ccgctcgcca catcgcagat accgccaagg ctccaatggc tcctggcacc | 420 |
| aaggaaccag taaagacgc agcagaagtt gtggctttcg ctgaagaatt cggtctccca | 480 |
| atcgccatca aggcagcttt cggtggcggc ggacgtggca tgaaggttgc ctacaagatg | 540 |
| gaagaagtcg ctgacctctt cgagtccgca acccgtgaag caaccgcagc gttcggccgc | 600 |
| ggcgagtgct tcgtggagcg ctacctggac aaggcacgcc acgttgaggc tcaggtcatc | 660 |
| gccgataagc acggcaacgt tgttgtcgcc ggaacccgtg actgctccct gcagcgccgt | 720 |
| ttccagaagc tcgtcgaaga agcaccagca ccattcctca ccgatgacca gcgcgagcgt | 780 |
| ctccactcct ccgcgaaggc tatctgtaag gaagctggct actacggtgc aggcaccgtt | 840 |
| gagtacctcg ttggctccga cggcctgatc tccttcctcg aggtcaacac ccgcctccag | 900 |
| gtggaacacc cagtcaccga agagaccacc ggcatcgacc tggtccgcga aatgttccgc | 960 |
| atcgcagaag ccacgagct ctccatcaag gaagatccag ctccacgcgg ccacgcattc | 1020 |
| gagttccgca tcaacggcga agacgctggc tccaacttca tgcctgcacc aggcaagatc | 1080 |
| accagctacc gcgagccaca gggcccaggc gtccgcatgg actccggtgt cgttgaaggt | 1140 |
| tccgaaatct ccggacagtt cgactccatg ctggcaaagc tgatcgtttg gggcgacacc | 1200 |
| cgcgagcagg ctctccagcg ctcccgccgt gcacttgcag agtacgttgt cgagggcatg | 1260 |
| ccaaccgtta tcccattcca ccagcacatc gtggaaaacc cagcattcgt gggcaacgac | 1320 |
| gaaggcttcg agatctacac caagtggatc gaagaggttt gggataaccc aatcgcacct | 1380 |
| tacgttgacg cttccgagct cgacgaagat gaggacaaga cccagcacac gaaggttgtt | 1440 |
| gtggagatca acggccgtcg cgttgaggtt gcactccag gcgatctggc actcggtggc | 1500 |
| accgctggtc ctaagaagaa ggccaagaag cgtcgcgcag tggtgcaaa ggctggcgta | 1560 |
| tccggcgatg cagtggcagc tccaatgcag ggcactgtca tcaaggtcaa cgtcgaagaa | 1620 |
| ggcgctgaag tcaacgaagg cgacaccgtt gttgtcctcg aggctatgaa gatggaaaac | 1680 |
| cctgtgaagg ctcataagtc cggaaccgta accggcctta ctgtcgctgc aggcgagggt | 1740 |
| gtcaacaagg gcgttgttct cctcgagatc aagtaa | 1776 |

<210> SEQ ID NO 51
<211> LENGTH: 591
<212> TYPE: PRT
<213> ORGANISM: Corynebacterium glutamicum

<400> SEQUENCE: 51

-continued

```
Met Ser Val Glu Thr Arg Lys Ile Thr Lys Val Leu Val Ala Asn Arg
1               5                   10                  15

Gly Glu Ile Ala Ile Arg Val Phe Arg Ala Ala Arg Asp Glu Gly Ile
                20                  25                  30

Gly Ser Val Ala Val Tyr Ala Glu Pro Asp Ala Asp Ala Pro Phe Val
            35                  40                  45

Ser Tyr Ala Asp Glu Ala Phe Ala Leu Gly Gly Gln Thr Ser Ala Glu
    50                  55                  60

Ser Tyr Leu Val Ile Asp Lys Ile Ile Asp Ala Ala Arg Lys Ser Gly
65                  70                  75                  80

Ala Asp Ala Ile His Pro Gly Tyr Gly Phe Leu Ala Glu Asn Ala Asp
                85                  90                  95

Phe Ala Glu Ala Val Ile Asn Glu Gly Leu Ile Trp Ile Gly Pro Ser
                100                 105                 110

Pro Glu Ser Ile Arg Ser Leu Gly Asp Lys Val Thr Ala Arg His Ile
                115                 120                 125

Ala Asp Thr Ala Lys Ala Pro Met Ala Pro Gly Thr Lys Glu Pro Val
            130                 135                 140

Lys Asp Ala Ala Glu Val Val Ala Phe Ala Glu Glu Phe Gly Leu Pro
145                 150                 155                 160

Ile Ala Ile Lys Ala Ala Phe Gly Gly Gly Gly Arg Gly Met Lys Val
                165                 170                 175

Ala Tyr Lys Met Glu Glu Val Ala Asp Leu Phe Glu Ser Ala Thr Arg
            180                 185                 190

Glu Ala Thr Ala Ala Phe Gly Arg Gly Glu Cys Phe Val Glu Arg Tyr
            195                 200                 205

Leu Asp Lys Ala Arg His Val Glu Ala Gln Val Ile Ala Asp Lys His
210                 215                 220

Gly Asn Val Val Ala Gly Thr Arg Asp Cys Ser Leu Gln Arg Arg
225                 230                 235                 240

Phe Gln Lys Leu Val Glu Glu Ala Pro Ala Pro Phe Leu Thr Asp Asp
                245                 250                 255

Gln Arg Glu Arg Leu His Ser Ser Ala Lys Ala Ile Cys Lys Glu Ala
            260                 265                 270

Gly Tyr Tyr Gly Ala Gly Thr Val Glu Tyr Leu Val Gly Ser Asp Gly
            275                 280                 285

Leu Ile Ser Phe Leu Glu Val Asn Thr Arg Leu Gln Val Glu His Pro
290                 295                 300

Val Thr Glu Glu Thr Thr Gly Ile Asp Leu Val Arg Glu Met Phe Arg
305                 310                 315                 320

Ile Ala Glu Gly His Glu Leu Ser Ile Lys Glu Asp Pro Ala Pro Arg
                325                 330                 335

Gly His Ala Phe Glu Phe Arg Ile Asn Gly Glu Asp Ala Gly Ser Asn
                340                 345                 350

Phe Met Pro Ala Pro Gly Lys Ile Thr Ser Tyr Arg Glu Pro Gln Gly
            355                 360                 365

Pro Gly Val Arg Met Asp Ser Gly Val Val Glu Gly Ser Glu Ile Ser
            370                 375                 380

Gly Gln Phe Asp Ser Met Leu Ala Lys Leu Ile Val Trp Gly Asp Thr
385                 390                 395                 400

Arg Glu Gln Ala Leu Gln Arg Ser Arg Arg Ala Leu Ala Glu Tyr Val
                405                 410                 415
```

Val Glu Gly Met Pro Thr Val Ile Pro Phe His Gln His Ile Val Glu
            420                 425                 430

Asn Pro Ala Phe Val Gly Asn Asp Glu Gly Phe Glu Ile Tyr Thr Lys
            435                 440                 445

Trp Ile Glu Glu Val Trp Asp Asn Pro Ile Ala Pro Tyr Val Asp Ala
450                 455                 460

Ser Glu Leu Asp Glu Asp Asp Lys Thr Pro Ala Gln Lys Val Val
465                 470                 475                 480

Val Glu Ile Asn Gly Arg Arg Val Glu Ala Leu Pro Gly Asp Leu
            485                 490                 495

Ala Leu Gly Gly Thr Ala Gly Pro Lys Lys Ala Lys Lys Arg Arg
            500                 505                 510

Ala Gly Gly Ala Lys Ala Gly Val Ser Gly Asp Ala Val Ala Ala Pro
515                 520                 525

Met Gln Gly Thr Val Ile Lys Val Asn Val Glu Glu Gly Ala Glu Val
            530                 535                 540

Asn Glu Gly Asp Thr Val Val Leu Glu Ala Met Lys Met Glu Asn
545                 550                 555                 560

Pro Val Lys Ala His Lys Ser Gly Thr Val Thr Gly Leu Thr Val Ala
            565                 570                 575

Ala Gly Glu Gly Val Asn Lys Gly Val Val Leu Leu Glu Ile Lys
            580                 585                 590

<210> SEQ ID NO 52
<211> LENGTH: 340
<212> TYPE: PRT
<213> ORGANISM: Acinetobacter sp.

<400> SEQUENCE: 52

Met Ser Asn His Gln Ile Arg Ala Tyr Ala Ala Met Gln Ala Gly Glu
1               5                   10                  15

Gln Val Val Pro Tyr Gln Phe Asp Ala Gly Glu Leu Lys Ala His Gln
            20                  25                  30

Val Glu Val Lys Val Glu Tyr Cys Gly Leu Cys His Ser Asp Leu Ser
        35                  40                  45

Val Ile Asn Asn Glu Trp Gln Ser Ser Val Tyr Pro Ala Val Ala Gly
    50                  55                  60

His Glu Ile Ile Gly Thr Ile Ala Leu Gly Ser Glu Ala Lys Gly
65                  70                  75                  80

Leu Lys Leu Gly Gln Arg Val Gly Ile Gly Trp Thr Ala Glu Thr Cys
            85                  90                  95

Gln Ala Cys Asp Pro Cys Ile Gly Gly Asn Gln Val Leu Cys Thr Gly
            100                 105                 110

Glu Lys Lys Ala Thr Ile Ile Gly His Ala Gly Gly Phe Ala Asp Lys
            115                 120                 125

Val Arg Ala Gly Trp Gln Trp Val Ile Pro Leu Pro Asp Asp Leu Asp
130                 135                 140

Pro Glu Ser Ala Gly Pro Leu Leu Cys Gly Gly Ile Thr Val Leu Asp
145                 150                 155                 160

Pro Leu Leu Lys His Lys Ile Gln Ala Thr His His Val Gly Val Ile
            165                 170                 175

Gly Ile Gly Gly Leu Gly His Ile Ala Ile Lys Leu Leu Lys Ala Trp
            180                 185                 190

Gly Cys Glu Ile Thr Ala Phe Ser Ser Asn Pro Asp Lys Thr Glu Glu
            195                 200                 205

```
Leu Lys Ala Asn Gly Ala Asp Gln Val Val Asn Ser Arg Asp Ala Gln
            210                 215                 220

Ala Ile Lys Gly Thr Arg Trp Lys Leu Ile Ile Leu Ser Thr Ala Asn
225                 230                 235                 240

Gly Thr Leu Asn Val Lys Ala Tyr Leu Asn Thr Leu Ala Pro Lys Gly
                245                 250                 255

Ser Leu His Phe Leu Gly Val Thr Leu Glu Pro Ile Pro Val Ser Val
            260                 265                 270

Gly Ala Ile Met Gly Gly Ala Lys Ser Val Thr Ser Ser Pro Thr Gly
            275                 280                 285

Ser Pro Leu Ala Leu Arg Gln Leu Leu Gln Phe Ala Ala Arg Lys Asn
            290                 295                 300

Ile Ala Pro Gln Val Glu Leu Phe Pro Met Ser Gln Leu Asn Glu Ala
305                 310                 315                 320

Ile Glu Arg Leu His Ser Gly Gln Ala Arg Tyr Arg Ile Val Leu Lys
                325                 330                 335

Ala Asp Phe Asp
            340

<210> SEQ ID NO 53
<211> LENGTH: 314
<212> TYPE: PRT
<213> ORGANISM: Acinetobacter baylyi

<400> SEQUENCE: 53

Met Ala Thr Thr Asn Val Ile His Ala Tyr Ala Ala Met Gln Ala Gly
1               5                   10                  15

Glu Ala Leu Val Pro Tyr Ser Phe Asp Ala Gly Glu Leu Gln Pro His
            20                  25                  30

Gln Val Glu Val Lys Val Glu Tyr Cys Gly Leu Cys His Ser Asp Val
        35                  40                  45

Ser Val Leu Asn Asn Glu Trp His Ser Ser Val Tyr Pro Val Val Ala
    50                  55                  60

Gly His Glu Val Ile Gly Thr Ile Thr Gln Leu Gly Ser Glu Ala Lys
65                  70                  75                  80

Gly Leu Lys Ile Gly Gln Arg Val Gly Ile Gly Trp Thr Ala Glu Ser
                85                  90                  95

Cys Gln Ala Cys Asp Gln Cys Ile Ser Gly Gln Gln Val Leu Cys Thr
            100                 105                 110

Gly Glu Asn Thr Ala Thr Ile Ile Gly His Ala Gly Gly Phe Ala Asp
        115                 120                 125

Lys Val Arg Ala Gly Trp Gln Trp Val Ile Pro Leu Pro Asp Glu Leu
    130                 135                 140

Asp Pro Thr Ser Ala Gly Pro Leu Leu Cys Gly Gly Ile Thr Val Phe
145                 150                 155                 160

Asp Pro Ile Leu Lys His Gln Ile Gln Ala Ile His His Val Ala Val
                165                 170                 175

Ile Gly Ile Gly Gly Leu Gly His Met Ala Ile Lys Leu Leu Lys Ala
            180                 185                 190

Trp Gly Cys Glu Ile Thr Ala Phe Ser Ser Asn Pro Asn Lys Thr Asp
        195                 200                 205

Glu Leu Lys Ala Met Gly Ala Asp His Val Val Asn Ser Arg Asp Asp
    210                 215                 220

Ala Glu Ile Lys Ser Gln Gln Gly Lys Phe Asp Leu Leu Leu Ser Thr
```

```
                225                 230                 235                 240

Val Asn Val Pro Leu Asn Trp Asn Ala Tyr Leu Asn Thr Leu Ala Pro
                    245                 250                 255

Asn Gly Thr Phe His Phe Leu Gly Val Val Met Glu Pro Ile Pro Val
                260                 265                 270

Pro Val Gly Ala Leu Leu Gly Gly Ala Lys Ser Leu Thr Ala Ser Pro
                275                 280                 285

Thr Gly Ser Pro Ala Ala Leu Arg Lys Leu Leu Glu Phe Ala Ala Arg
                290                 295                 300

Lys Asn Ile Ala Pro Gln Ile Glu Met Tyr
305                 310

<210> SEQ ID NO 54
<211> LENGTH: 341
<212> TYPE: PRT
<213> ORGANISM: Acinetobacter baylyi

<400> SEQUENCE: 54

Met Ala Thr Thr Asn Val Ile His Ala Tyr Ala Ala Met Gln Ala Gly
1               5                   10                  15

Glu Ala Leu Val Pro Tyr Ser Phe Asp Ala Gly Glu Leu Gln Pro His
                20                  25                  30

Gln Val Glu Val Lys Val Glu Tyr Cys Gly Leu Cys His Ser Asp Val
            35                  40                  45

Ser Val Leu Asn Asn Glu Trp His Ser Ser Val Tyr Pro Val Val Ala
    50                  55                  60

Gly His Glu Val Ile Gly Thr Ile Thr Gln Leu Gly Ser Glu Ala Lys
65                  70                  75                  80

Gly Leu Lys Ile Gly Gln Arg Val Gly Ile Gly Trp Thr Ala Glu Ser
                85                  90                  95

Cys Gln Ala Cys Asp Gln Cys Ile Ser Gly Gln Gln Val Leu Cys Thr
            100                 105                 110

Gly Glu Asn Thr Ala Thr Ile Ile Gly His Ala Gly Gly Phe Ala Asp
        115                 120                 125

Lys Val Arg Ala Gly Trp Gln Trp Val Ile Pro Leu Pro Asp Glu Leu
    130                 135                 140

Asp Pro Thr Ser Ala Gly Pro Leu Leu Cys Gly Gly Ile Thr Val Phe
145                 150                 155                 160

Asp Pro Ile Leu Lys His Gln Ile Gln Ala Ile His His Val Ala Val
                165                 170                 175

Ile Gly Ile Gly Gly Leu Gly His Met Ala Ile Lys Leu Leu Lys Ala
            180                 185                 190

Trp Gly Cys Glu Ile Thr Ala Phe Ser Ser Asn Pro Asn Lys Thr Asp
        195                 200                 205

Glu Leu Lys Ala Met Gly Ala Asp His Val Val Asn Ser Arg Asp Asp
    210                 215                 220

Ala Glu Ile Lys Ser Gln Gln Gly Lys Phe Asp Leu Leu Leu Ser Thr
225                 230                 235                 240

Val Asn Val Pro Leu Asn Trp Asn Ala Tyr Leu Asn Thr Leu Ala Pro
                245                 250                 255

Asn Gly Thr Phe His Phe Leu Gly Val Val Met Glu Pro Ile Pro Val
            260                 265                 270

Pro Val Gly Ala Leu Leu Gly Gly Ala Lys Ser Leu Thr Ala Ser Pro
        275                 280                 285
```

```
Thr Gly Ser Pro Ala Ala Leu Arg Lys Leu Leu Glu Phe Ala Ala Arg
    290                 295                 300

Lys Asn Ile Ala Pro Gln Ile Glu Met Tyr Pro Met Ser Glu Leu Asn
305                 310                 315                 320

Glu Ala Ile Glu Arg Leu His Ser Gly Gln Ala Arg Tyr Arg Ile Val
                325                 330                 335

Leu Lys Ala Asp Phe
            340

<210> SEQ ID NO 55
<211> LENGTH: 4805
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
```

| | | | | | |
|---|---|---|---|---|---|
| tgtaggctgg | agctgcttcg | aagttcctat | actttctaga | gaataggaac | ttcggaatag | 60 |
| gaacttcgaa | ctgcaggtcg | acggatcccc | ggaatattta | aatcatttgt | acttttgaa | 120 |
| cagcagagtc | gcattatggc | caccgaagcc | caggctgttg | acagaacgt | agttgacttc | 180 |
| tgcattacgg | ccctcgttag | gaacgtaatc | caggtcgcat | tccggatccg | cctctttgta | 240 |
| gccgatggtc | ggcggaatga | aaccctcttc | aatagctttg | gcacagataa | tcgcttcgac | 300 |
| tgcaccgcca | gcgcccagca | ggtggccggt | catgctcttg | gtgctagaca | ccggcacttt | 360 |
| gtaggcgtat | tcacccagga | ccgtcttgat | cgcttgggtt | tcgaagctgt | cattgtacgc | 420 |
| cgtgctcgta | ccgtgcgcgt | tgatatagga | aatgtcctct | gggcggacat | tatcttcttc | 480 |
| cattgccagt | tcattgcac | gtgcaccacc | ttcaccattc | ggcgctgggc | tcgtgatatg | 540 |
| atatgcgtcg | caggtcgcac | catagccaac | gatctcggca | tagattttgg | caccacgctt | 600 |
| cagcgcgtgc | tccaactctt | ccaagataac | gataccgctg | ccctcgccca | tcacaaaacc | 660 |
| gctgcgatcc | ttatcgaacg | ggatgctggc | gcgcttcggg | tcctcagatt | tggtcacggc | 720 |
| cttcatcgag | gcaaaacccg | ccaggctcaa | cggggtgata | cctgcttcgc | taccaccaga | 780 |
| gatcataacg | tcgctataac | caaacttaat | gttacgaag | gactcaccaa | tgctgttgtt | 840 |
| cgcgctcgca | catgcggtga | caatggtcgt | gcaaatacct | ttagcgccat | aacgaatcgc | 900 |
| cagattaccg | cttgccatat | tcgcaatgat | catcggaata | gtcatagggc | tcacacgacc | 960 |
| cggacctttg | gtaatcagct | tttcatcctg | cttctcaatg | gtgccgatgc | cgccaatgcc | 1020 |
| gctaccaaca | atgacgccga | aacgattctt | atcaatcgac | tccaggtcca | gtttgctgtc | 1080 |
| cttgattgcc | tcatccgccg | caacgatcgc | aaactggcta | aaacggtcca | tacggttcgc | 1140 |
| ctcacgcttg | tcgataaagt | cctccggggt | gaagtccttc | acttcggcag | ccagcttaac | 1200 |
| tttgaaatcg | gttgcgtcaa | acgctttgat | cttgtcaatg | ccacatttac | cctctttgat | 1260 |
| gctgcaccag | aagctatcag | cgttgttacc | caccggcgtc | actgcaccaa | tacccgtaat | 1320 |
| gacaacgcgg | cgattcattt | tgttgcctcc | ttttagaacg | cggaagtatc | ctggaacaaa | 1380 |
| ccgactttca | aatcgtgtgc | ggtatagatc | aggcgaccat | ccaccagaac | ctcaccgtcc | 1440 |
| gccaggccca | tgatcaggcg | acggtttacg | atacgtttga | aatgaatacg | ataggtgact | 1500 |
| ttcctggctg | tcggcagaac | ctggccggta | aatttcactt | cgcccacgcc | cagagcgcgg | 1560 |
| cctttgcctt | cgccgcccaa | ccagcccagg | tagaatccca | ccaattgcca | catagcatcc | 1620 |
| agacccagac | aaccgggcat | caccggatcg | ccgataaagt | ggcatccgaa | gaaccataga | 1680 |

```
tccggattga tatccagctc ggcttcgaca tagcctttgt cgaaattgcc gcccgtttcg    1740
gtcatcttaa cgacgcggtc catcatcagc atgttcggtg cagggagttg cggcccttta    1800
gcgccaaaca gttcaccacg accagaggca agaaggtctt cttttgtata ggattcgcgt    1860
ttatctacca tgtttatgt aaaccttaaa attaaaccat gtacattccg ccgttgacgt     1920
gcagagtctc accagtgatg taactcgctt cgtcagaggc taaaaatgca accgcactgg    1980
cgatttcctg agcgccgccg aggcgacccg caggcacctg cgccaggata cccgcacgct    2040
gatcgtcaga cagcgcacgc gtcatgtccg tttcaataaa acccggagcc acaacattga    2100
cagtaatacc acgggacgca acttcacgcg ccagtgattt actgaaaccg atcaggcccg    2160
ctttcgccgc agcgtagttt gcctgacctg catttcccat ggtaccaacc acagaaccaa    2220
tagtgataat gcgaccacaa cgcttttca tcatagcgcg cattaccgct tttgacaggc     2280
ggaaaacgga tgataagttg gtttcgataa tatcgttcca ctcatcatct ttcattcgca    2340
tcaacagatt atcacgagtg ataccggcat tattaaccag gatatccact tcaccaaatt    2400
ctgcgcgaat attttccaga acagattcaa tagatgcagg atcggtcaca ttcaacatca    2460
aacctttccc gttagcacct aaatagtcgc taatgttctt cgcaccattt tcactggtcg    2520
cagtcccgat aactttcgcg ccgcgggcaa cgagagtctc tgcaattgcg cggcctatgc    2580
cacggcttgc accagtcacc agcgcaatct ttccttcaaa gctcatggtt ttcctctttt    2640
attgcgtaag tgccgcagac agcgccgccg gctcgttcag cgccgacgct gtcagggtgt    2700
cgacaatacg tttcgtcaga ccagtgagga ctttacctgg acccacttca taaagatgtt    2760
caacgccctg cgccgcgata aattccacgc tcttcgtcca ctgtaccgga ttgtacaact    2820
ggcgaaccag cgcatcgcgg atagcggcgg catcggtttc acatttcacg tcaacgttgt    2880
tcactaccgg caccgttggc gcgctaaagg taattttggc taattcaacc gccagcttat    2940
ctgccgctgg tttcatcagc gcgcagtgcg acggtacgct caccggcagc ggcagcgcgc    3000
gtttcgcgcc agcggcttta caggctgcgc ccgcacgttc taccgcctct ttatgcccgg    3060
cgataaccac ctgtcccggc gagttaaagt taaccggcga acaacctgc ccttcggcag     3120
attcttcaca ggctttagca atagaggcat catccagccc gatgatcgca gacatgccgc    3180
cagtgccttc cggaaccgct tcctgcatga atttaccgcg catttccacc agacgaacgg    3240
catcagcaaa gttgatgacg ccagcgcaaa ccagcgcgga atattcgccc aggctgtgac    3300
ctgccattaa cgcaggcatt ttaccgccct gctgctgcca aacgcgccaa agcgcgacgg    3360
aagcggttaa taacgccggc tgcgtctgcc aggttttatt cagttcttcc gctgaccttt    3420
gctgggtgag cgcccacaga tcatatccca gagccgcaga agcttcagca aacgtttctt    3480
ctacgatagg gtaatttgcc gccatctcgg ccaacatccc aacgctctga gaaccctgac    3540
cggggaacac aaatgcaaat tgcgtcatgt ttaaatcctt atactagaaa cgaatcagcg    3600
cggagcccca ggtgaatcca cccccgaagg cttcaagcaa taccagctga ccggctttaa    3660
ttcgcccgtc acgcacggct tcatccagcg cgcacggcac agaagccgcg gaggtattgc    3720
cgtgcctgtc cagcgtgacg acgacattgt ccatcgacat gccgagtttt ttcgctgtcg    3780
cgctaatgat acgcaggtta gcctgatgcg gcaccagcca atcagttcct gagcgatcca    3840
ggttattagc cgccagcgtc tcatcgacaa tatgcgccag ttcagtgacc gccactttaa    3900
agacttcatt gcccgccatt gtcaggtaaa tcgggttatc cggatttacg cgatcggcat    3960
tcggcagggt cagtaattca ccgtaacggc catcggcatg aagatgagtg gagataatac    4020
ccggttcttc agaagcgctc agtacggccg cgcctgcgcc atcgccgaaa ataatgatcg    4080
```

-continued

```
taccgcgatc gccaggatcg caagtgcggg ctaatacatc ggaaccgacc accagcgcgt     4140
gtttaaccgc gccggattta acgtactggt cggcgatgct taacgcgtag gtgaaacctg     4200
cgcacgctgc cgcgacatca aacgccgggc aacctttaat accgagcata ctttgaatct     4260
gacatgccgc gcttggaaat gcatgcgttg ctgatgtggt agccaccaca atcaagccaa     4320
tttggtcttt atcgatcccc gccatctcaa tcgcgcgatt cgcagcggta agcccatcg     4380 tcgcgacagt ttcattcggc gcggcgatat ggcgtttacg aatacctgta cgagtgacaa     4440
tccactcgtc agaggtctca accatttttt ccagatcggc gttagtccgc acttgttcgg     4500
gcagatagct gccagtacca ataatcttcg tatacatgta cgctcagtca ctaaattact     4560
cgatatcaat cacatcaaat tcgacttctg gattgacgtc agcatcgtaa tcaatgcctt     4620
caatgccaaa gccaaacagc ttgatgaact cttctttgta catgtcgtaa tcggtcagct     4680
cacgcaggtt ctctgtggtg atttgtggcc acagatcacg gcagtgctgc tgaatgtcat     4740
cacgcagttc ccagtcatcc aaacgcagac gattgtgatc atccacttcc ggcgctgaac     4800
catct                                                                 4805
```

<210> SEQ ID NO 56
<211> LENGTH: 239
<212> TYPE: PRT
<213> ORGANISM: Escherichia coli

<400> SEQUENCE: 56

```
Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
                20                  25                  30

Ala Glu Arg Glu Leu Ser Glu Leu Ile Gly Val Thr Arg Thr Thr Leu
            35                  40                  45

Arg Glu Val Leu Gln Arg Leu Ala Arg Asp Gly Trp Leu Thr Ile Gln
        50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95

Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
            180                 185                 190

Tyr His Lys Leu Ser Ala Leu Cys Ser Glu Gly Ala His Asp Gln Val
        195                 200                 205

Tyr Glu Thr Val Arg Arg Tyr Gly His Glu Ser Gly Glu Ile Trp His
    210                 215                 220

Arg Met Gln Lys Asn Leu Pro Gly Asp Leu Ala Ile Gln Gly Arg
225                 230                 235
```

<210> SEQ ID NO 57
<211> LENGTH: 342
<212> TYPE: PRT
<213> ORGANISM: Synechococcus elongatus

<400> SEQUENCE: 57

Met Ala Phe Gly Leu Ile Gly His Leu Thr Ser Leu Glu Gln Ala Arg
1               5                   10                  15

Asp Val Trp Arg Arg Met Gly Tyr Asp Glu Tyr Ala Asp Gln Gly Leu
            20                  25                  30

Glu Phe Trp Ser Ser Ala Pro Pro Gln Ile Val Asp Glu Ile Thr Val
        35                  40                  45

Thr Ser Ala Thr Gly Lys Val Ile His Gly Arg Tyr Ile Glu Ser Cys
50                  55                  60

Phe Leu Pro Glu Met Leu Ala Ala Arg Arg Phe Lys Thr Ala Thr Arg
65                  70                  75                  80

Lys Val Leu Asn Ala Met Ser His Ala Gln Lys His Gly Ile Asp Ile
                85                  90                  95

Ser Ala Leu Gly Gly Phe Thr Ser Ile Ile Phe Glu Asn Phe Asp Leu
            100                 105                 110

Ala Ser Leu Arg Gln Val Arg Asp Thr Thr Leu Glu Phe Glu Arg Phe
        115                 120                 125

Thr Thr Gly Asn Thr His Thr Ala Tyr Val Ile Cys Arg Gln Val Glu
130                 135                 140

Ala Ala Ala Lys Thr Leu Gly Ile Asp Ile Thr Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Gly Val Val Glu His Cys
            260                 265                 270

Phe Asp Ile Asp Trp Gln Ile Met Ser Ala Ala Glu Met Ala Arg Pro
        275                 280                 285

Glu Arg Gln Met Phe Ala Cys Phe Ala Glu Ala Met Leu Leu Glu Phe
290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340

<210> SEQ ID NO 58
<211> LENGTH: 342
<212> TYPE: PRT

<213> ORGANISM: Synechococcus elongatus

<400> SEQUENCE: 58

| Met | Ala | Phe | Gly | Leu | Ile | Gly | His | Leu | Thr | Ser | Leu | Glu | Gln | Ala | Arg |
|---|---|---|---|---|---|---|---|---|---|---|---|---|---|---|---|
| 1 | | | | 5 | | | | | 10 | | | | | 15 | |
| Asp | Val | Trp | Arg | Arg | Leu | Gly | Tyr | Asp | Glu | Tyr | Ala | Asp | Gln | Gly | Leu |
| | | | 20 | | | | | 25 | | | | | 30 | | |
| Glu | Phe | Trp | Ser | Ser | Ala | Pro | Pro | Gln | Ile | Val | Asp | Glu | Ile | Thr | Val |
| | | | 35 | | | | | 40 | | | | | 45 | | |
| Thr | Ser | Ala | Thr | Gly | Lys | Val | Ile | His | Gly | Arg | Tyr | Ile | Glu | Ser | Gly |
| | 50 | | | | | 55 | | | | | 60 | | | | |
| Phe | Leu | Pro | Glu | Met | Leu | Ala | Ala | Arg | Arg | Phe | Lys | Thr | Ala | Thr | Arg |
| 65 | | | | | 70 | | | | | 75 | | | | | 80 |
| Lys | Val | Leu | Asn | Ala | Met | Ser | His | Ala | Gln | Lys | His | Gly | Ile | Asp | Ile |
| | | | | 85 | | | | | 90 | | | | | 95 | |
| Ser | Ala | Leu | Gly | Gly | Phe | Thr | Ser | Ile | Ile | Phe | Glu | Asn | Phe | Asp | Leu |
| | | | 100 | | | | | 105 | | | | | 110 | | |
| Ala | Lys | Leu | Arg | Gln | Val | Arg | Asp | Thr | Thr | Leu | Glu | Phe | Glu | Arg | Phe |
| | | | 115 | | | | | 120 | | | | | 125 | | |
| Thr | Thr | Gly | Asn | Thr | His | Thr | Ala | Tyr | Val | Ile | Cys | Arg | Gln | Val | Glu |
| | 130 | | | | | 135 | | | | | 140 | | | | |
| Ala | Ala | Ala | Lys | Thr | Leu | Gly | Ile | Asp | Ile | Ala | Gln | Ala | Thr | Val | Ala |
| 145 | | | | | 150 | | | | | 155 | | | | | 160 |
| Val | Val | Gly | Ala | Thr | Gly | Asp | Ile | Gly | Ser | Ala | Val | Cys | Arg | Trp | Leu |
| | | | | 165 | | | | | 170 | | | | | 175 | |
| Asp | Leu | Lys | Leu | Gly | Val | Gly | Asp | Leu | Ile | Leu | Thr | Ala | Arg | Asn | Gln |
| | | | 180 | | | | | 185 | | | | | 190 | | |
| Glu | Arg | Leu | Asp | Asn | Leu | Gln | Ala | Glu | Leu | Gly | Arg | Gly | Lys | Ile | Leu |
| | | | 195 | | | | | 200 | | | | | 205 | | |
| Pro | Leu | Glu | Ala | Ala | Leu | Pro | Glu | Ala | Asp | Phe | Ile | Val | Trp | Val | Ala |
| | 210 | | | | | 215 | | | | | 220 | | | | |
| Ser | Met | Pro | Gln | Gly | Val | Val | Ile | Asp | Pro | Ala | Thr | Leu | Lys | Gln | Pro |
| 225 | | | | | 230 | | | | | 235 | | | | | 240 |
| Cys | Val | Leu | Ile | Asp | Gly | Gly | Tyr | Pro | Lys | Asn | Leu | Gly | Ser | Lys | Val |
| | | | | 245 | | | | | 250 | | | | | 255 | |
| Gln | Gly | Glu | Gly | Ile | Tyr | Val | Leu | Asn | Gly | Gly | Val | Val | Glu | His | Cys |
| | | | 260 | | | | | 265 | | | | | 270 | | |
| Phe | Asp | Ile | Asp | Trp | Gln | Ile | Met | Ser | Leu | Ala | Glu | Met | Ala | Arg | Pro |
| | | | 275 | | | | | 280 | | | | | 285 | | |
| Glu | Arg | Gln | Met | Phe | Ala | Cys | Phe | Ala | Glu | Ala | Met | Leu | Leu | Glu | Phe |
| | 290 | | | | | 295 | | | | | 300 | | | | |
| Glu | Gly | Trp | His | Thr | Asn | Phe | Ser | Trp | Gly | Arg | Asn | Gln | Ile | Thr | Ile |
| 305 | | | | | 310 | | | | | 315 | | | | | 320 |
| Glu | Lys | Met | Glu | Ala | Ile | Gly | Glu | Ala | Ser | Val | Arg | His | Gly | Phe | Gln |
| | | | | 325 | | | | | 330 | | | | | 335 | |
| Pro | Leu | Ala | Leu | Ala | Ile 340 | | | | | | | | | | |

<210> SEQ ID NO 59
<211> LENGTH: 342
<212> TYPE: PRT
<213> ORGANISM: Synechococcus elongatus

<400> SEQUENCE: 59

| Met | Ala | Phe | Gly | Leu | Ile | Gly | His | Ala | Thr | Ser | Leu | Glu | Gln | Ala | Arg |
|---|---|---|---|---|---|---|---|---|---|---|---|---|---|---|---|

```
              1               5                  10                 15
            Asp Val Trp Arg Arg Leu Gly Tyr Asp Glu Tyr Ala Asp Gln Gly Leu
                           20                  25                 30

Glu Phe Trp Ser Ser Ala Pro Pro Gln Ile Val Asp Glu Ile Thr Val
                           35                  40                 45

Thr Ser Ala Thr Gly Lys Val Ile His Gly Arg Tyr Ile Glu Ser Gly
                50                          55                 60

Phe Leu Pro Glu Met Leu Ala Ala Arg Arg Phe Lys Thr Ala Thr Arg
             65                 70                  75                 80

Lys Val Leu Asn Ala Met Ser His Ala Gln Lys His Gly Ile Asp Ile
                           85                  90                 95

Ser Ala Leu Gly Gly Phe Thr Ser Ile Ile Phe Glu Asn Phe Asp Leu
                          100                 105                110

Ala Lys Leu Arg Gln Val Arg Asp Thr Thr Leu Glu Phe Glu Arg Phe
                          115                 120                125

Thr Thr Gly Asn Thr His Thr Ala Tyr Val Ile Cys Arg Gln Val Glu
                130                         135                140

Ala Ala Ala Lys Thr Leu Gly Ile Asp Ile Ala Gln Ala Thr Val Ala
            145                 150                 155                160

Val Val Gly Ala Thr Gly Asp Ile Gly Ser Ala Val Cys Arg Trp Leu
                               165                 170                175

Asp Leu Lys Leu Gly Val Gly Asp Leu Ile Leu Thr Ala Arg Asn Gln
                           180                 185                190

Glu Arg Leu Asp Asn Leu Gln Ala Glu Leu Gly Arg Gly Lys Ile Leu
                           195                 200                205

Pro Leu Glu Ala Ala Leu Pro Glu Ala Asp Phe Ile Val Trp Val Ala
            210                 215                 220

Ser Met Pro Gln Gly Val Val Ile Asp Pro Ala Thr Leu Lys Gln Pro
            225                 230                 235                240

Cys Val Leu Ile Asp Gly Gly Tyr Pro Lys Asn Leu Gly Ser Lys Val
                               245                 250                255

Gln Gly Glu Gly Ile Tyr Val Leu Asn Gly Gly Val Val Glu His Cys
                           260                 265                270

Phe Asp Ile Asp Trp Gln Ile Met Ser Leu Ala Glu Met Ala Arg Pro
                           275                 280                285

Glu Arg Gln Met Phe Ala Cys Phe Ala Glu Ala Met Leu Leu Glu Phe
                           290                 295                300

Glu Gly Trp His Thr Asn Phe Ser Trp Gly Arg Asn Gln Ile Thr Ile
            305                 310                 315                320

Glu Lys Met Glu Ala Ile Gly Glu Ala Ser Val Arg His Gly Phe Gln
                           325                 330                335

Pro Leu Ala Leu Ala Ile
                          340

<210> SEQ ID NO 60
<211> LENGTH: 342
<212> TYPE: PRT
<213> ORGANISM: Synechococcus elongatus

<400> SEQUENCE: 60

Met Ala Phe Gly Leu Ile Gly His Leu Thr Ser Leu Glu Gln Ala Arg
 1                5                  10                 15

Leu Val Trp Arg Arg Leu Gly Tyr Asp Glu Tyr Ala Asp Gln Gly Leu
                 20                  25                 30
```

```
Glu Phe Trp Ser Ser Ala Pro Pro Gln Ile Val Asp Glu Ile Thr Val
            35                  40                  45

Thr Ser Ala Thr Gly Lys Val Ile His Gly Arg Tyr Ile Glu Ser Gly
 50                  55                  60

Phe Leu Pro Glu Met Leu Ala Ala Arg Arg Phe Lys Thr Ala Thr Arg
 65                  70                  75                  80

Lys Val Leu Asn Ala Met Ser His Ala Gln Lys His Gly Ile Asp Ile
                 85                  90                  95

Ser Ala Leu Gly Gly Phe Thr Ser Ile Ile Phe Glu Asn Phe Asp Leu
            100                 105                 110

Ala Lys Leu Arg Gln Val Arg Asp Thr Thr Leu Glu Phe Glu Arg Phe
        115                 120                 125

Thr Thr Gly Asn Thr His Thr Ala Tyr Val Ile Cys Arg Gln Val Glu
130                 135                 140

Ala Ala Ala Lys Thr Leu Gly Ile Asp Ile Ala Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Gly Val Val Glu His Cys
            260                 265                 270

Phe Asp Ile Asp Trp Gln Ile Met Ser Leu Ala Glu Met Ala Arg Pro
        275                 280                 285

Glu Arg Gln Met Phe Ala Cys Phe Ala Glu Ala Met Leu Leu Glu Phe
290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340

<210> SEQ ID NO 61
<211> LENGTH: 342
<212> TYPE: PRT
<213> ORGANISM: Synechococcus elongatus

<400> SEQUENCE: 61

Met Ala Phe Gly Leu Ile Gly His Ala Thr Ser Leu Glu Gln Ala Arg
1               5                   10                  15

Asp Val Trp Arg Arg Met Gly Tyr Val Glu Tyr Ala Asp Gln Gly Leu
            20                  25                  30

Glu Phe Trp Ser Ser Ala Pro Pro Gln Ile Val Asp Glu Ile Thr Val
        35                  40                  45

Thr Ser Ala Thr Gly Lys Val Ile His Gly Arg Tyr Ile Glu Ser Gly
50                  55                  60
```

```
Phe Leu Pro Glu Met Leu Ala Ala Arg Arg Phe Lys Thr Ala Thr Arg
 65                  70                  75                  80

Lys Val Leu Asn Ala Met Ser His Ala Gln Lys His Gly Ile Asp Ile
                 85                  90                  95

Ser Ala Leu Gly Gly Phe Thr Ser Ile Ile Phe Glu Asn Phe Asp Leu
            100                 105                 110

Ala Lys Leu Arg Gln Val Arg Asp Thr Thr Leu Glu Phe Glu Arg Phe
        115                 120                 125

Thr Thr Gly Asn Thr His Thr Ala Tyr Val Ile Cys Arg Gln Val Glu
130                 135                 140

Ala Ala Ala Lys Thr Leu Gly Ile Asp Ile Thr Leu Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
    210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Val Val Glu His Cys
            260                 265                 270

Phe Asp Ile Asp Trp Gln Ile Met Ser Leu Ala Glu Met Ala Arg Pro
        275                 280                 285

Glu Arg Gln Met Phe Ala Cys Phe Ala Glu Ala Met Leu Leu Glu Phe
    290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340

<210> SEQ ID NO 62
<211> LENGTH: 342
<212> TYPE: PRT
<213> ORGANISM: Synechococcus elongatus

<400> SEQUENCE: 62

Met Ala Phe Gly Leu Ile Gly His Leu Thr Ser Leu Glu Gln Ala Arg
 1               5                  10                  15

Asp Val Trp Arg Arg Met Gly Tyr Pro Glu Tyr Ala Asp Gln Gly Met
                20                  25                  30

Glu Phe Trp Ser Ser Ala Pro Pro Gln Ile Val Asp Glu Ile Thr Val
            35                  40                  45

Thr Ser Ala Thr Gly Lys Val Ile His Gly Arg Tyr Ile Glu Ser Gly
        50                  55                  60

Phe Leu Pro Glu Met Leu Ala Ala Arg Arg Phe Lys Thr Ala Thr Arg
 65                  70                  75                  80

Lys Val Leu Asn Ala Met Ser His Ala Gln Lys His Gly Ile Asp Ile
```

```
                    85                  90                  95

Ser Ala Leu Gly Gly Phe Thr Ser Ile Ile Phe Glu Asn Phe Asp Leu
                100                 105                 110

Ala Lys Leu Arg Gln Val Arg Asp Thr Thr Leu Glu Phe Glu Arg Phe
                115                 120                 125

Thr Thr Gly Asn Thr His Thr Ala Tyr Val Ile Cys Arg Gln Val Glu
            130                 135                 140

Ala Ala Ala Lys Thr Leu Gly Ile Asp Ile Ala Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
            195                 200                 205

Pro Leu Glu Ala Ala Leu Pro Glu Ala Asp Phe Ile Val Trp Val Ala
    210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Gly Val Val Glu His Cys
            260                 265                 270

Phe Asp Ile Asp Trp Gln Ile Met Ser Leu Ala Glu Met Ala Arg Pro
        275                 280                 285

Glu Arg Gln Met Phe Ala Cys Phe Ala Glu Ala Met Leu Leu Glu Phe
        290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340

<210> SEQ ID NO 63
<211> LENGTH: 342
<212> TYPE: PRT
<213> ORGANISM: Synechococcus elongatus

<400> SEQUENCE: 63

Met Ala Phe Gly Leu Ile Gly His Ala Thr Ser Leu Glu Gln Ala Arg
1               5                   10                  15

Leu Val Trp Arg Arg Met Gly Tyr Val Glu Tyr Ala Asp Gln Gly Leu
                20                  25                  30

Glu Phe Trp Ser Ser Ala Pro Pro Gln Ile Val Asp Glu Ile Thr Val
            35                  40                  45

Thr Ser Ala Thr Gly Lys Val Ile His Gly Arg Tyr Ile Glu Ser Gly
        50                  55                  60

Phe Leu Pro Glu Met Leu Ala Ala Arg Arg Phe Lys Thr Ala Thr Arg
65                  70                  75                  80

Lys Val Leu Asn Ala Met Ser His Ala Gln Lys His Gly Ile Asp Ile
                85                  90                  95

Ser Ala Leu Gly Gly Phe Thr Ser Ile Ile Phe Glu Asn Phe Asp Leu
                100                 105                 110
```

```
Ala Lys Leu Arg Gln Val Arg Asp Thr Thr Leu Glu Phe Glu Arg Phe
            115                 120                 125

Thr Thr Gly Asn Thr His Thr Ala Tyr Val Ile Cys Arg Gln Val Glu
        130                 135                 140

Ala Ala Ala Lys Thr Leu Gly Ile Asp Ile Ala Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
    210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Gly Val Val Glu His Cys
            260                 265                 270

Phe Asp Ile Asp Trp Gln Ile Met Ser Leu Ala Glu Met Ala Arg Pro
        275                 280                 285

Glu Arg Gln Met Phe Ala Cys Phe Ala Glu Ala Met Leu Leu Glu Phe
    290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340

<210> SEQ ID NO 64
<211> LENGTH: 342
<212> TYPE: PRT
<213> ORGANISM: Synechococcus elongatus

<400> SEQUENCE: 64

Met Ala Phe Gly Leu Ile Gly His Leu Thr Ser Leu Glu Gln Ala Arg
1               5                   10                  15

Asp Val Trp Arg Arg Met Gly Tyr Glu Glu Tyr Ala Asp Gln Gly Leu
            20                  25                  30

Glu Phe Trp Ser Ser Ala Pro Pro Gln Ile Val Asp Glu Ile Thr Val
        35                  40                  45

Thr Ser Ala Thr Gly Lys Val Ile His Gly Arg Tyr Ile Glu Ser Gly
    50                  55                  60

Phe Leu Pro Glu Met Leu Ala Ala Arg Arg Phe Lys Thr Ala Thr Arg
65                  70                  75                  80

Lys Val Leu Asn Ala Met Ser His Ala Gln Lys His Gly Ile Asp Ile
                85                  90                  95

Ser Ala Leu Gly Gly Phe Thr Ser Ile Ile Phe Glu Asn Phe Asp Leu
            100                 105                 110

Ala Lys Leu Arg Gln Val Arg Asp Thr Thr Leu Glu Phe Glu Arg Phe
        115                 120                 125

Thr Thr Gly Asn Thr His Thr Ala Tyr Val Ile Cys Arg Gln Val Glu
    130                 135                 140
```

Ala Ala Ala Lys Thr Leu Gly Ile Asp Ile Ala Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Gly Val Val Glu His Cys
            260                 265                 270

Phe Asp Ile Asp Trp Gln Ile Met Ser Leu Ala Glu Met Ala Arg Pro
        275                 280                 285

Glu Arg Gln Met Phe Ala Cys Phe Ala Glu Ala Met Leu Leu Glu Phe
290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340

<210> SEQ ID NO 65
<211> LENGTH: 347
<212> TYPE: PRT
<213> ORGANISM: Prochlorococcus marinus

<400> SEQUENCE: 65

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
        35                  40                  45

Lys Ser Ala Ile Gly Ile Ser Ile Glu Gly Ser Tyr Ile Glu Ser Cys
50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn

```
                165                 170                 175
Lys Thr Gly Ile Gly Glu Leu Leu Val Ala Arg Gln Lys Glu Pro
            180                 185                 190

Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
    210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
        275                 280                 285

Glu Met Phe Ala Cys Phe Ala Glu Ala Met Ile Leu Glu Phe Glu Lys
    290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Val
            340                 345

<210> SEQ ID NO 66
<211> LENGTH: 347
<212> TYPE: PRT
<213> ORGANISM: Prochlorococcus marinus

<400> SEQUENCE: 66

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
        35                  40                  45

Lys Ser Ala Ile Gly Ile Ser Ile Glu Gly Ser Tyr Ile Asp Ser Cys
    50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
    130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Val Ala Arg Gln Lys Glu Pro
            180                 185                 190
```

```
Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Ile Val Arg Phe Phe Asn Asp
            260                 265                 270

Ile Gly Trp Asn Met Met Glu Leu Ala Glu Met Gln Asn Pro Gln Arg
        275                 280                 285

Glu Met Phe Ala Cys Phe Ala Glu Ala Met Ile Leu Glu Phe Glu Lys
290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Pro
            340                 345

<210> SEQ ID NO 67
<211> LENGTH: 347
<212> TYPE: PRT
<213> ORGANISM: Prochlorococcus marinus

<400> SEQUENCE: 67

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Val Leu Val Glu Asn Val Glu Val
        35                  40                  45

Lys Ser Ala Ile Gly Ile Ser Ile Glu Gly Ser Tyr Ile Asp Ser Cys
50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
210                 215                 220
```

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
            245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
            275                 280                 285

Glu Met Phe Ala Cys Phe Ala Glu Ala Met Ile Leu Glu Phe Glu Lys
            290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Val
            340                 345

<210> SEQ ID NO 68
<211> LENGTH: 347
<212> TYPE: PRT
<213> ORGANISM: Prochlorococcus marinus

<400> SEQUENCE: 68

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
            35                  40                  45

Lys Ser Ala Ile Gly Ile Ser Ile Glu Gly Ser Tyr Ile Asp Ser Cys
50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
            85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
            115                 120                 125

Gly Asn Thr His Thr Ala Trp Val Ile Cys Arg Gln Leu Glu Met Asn
            130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
            165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
            195                 200                 205

Asp Glu Ala Leu Pro Glu Ala Asp Ile Val Val Trp Val Ala Ser Met
            210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly

```
            245                 250                 255
Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
        275                 280                 285

Glu Met Phe Ala Cys Phe Ala Glu Ala Met Ile Leu Glu Phe Glu Lys
    290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Arg Val
                340                 345

<210> SEQ ID NO 69
<211> LENGTH: 347
<212> TYPE: PRT
<213> ORGANISM: Prochlorococcus marinus

<400> SEQUENCE: 69

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
        35                  40                  45

Lys Ser Ala Ile Gly Ile Ser Ile Glu Gly Ser Tyr Ile Asp Ser Cys
    50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
    130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
    210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270
```

```
Ile Gly Trp Asn Met Met Glu Leu Ala Glu Met Gln Asn Pro Gln Arg
            275                 280                 285

Glu Met Phe Ala Cys Phe Ala Glu Ala Met Ile Leu Glu Phe Glu Lys
            290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Ser Ala Val
            340                 345

<210> SEQ ID NO 70
<211> LENGTH: 347
<212> TYPE: PRT
<213> ORGANISM: Prochlorococcus marinus

<400> SEQUENCE: 70

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
            35                  40                  45

Lys Ser Ala Ile Gly Ile Ser Ile Glu Gly Ser Tyr Ile Asp Ser Cys
    50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
            85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
            115                 120                 125

Gly Asn Thr His Thr Ala Trp Val Ile Cys Arg Gln Leu Glu Met Asn
            130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Val Ala Arg Gln Lys Glu Pro
            180                 185                 190

Leu Asp Ser Leu Gln Lys Glu Leu Asp Gly Gly Thr Ile Lys Asn Leu
            195                 200                 205

Asp Glu Ala Leu Pro Glu Ala Asp Ile Val Val Trp Val Ala Ser Met
            210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
            275                 280                 285

Glu Met Phe Ala Cys Phe Ala Glu Ala Met Ile Leu Glu Phe Glu Lys
            290                 295                 300
```

```
Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Gly
                340                 345

<210> SEQ ID NO 71
<211> LENGTH: 347
<212> TYPE: PRT
<213> ORGANISM: Prochlorococcus marinus

<400> SEQUENCE: 71

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
                20                  25                  30

Asp Val Trp Cys Thr Ala Pro Pro Gln Leu Val Glu Asn Val Glu Val
            35                  40                  45

Lys Ser Ala Ile Gly Ile Ser Ile Glu Gly Ser Tyr Ile Asp Ser Cys
50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
                100                 105                 110

His Lys Gln Ile Arg Asn Thr Ser Leu Glu Trp Glu Arg Phe Thr Thr
            115                 120                 125

Gly Asn Thr His Thr Ala Trp Val Ile Cys Arg Gln Leu Glu Met Asn
130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Val Ala Arg Gln Lys Glu Pro
                180                 185                 190

Leu Asp Ser Leu Gln Lys Glu Leu Asp Gly Gly Thr Ile Lys Asn Leu
            195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
        275                 280                 285

Glu Met Phe Ala Cys Phe Glu Ala Met Ile Leu Glu Phe Glu Lys
    290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
```

Gly Leu Asp Lys His Pro Lys Val Asp Ala Val
                340                 345

<210> SEQ ID NO 72
<211> LENGTH: 347
<212> TYPE: PRT
<213> ORGANISM: Prochlorococcus marinus

<400> SEQUENCE: 72

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
        35                  40                  45

Lys Ser Ala Ile Val Ile Ser Ile Glu Gly Ser Tyr Ile Asp Ser Cys
    50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
        275                 280                 285

Glu Met Phe Ala Cys Phe Ala Glu Ala Met Ile Leu Glu Phe Glu Lys
290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Val
            340                 345

<210> SEQ ID NO 73
<211> LENGTH: 347
<212> TYPE: PRT
<213> ORGANISM: Prochlorococcus marinus

<400> SEQUENCE: 73

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
        35                  40                  45

Lys Ser Ala Ile Gly Ile Ser Ile Glu Gly Ser Tyr Ile Asp Ser Cys
    50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
    130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
    210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
        275                 280                 285

Glu Met Phe Ala Cys Phe Glu Ala Met Ile Leu Glu Phe Glu Lys
    290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Thr Ala Val
            340                 345

<210> SEQ ID NO 74
<211> LENGTH: 347
<212> TYPE: PRT
<213> ORGANISM: Prochlorococcus marinus

<400> SEQUENCE: 74

```
Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
        35                  40                  45

Lys Ser Ala Ile Gly Ile Ser Ile Glu Gly Ser Tyr Ile Asp Ser Cys
    50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
    130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Val Ala Arg Gln Lys Glu Pro
            180                 185                 190

Leu Asp Ser Leu Gln Lys Glu Leu Asp Gly Thr Ile Lys Asn Leu
        195                 200                 205

Asp Glu Ala Leu Pro Glu Ala Asp Ile Val Val Trp Val Ala Ser Met
    210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
        275                 280                 285

Glu Met Phe Ala Cys Phe Ala Glu Ala Met Ile Leu Glu Phe Glu Gly
    290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Val
            340                 345

<210> SEQ ID NO 75
<211> LENGTH: 347
<212> TYPE: PRT
<213> ORGANISM: Prochlorococcus marinus

<400> SEQUENCE: 75

Met Ala Phe Gly Leu Ile Gly His Ser Thr Ser Phe Glu Asp Ala Lys
1               5                   10                  15
```

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
            35                  40                  45

Lys Ser Ala Ile Gly Ile Ser Ile Glu Gly Ser Tyr Ile Asp Ser Cys
 50                  55                  60

Phe Val Pro Glu Met Leu Ser Arg Phe Lys Thr Ala Arg Arg Lys Val
 65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
            115                 120                 125

Gly Asn Thr His Thr Ala Trp Val Ile Cys Arg Gln Leu Glu Met Asn
130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
            195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
            275                 280                 285

Glu Met Phe Ala Cys Phe Ala Glu Ala Met Ile Leu Glu Phe Glu Lys
290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Ala Ala Val
            340                 345

<210> SEQ ID NO 76
<211> LENGTH: 347
<212> TYPE: PRT
<213> ORGANISM: Prochlorococcus marinus

<400> SEQUENCE: 76

Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val

```
            35                  40                  45
Lys Ser Ala Ile Gly Ile Ser Ile Glu Gly Ser Tyr Ile Asp Ser Cys
 50                  55                  60

Phe Val Pro Glu Met Leu Ser Arg Phe Lys Thr Ala Arg Arg Lys Val
 65                  70                  75                  80

Leu Asn Ala Met Glu Leu Ala Gln Lys Lys Gly Ile Asn Ile Thr Ala
                 85                  90                  95

Leu Gly Gly Phe Thr Ser Ile Ile Phe Glu Asn Phe Asn Leu Leu Gln
                100                 105                 110

His Lys Gln Ile Arg Asn Thr Ser Leu Glu Trp Glu Arg Phe Thr Thr
                115                 120                 125

Gly Asn Thr His Thr Ala Trp Val Ile Cys Arg Gln Leu Glu Met Asn
130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
                180                 185                 190

Leu Asp Ser Leu Gln Lys Glu Leu Asp Gly Gly Thr Ile Lys Asn Leu
                195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
                260                 265                 270

Ile Gly Trp Asn Met Met Glu Leu Ala Glu Met Gln Asn Pro Gln Arg
                275                 280                 285

Glu Met Phe Ala Cys Phe Ala Glu Ala Met Ile Leu Glu Phe Glu Lys
290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys Pro Pro Lys Val Leu Ala Val
                340                 345

<210> SEQ ID NO 77
<211> LENGTH: 347
<212> TYPE: PRT
<213> ORGANISM: Prochlorococcus marinus

<400> SEQUENCE: 77

Met Ala Phe Gly Leu Ile Gly His Ser Thr Ser Phe Glu Asp Ala Lys
 1               5                  10                  15

Arg Lys Ala Ser Leu Leu Gly Phe Asp His Ile Ala Asp Gly Asp Leu
                 20                  25                  30

Asp Val Trp Cys Thr Ala Pro Pro Gln Leu Val Glu Asn Val Glu Val
                 35                  40                  45

Lys Ser Ala Ile Gly Ile Ser Ile Glu Gly Ser Tyr Ile Asp Ser Cys
 50                  55                  60
```

```
Phe Val Pro Glu Met Leu Ser Arg Phe Lys Thr Ala Arg Arg Lys Val
 65                  70                  75                  80

Leu Asn Ala Met Glu Leu Ala Gln Lys Lys Gly Ile Asn Ile Thr Ala
                 85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
    130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Val Ala Arg Gln Lys Glu Pro
            180                 185                 190

Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270

Ile Glu Trp Asn Met Met Glu Leu Ala Glu Met Gln Asn Pro Gln Arg
        275                 280                 285

Glu Met Phe Ala Cys Phe Ala Glu Ala Met Ile Leu Glu Phe Glu Lys
    290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
                325                 330                 335

Gly Leu Asp Lys His Pro Lys Val Leu Ala Val
            340                 345

<210> SEQ ID NO 78
<211> LENGTH: 345
<212> TYPE: PRT
<213> ORGANISM: Prochlorococcus marinus

<400> SEQUENCE: 78

Met Ala Phe Gly Leu Ile Gly His Ser Thr Ser Phe Glu Asp Ala Lys
 1               5                  10                  15

Arg Lys Ala Ser Leu Leu Gly Phe Asp His Ile Ala Asp Gly Asp Leu
                 20                  25                  30

Asp Val Trp Cys Thr Ala Pro Pro Gln Leu Val Glu Asn Val Glu Val
             35                  40                  45

Lys Ser Ala Ile Gly Ile Ser Ile Glu Gly Ser Tyr Ile Asp Ser Cys
 50                  55                  60

Phe Val Pro Glu Met Leu Ser Arg Phe Lys Thr Ala Arg Arg Lys Val
 65                  70                  75                  80

Leu Asn Ala Met Glu Leu Ala Gln Lys Lys Gly Ile Asn Ile Thr Ala
                 85                  90                  95
```

```
Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
            115                 120                 125

Gly Asn Thr His Thr Ala Trp Val Ile Cys Arg Gln Leu Glu Met Asn
            130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
            165                 170                 175

Lys Thr Gly Ile Gly Glu Leu Leu Val Ala Arg Gln Lys Glu Pro
            180                 185                 190

Leu Asp Ser Leu Gln Lys Glu Leu Asp Gly Gly Thr Ile Lys Asn Leu
            195                 200                 205

Asp Glu Ala Leu Pro Glu Ala Asp Ile Val Val Trp Val Ala Ser Met
210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
            245                 250                 255

Asn Asn Ile His Val Val Lys Gly Gly Ile Val Arg Phe Phe Asn Asp
            260                 265                 270

Ile Gly Trp Asn Met Met Glu Leu Ala Glu Met Gln Asn Pro Gln Arg
            275                 280                 285

Glu Met Phe Ala Cys Phe Ala Glu Ala Met Ile Leu Glu Phe Glu Lys
            290                 295                 300

Cys His Thr Asn Phe Ser Trp Gly Arg Asn Asn Ile Ser Leu Glu Lys
305                 310                 315                 320

Met Glu Phe Ile Gly Ala Ala Ser Val Lys His Gly Phe Ser Ala Ile
            325                 330                 335

Gly Leu Asp Lys His Pro Lys Val Leu
            340                 345

<210> SEQ ID NO 79
<211> LENGTH: 341
<212> TYPE: PRT
<213> ORGANISM: Synechococcus elongatus

<400> SEQUENCE: 79

Ala Phe Gly Leu Ile Gly His Leu Thr Ser Leu Glu Gln Ala Arg Asp
1               5                   10                  15

Val Trp Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
            35                  40                  45

Ser Ala Thr Gly Lys Val Ile His Gly Arg Tyr Ile Glu Ser Cys Phe
50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
            85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
```

```
        115                 120                 125
Thr Gly Asn Thr His Thr Ala Tyr Val Ile Cys Arg Gln Val Glu Ala
        130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340

<210> SEQ ID NO 80
<211> LENGTH: 346
<212> TYPE: PRT
<213> ORGANISM: Prochlorococcus marinus

<400> SEQUENCE: 80

Ala Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Ile Gly Ile Ser Ile Glu Gly Ser Tyr Ile Glu Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Met Asn Ala
    130                 135                 140
```

-continued

```
Pro Lys Ile Gly Ile Asp Leu Lys Ser Ala Thr Val Ala Val Val Gly
145                 150                 155                 160

Ala Thr Gly Asp Ile Gly Ser Ala Val Cys Arg Trp Leu Ile Asn Lys
                165                 170                 175

Thr Gly Ile Gly Glu Leu Leu Leu Val Ala Arg Gln Lys Glu Pro Leu
            180                 185                 190

Asp Ser Leu Gln Lys Glu Leu Asp Gly Gly Thr Ile Lys Asn Leu Asp
        195                 200                 205

Glu Ala Leu Pro Glu Ala Asp Ile Val Val Trp Val Ala Ser Met Pro
        210                 215                 220

Lys Thr Met Glu Ile Asp Ala Asn Asn Leu Lys Gln Pro Cys Leu Met
225                 230                 235                 240

Ile Asp Gly Gly Tyr Pro Lys Asn Leu Asp Glu Lys Phe Gln Gly Asn
                245                 250                 255

Asn Ile His Val Val Lys Gly Gly Ile Val Arg Phe Phe Asn Asp Ile
                260                 265                 270

Gly Trp Asn Met Met Glu Leu Ala Glu Met Gln Asn Pro Gln Arg Glu
            275                 280                 285

Met Phe Ala Cys Phe Ala Glu Ala Met Ile Leu Glu Phe Glu Lys Cys
        290                 295                 300

His Thr Asn Phe Ser Trp Gly Arg Asn Asn Ile Ser Leu Glu Lys Met
305                 310                 315                 320

Glu Phe Ile Gly Ala Ala Ser Val Lys His Gly Phe Ser Ala Ile Gly
                325                 330                 335

Leu Asp Lys His Pro Lys Val Leu Ala Val
                340                 345
```